(12) United States Patent
Letavic et al.

(10) Patent No.: US 10,053,462 B2
(45) Date of Patent: *Aug. 21, 2018

(54) P2X7 MODULATORS

(71) Applicant: Jansssen Pharmaceutica NV, Beerse (BE)

(72) Inventors: Michael A. Letavic, San Diego, CA (US); Dale A. Rudolph, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/375,774

(22) Filed: Dec. 12, 2016

(65) Prior Publication Data

US 2017/0088550 A1   Mar. 30, 2017

Related U.S. Application Data

(63) Continuation of application No. 14/775,436, filed as application No. PCT/US2014/027540 on Mar. 14, 2014, now Pat. No. 9,540,388.

(60) Provisional application No. 61/785,558, filed on Mar. 14, 2013.

(51) Int. Cl.
   *C07D 498/18*   (2006.01)
   *C07D 487/18*   (2006.01)
   *C07D 471/18*   (2006.01)

(52) U.S. Cl.
   CPC ......... *C07D 471/18* (2013.01); *C07D 487/18* (2013.01)

(58) Field of Classification Search
   CPC .................... C07D 498/18; C07D 487/18
   See application file for complete search history.

(56) References Cited

U.S. PATENT DOCUMENTS

| | | | |
|---|---|---|---|
| 4,812,462 A | 3/1989 | Blankley et al. |
| 4,816,463 A | 3/1989 | Blankley et al. |
| 5,338,744 A | 8/1994 | Dudley et al. |
| 8,431,704 B2 | 4/2013 | Love et al. |
| 8,871,760 B2 | 10/2014 | Brotherton-Pleiss et al. |
| 8,933,236 B2 | 1/2015 | Chowdhury et al. |
| 8,987,249 B2 | 3/2015 | Anderskewitz et al. |
| 905,687 A1 | 6/2015 | Adams et al. |
| 9,156,824 B2 | 10/2015 | Dally et al. |
| 9,181,271 B2 | 11/2015 | Li et al. |
| 9,233,974 B2 | 1/2016 | Link et al. |
| 9,242,969 B2 | 1/2016 | Barsanti et al. |
| 9,273,047 B2 | 3/2016 | Hunt et al. |
| 9,290,476 B2 | 3/2016 | Leonard et al. |
| 9,375,418 B2 | 6/2016 | Schmidt et al. |
| 9,434,715 B2 | 9/2016 | Conza et al. |
| 9,447,045 B2 | 9/2016 | Chen et al. |
| 9,532,992 B2 | 1/2017 | Kuntz et al. |
| 9,540,388 B2 * | 1/2017 | Letavic ................. C07D 498/18 |
| 9,561,228 B2 | 2/2017 | Haq et al. |
| 9,617,272 B2 | 4/2017 | Kumar et al. |
| 9,637,456 B2 | 5/2017 | Amans et al. |
| 2005/0096345 A1 | 5/2005 | Thompson et al. |
| 2006/0217448 A1 | 9/2006 | Kelly et al. |
| 2006/0293337 A1 | 12/2006 | Evans et al. |
| 2008/0275052 A1 | 11/2008 | Dhar et al. |
| 2010/0144758 A1 | 6/2010 | Dillon et al. |

(Continued)

FOREIGN PATENT DOCUMENTS

| | | |
|---|---|---|
| CN | 101778850 | 7/2010 |
| JP | 2013-505220 | 2/2013 |

(Continued)

OTHER PUBLICATIONS

Arbeloa et al "P2X7 Receptor Blockade Prevents ATP Excitotoxicity in Neurons and Reduces Brain Damage After Ischemia" Neurobiology of Disease 2012 vol. 45 pp. 954-961.

(Continued)

*Primary Examiner* — Kahsay Habte
(74) *Attorney, Agent, or Firm* — Thomas J. Dodd

(57) ABSTRACT

The present invention is directed to a compound of Formula (I):

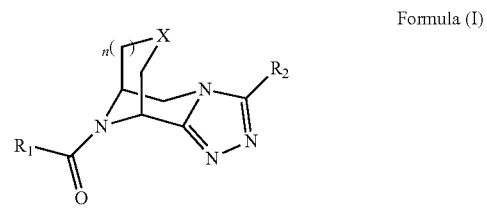

Formula (I)

wherein:

n is an integer from 0-1;

X is CH$_2$ when n is 0, or X is CH$_2$ or oxygen when n is 1;

R$_1$ is phenyl or pyridinyl, wherein the phenyl or pyridinyl is optionally substituted with from 1 to 4 substituents independently selected from halogen and alkyl; and R$_2$ is phenyl, pyridinyl, pyrazinyl, pyradizinyl, pyrimidinyl, pyrrolyl, pyrazolyl, thiazolyl or thiophenyl, wherein the phenyl, pyridinyl, pyrazinyl, pyradizinyl, pyrimidinyl, pyrrolyl, pyrazolyl, thiazolyl or thiophenyl is optionally substituted with from 1 to 2 substituents independently selected from the group consisting of halogen, alkyl, hydroxy and alkoxy.

The invention also relates to pharmaceutical compositions comprising compounds of Formula (I). Methods of making and using the compounds of Formula (I) are also within the scope of the invention.

6 Claims, No Drawings

(56) References Cited

U.S. PATENT DOCUMENTS

| | | |
|---|---|---|
| 2011/0252717 A1 | 10/2011 | Graf Fernandez |
| 2011/0294790 A1 | 12/2011 | Mantegani et al. |
| 2012/0190680 A1 | 7/2012 | Bakthavatchalam et al. |
| 2014/0213554 A1 | 7/2014 | Wu et al. |
| 2014/0251902 A1 | 9/2014 | Solheim et al. |
| 2014/0275015 A1 | 9/2014 | Alcazar Vaca et al. |
| 2014/0275056 A1 | 9/2014 | Letavic et al. |
| 2014/0275096 A1 | 9/2014 | Ameriks et al. |
| 2014/0275120 A1 | 9/2014 | Alcazar Vaca et al. |
| 2015/0290190 A1 | 10/2015 | Ameriks et al. |
| 2015/0322062 A1 | 11/2015 | Alcazar Vaca et al. |
| 2016/0016962 A1 | 1/2016 | Ameriks et al. |
| 2016/0024082 A1 | 1/2016 | Alcazar Vaca et al. |
| 2016/0039809 A1 | 2/2016 | Alcazar Vaca et al. |
| 2016/0039836 A1 | 2/2016 | Letavic et al. |
| 2016/0046596 A1 | 2/2016 | Banerjee et al. |
| 2017/0081342 A1 | 3/2017 | Cheung et al. |

FOREIGN PATENT DOCUMENTS

| | | |
|---|---|---|
| WO | WO2004/014374 | 2/2004 |
| WO | WO 2006023750 | 3/2006 |
| WO | WO 2006/080884 | 8/2006 |
| WO | WO 2006/110516 | 10/2006 |
| WO | WO 2009/002423 | 12/2008 |
| WO | WO 2009/023623 | 2/2009 |
| WO | WO 2010/125101 | 11/2010 |
| WO | WO 2010/125102 | 11/2010 |
| WO | WO2011/121137 | 10/2011 |
| WO | WO 2012/040048 | 3/2012 |
| WO | WO2014/152589 | 9/2014 |
| WO | WO2014/152621 | 9/2014 |
| WO | WO2014/154897 | 10/2014 |
| WO | WO2016/039977 | 3/2016 |
| WO | WO2016/039983 | 3/2016 |

OTHER PUBLICATIONS

Arulkumaran, N., et al. "A Potential Therapeutic Role for P2X7 Receptor (P2X7R) Antagonists in the Treatment of Inflammatory Diseases", Expert Opinion on Investigative Drugs, vol. 20(7), oo. 897-915 (2011).

Avignone et al "Status Epilepticus Induces a Particular Microglial Activation State Characterized by Enhanced Purinergic Signalling" The Journal of Neuroscience 2008 vol. 28(37) pp. 9133-9144.

Bagshawe et al "Antibody-Directed Enzyme Prodrug Therapy: A Review" Drug Development Research 1995 vol. 34 pp. 220-230.

Basso et al "Behavioral Profile of P2X7 Receptor Knockout Mice in Animal Models of Depression and Anxiety: Relevance of Neuropsychiatric Disorders" Behavioral Brain Research 2009 vol. 198 pp. 83-90

Berge et al "Pharmaceutical Salts" Journal of Pharmaceutical Sciences vol. 66(1) pp. 1-19.

Bertolini et al "A New Rational Hypothesis for the Pharmacophore of the Active Metabolite of Leflunomide, A Potent Immunosuppresive Drug" J Med Chem 1997 vol. 40 pp. 2011-2016.

Bodor et al "Novel Approaches to the Design of Safer Drugs: Soft Drugs and Site-Specific Chemical Delivery Systems" Advances in Drug Research 1984 vol. 13 pp. 224-331.

Bourzac et al "Glucose Transporter 2 Expression Is Down Regulated Following P2X7 Activation in Enterocytes" J Cell Physiol 2013 vol. 228 pp. 120-129.

Bundgaard "Design of Prodrugs—(Contents)", Elsevier Science Publishers B.V. (Biomedical Division), 1985.

Capouron et al "Immune System to Brain Signaling: Neuropsychopharmacological Implications" Pharmacology & Therapeutics 2011 vol. 130 pp. 226-238.

Chessel et al "Disruption of the P2X7 Purinoreceptor Gene Abolishes Chronic Inflammatory and Neuropathic Pain" Pain 2005 vol. 114 pp. 386-396.

Chu et al "Inhibitionof P2XY Receptor Ameliorates Transient Global Cerebral Ischemia/Reperfusion Injury Via Modulating Inflammatory Responses in the Rat Hippocampus" Journal of Neuroinflammation 2012 9:69.

Van Nostrand'S Encyclopedia of Chemistry 2005 $5^{th}$ Ed. p. 261 Considine G D. Ed.

Dantzer et al "Cytokine, Sickness Behavior, and Depression" Immunol Allergy Clin N AM 2009 vol. 29 pp. 247-264.

Delarasse et al "The Purinergic Receptor P2X7 Triggers α-Secretase-Dependent Processing of the Amyloid Precursor Protein" Journal of Biological Chemistry 2011 vol. 286(4) pp. 2596-2606.

Diaz-Hernandez et al "Altered P2X7-Receptor Level and Function in Mouse Models of Huntington'S Disease and Therapeutic Efficacy of Antagonist Administration" FASEB J. 2009 vol. 23(6) pp. 1893-1906.

Diaz-Hernandez et al "In Vivo P2X7 Inhibition Reduces Amyloid Plaques in Alzheimer'S Disease Through GXK3β and Secretases" Neurobiology of Aging 2012 vol. 33 pp. 1816-1828.

Donnelly-Roberts et al "[$^3$H]A-804598 ([$^3$H]2-Cyano-1-[ (1S)-1-Phenylethyl]-3-Quinolin-5-Ylguanidine) is a Novel, Potent, and Selective Antagonist Radioligand for P2X7 Receptors" Neuropharmacology 2009 vol. 56 pp. 223-229.

Duan et al "P2X7 Receptors: Properties and Relevance to CNX Function" GLIA 2006 vol. 54 pp. 738-746.

Dyatkin et al "Determination of the Absolute Configuration of a Key Tricyclic Component of a Novel Vasopressing Receptor Antagonist by Use of Vibrational Circular Dichroism" Chirality 2002 vol. 14 pp. 215-219.

Engel et al "Seizure Suppression and Neuroprotection by Targeting the Purinergic P2X7 Receptor During Status Epilepticus in Mice" FASEB J 2012 vol. 26 pp. 1616-1628.

Ferrari et al "The P2X7 Receptor: A Key Player in IL-1 Processing and Release" J Immunol 2006 vol. 176 pp. 3877-3883.

Fleisher et al "Improved Oreal Drug Delivery: Solubility Limitations Overcome by the Use of Prodrugs" Advanced Drug Delivery Reviews 1996 vol. 19 pp. 115-130.

Friedle et al "Recent Patents on Novel P2X7 Receptor Antagonists and Their Potential for Reducing Central Nervous System Inflammation" Recent Patents on CNS Drug Discovery 2010 vol. 5 pp. 35-45.

Furlan-Freguia et al "P2X7 Receptor Signaling Contributes to Tissue Factor-Dependent Thrombosis in Mice" J Clin Invest 2011 vol. 121(7) pp. 2932-2944.

Grygorowicz et al "Temporal Expression of P2X7 Purinergic Receptor During the Course of Experimental Autoimmune Encephalomyelitis" Neurochemistry International 2010 vol. 57 pp. 823-829.

Guile et al., "Antagonists of the $P2X_7$, Receptor. From Lead Identification to Drug Development", Journal of Medicinal Chemistry, May 28, 2009, vol. 52, No. 10, pp. 3123-3141.

Gunosewoyo and Kassiou, "PX2 Purinergic Receptor Ligands: Recently Patented Compounds", Brain and Mind Research Institute, 2010, pp. 625-646.

Hudson, Derek, "Methodological Implications of Simultaneous Solid-Phase Peptide Synthesis. 1. Comparison of Different Coupling Procedures", J. Organic Chemistry, vol. 53, pp. 617-624 (1988).

Keating et al "P2X7 Receptor-Dependent Intestinal Afferent Hypersensitivity in a Mouse Model of Postinfectious Irritable Bowel Syndrome" The Journal of Immunology 2011 vol. 187 pp. 1467-1474.

Killeen, M. E., et al., "Signaling Through Purinergic Receptors for ATP Induces Human Cutaneous Innate and Adaptive Th17 Responses: Implications in the Pathogenesis of Psoriasis", J. Immunology, vol. 190(8), pp. 4324-4336 (2013).

Kim et al "Blockade of P2X7 Receptor Prevents Astroglial Death in the Dentate Gyrus Following Pilocarpine-Induced Status Epilepticus" Neurol Res 2009 vol. 31 pp. 982-988.

Larsen and Bundgaard "A Textbook of Drug Design and Development—(Index)", 1992, 18 Pgs., Harwood Academic Publishers.

Rudolph et al., "Novel Methyl Substituted 1-(5,6-Dihydro- [1,2,4]Triazolo[4,3-A] Pyrazine-7(8H)-YL) Methanones Are P2X7

(56) References Cited

OTHER PUBLICATIONS

Antagonists", Bioorganic & Medicinal Chemistry Letters, vol. 25, No. 16, Aug. 1, 2015 (Aug. 1, 2015), pp. 3157-3162.
Skaper, S., et al., "The P2X7 Purinergic Receptor: From Physiology to Neurological Disorders", FASEB Journal, vol. 24, pp. 337-345 (2010).
Thiboutot, D., J. "Inflammasome Activation by *Propionibacterium Acnes*: The Study of IL-1 in Acne Continues to Unfold", Investigative Dermatology, vol. 134, pp. 595-597 (2014).
Vergani, A. et al., "Long-Term Heart Transplant Survival by Targeting the ionotropic Purinergic Receptor P2X7", Circulation, vol. 127, pp. 463-475 (2013).
Vergani, A., et al., "Effect of the Purinergic Inhibitor Oxidized ATP in a Model of Islet Allograft Rejection", Diabetes, vol. 62, pp. 1665-1675 (2013).
Marcellino et al "On the Role of P2X7 Receptors in Dopamine Nerve Cell Degeneration in a Rat Model of Parkinson's Disease: Studies With the P2X7 Receptor Antagonist A-438079" J Neural Transm 2010 vol. 117 pp. 681-687.
Martins et al "The Role of P2X7 Purinergic Receptors in Inflammatory and Nociceptive Changes Accompanying Cyclophosphamde-Induced Haemorrhagic Cystitis in Mice" Br J Pharmacol 2012 vol. 165 pp. 183-196.
Muller et al "A Potential Role for P2X7R in Allergic Airway Inflammation in Mice and Humans" Am J Respir Cell Mol Biol 2011 vol. 44 pp. 456-464.
Oyanguren-Desez et al "Gain-of-Function of P2X7 Receptor Gene Variants in Multiple Sclerosis" Cell Calcium 2011 vol. 50 pp. 468-472.
Parvathenani et al "P2X7 Mediates Superoxide Production in Primary Microglia and Is Up-Regulated in a Transgenic Mouse Model of Alzheimer's Disease" J Biol Chem 2003 vol. 278(15) pp. 13309-13317.
Paulekuhn et al "Trends in Active Pharmaceutical Ingredient Salt Selection Based on Analysis of Athe Orange Book Database" J Med Chem 2007 vol. 30 pp. 6665-6672.
Robinson et al "Discovery of the Hemifumarate and ($_{\alpha-L}$ Alanyloxy) Methyl Ether as Prodrugs of an Antirheumatic Oxindole: Prodrugs for the Enolic OH Group" J Med Chem 1996 vol. 39 pp. 10-18.
Romagnoli et al "The P2X7 Receptor as a Therapeutic Agent" Expert Opin Ther Targets 2008 vol. 12(5) pp. 647-661.
Sanz et al "Activation of Microglia by Amyloid β Requires P2X7 Receptor Expression" J Immunol 2009 vol. 182 pp. 4378-4385.
Shan et al "Prodrug Strategies Based on Intramolecular Cyclization Reactions" J Pharm Sci 1977 vol. 86(7) pp. 765-767.
Sharp et al "P2X7 Deficiency Suppresses Development of Experimental Autoimmune Encephalomyelitis" J Neuroinflammation 2008 vol. 5 :33.
Skarper et al "The P2X7 Purinergic Receptor: From Physiology to Neurological Disorders" FASEB J 2009 vol. 24 pp. 337-345.
Solini et al "Enhanced P2X7 Activity in Human Fibroblasts From Diabetic Patients—A Possible Pathogenic Mechanism for Vascular Damage in Diabetes" Artherioscler Thromb Vasc Biol 2004 vol. 24 pp. 1240-1245.
Stahl and Wermuth, "Handbook of Pharmaceutical Salts—(Index)", International Union of Pure and Applied Chemistry (Iupac), 3 Pgs.
Suprenant et al "Signaling at Purinergic P2X Receptors" Annu Rev Physiol 2009 vol. 71 pp. 333-359.
Ji et al "P2X7 Deficiency Attenuates Hypertension and Renal Injury in Deoxycorticosterone Acetate-Salt Hypertension" Am J Physiol Renal Physiol 2012 vol. 303 pp. F1207-F1215.
Hackman and Redelmeit, Translastion of Research Evidence From Animals to Humans:, JAMA, 2006, vol. 296. No. 14, 1731-1732.
Jordan, Craig, Tamoxifen: A Most Unlikely Pioneering Medicine:, Nature Reviews, 2003, vol. 2 205-213.
Thomas A. Godwin (Gastrointestinal Diseases, <http://edcenter.med.cornell.edu/CUMC_PathNotes/Gastrointestinal/Gastrointestinal. html>, 51 pages).
Database Chemcats Enamine Screening Library Database Accession 2035772210 Jan. 17, 2008.
Database Chemcats Ukrorgsynthesis Screeing Collection Accession 2033253463 Mar. 6, 2007.
Database Chemcats Ryan Scientific Screening Library Database Accession 2042676574 Jan. 25, 2008.
Database Chemcats Ambinter Stock Screeing Collection Database Accession 2046454718 Feb. 13, 2008.
Database Chemcats Ryan Scientific Screening Library Database Accession 2043876860 Jan. 25, 2008.
Database Chemcats Ryan Scientific Screening Library Database Accession 2042637020 Jan. 25, 2008.
Database Chemcats Ryan Scientific Screening Library Database Accession 2042634059 Jan. 25, 2008.
Database Chemcats Ambinter Stock Screening Collection Database Accession 2040548370 Feb. 13, 2008.
Database Chemcats Ambinter Stock Screening Collection Database Accession 2040381923 Feb. 13, 2008.
Database Chemcats Ambinter Stock Screening Collection Database Accession 2040033692 Feb. 13, 2008.
Database Chemcats Aurora Screening Library Database Accession 2037938546 Sep. 6, 2007.
PCT International Search Report dated Aug. 12, 2014 for International Application No. PCT/US2014/027450.
PCT International Search Report dated Jul. 1, 2014 for International Application No. PCT/US2014/027505.
PCT International Search Report dated Jul. 1, 2014 for International Application No. PCT/US2014/027522.
PCT International Search Report dated Jun. 17, 2014 for International Application No. PCT/US2014/027540.
Janssen Pharmaceutica, NV, U.S. Appl. No. 15/258,320, filed Sep. 7, 2016.
Janssen Pharmaceutica NV, U.S. Appl. No. 62/049,727, filed Sep. 12, 2014.
Janssen Pharmaceutica NV, U.S. Appl. No. 62/049,687, filed Sep. 12, 2014.
European Search Report for corresponding EP Application 08154909.9 dated Jun. 20, 2008.
PCT ISR dated Oct. 15, 2015 for International Application No. PCT/US2015/046852.
U.S. Appl. No. 14/714,714, Notice of Allowance, dated Aug. 15, 2016.
U.S. Appl. No. 14/775,432, Restriction Requirement, Office Action dated Aug. 25, 2016.
Singapore Search Report corresponding to Application No. 11201507259U dated May 5, 2016.
China Application No. 201480027363.2 First Office Action dated May 5, 2016.
PCT ISR dated Jul. 31, 2009 for International Application No. PCT/US2009/041249.
ISR and Written Opinion of PCT/US2014/027540, dated Jun. 17, 2014, 13 Pgs.
PCT ISR dated Oct. 15, 2015 for International Application No. PCT/US2015/046710.
U.S. Appl. No. 14/714,714, Non-Final Rejection Office Action, dated Nov. 23, 2015.
U.S. Appl. No. 14/714,714, Notice of Allowance, dated Mar. 30, 2016.
U.S. Appl. No. 14/714,714, Notice of Allowance, dated Jul. 18, 2016.
U.S. Appl. No. 14/775,424, Non-Final Rejection Office Action, dated Jul. 22, 2016.
U.S. Appl. No. 14/775,424, Non-Final Rejection Office Action, dated Apr. 26, 2016.
Bartlett et al, "The P2X7 Receptor Channel: Recent Developments and the Use of P2X7 Antagonists in Models of Disease", Pharmacol Rev, vol. 66, pp. 638-675, 2014.
Bennet, et al. (Editor), "Part XIV Oncology", Cecil Textbook of Medioine, vol. 1, 20th Edition: pp. 1004-1010 (1996).
Dermer, "Another Anniversary for the War on Cancer", Bio/Technology, vol. 12: pp. 320 (Mar. 1994).
Freshney, et al., Culture of Animal Cells, Manual of Basic Technique, 1933, pp. 1-6, Chapter 1.

(56) References Cited

OTHER PUBLICATIONS

Golub, et al., Molecular Classification of cancer: Class Discovery and class prediction by gene expression monitoring, Science, 1999, pp. 531-537, vol. 286.
Simone, Part XIV—Oncology, Textbook of Medicine, 1996, 20th edition, pp. 1004-1010, vol. 1.

* cited by examiner

P2X7 MODULATORS

CROSS REFERENCE TO RELATED APPLICATIONS

This application claims priority to U.S. Application No. 61/785,558 filed on Mar. 14, 2013.

FIELD OF THE INVENTION

The present invention is related to compounds having P2X7 modulating properties, pharmaceutical compositions comprising these compounds, chemical processes for preparing these compounds and their use in the treatment of diseases associated with P2X7 receptor activity in animals, in particular humans.

BACKGROUND OF THE INVENTION

The P2X7 receptor is a ligand-gated ion channel and is present on a variety of cell types, largely those known to be involved in the inflammatory and/or immune process, specifically, macrophages and monocytes in the periphery and predominantly in glial cells (microglia and astrocytes) of the CNS. (Duan and Neary, *Glia* 2006, 54, 738-746; Skaper et al., *FASEB J* 2009, 24, 337-345; Surprenant and North, *Annu. Rev. Physiol.* 2009, 71, 333-359). Activation of the P2X7 receptor by extracellular nucleotides, in particular adenosine triphosphate, leads to the release of proinflammatory cytokines IL-1β and IL-18 (Muller, et. al. *Am. J. Respir. Cell Mol. Biol.* 2011, 44, 456-464), giant cell formation (macrophages/microglial cells), degranulation (mast cells) and L-selectin shedding (lymphocytes) (Ferrari et al., *J. Immunol.* 2006, 176, 3877-3883; Surprenant and North, *Annu. Rev. Physiol.* 2009, 71, 333-359). P2X7 receptors are also located on antigen-presenting cells (keratinocytes, salivary acinar cells (parotid cells)), hepatocytes, erythrocytes, erythroleukaemic cells, monocytes, fibroblasts, bone marrow cells, neurones, and renal mesangial cells.

The importance of P2X7 in the nervous system arises primarily from experiments using P2X7 knock-out mice. These mice demonstrate the role of P2X7 in the development and maintenance of pain as these mice were protected from the development of both adjuvant-induced inflammatory pain and partial nerve ligation induced neuropathic pain (Chessell et al., *Pain* 2005, 114, 386-396). In addition P2X7 knock-out mice also exhibit an anti-depressant phenotype based on reduced immobility in forced swim and tail suspension tests (Basso et al., *Behav. Brain Res.* 2009, 198, 83-90.). Moreover, the P2X7 pathway is linked to the release of the pro-inflammatory cytokine, IL-1β, which has been linked to precipitation of mood disorders in humans (Dantzer, *Immunol. Allergy Clin. North Am.* 2009, 29, 247-264; Capuron and Miller, *Pharmacol. Ther.* 2011, 130, 226-238). In addition, in murine models of Alzheimer's disease, P2X7 was upregulated around amyloid plaques indicating a role of this target in such pathology as well (Parvathenani et al., *J. Biol. Chem.* 2003, 278, 13309-13317).

In view of the clinical importance of P2X7, the identification of compounds that modulate P2X7 receptor function represents an attractive avenue into the development of new therapeutic agents. Such compounds are provided herein.

SUMMARY OF THE INVENTION

The invention is directed to the general and preferred embodiments defined, respectively, by the independent and dependent claims appended hereto, which are incorporated by reference herein. One aspect of this invention concerns compounds of Formula (I):

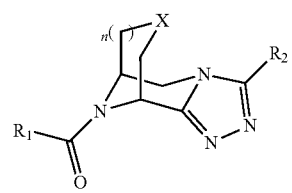

Formula (I)

wherein:
n is an integer from 0-1;
X is $CH_2$ when n is 0, or X is $CH_2$ or oxygen when n is 1;
$R_1$ is phenyl or pyridinyl, wherein the phenyl or pyridinyl is optionally substituted with from 1 to 4 substituents independently selected from halogen and alkyl; and
$R_2$ is phenyl, pyridinyl, pyrazinyl, pyradizinyl, pyrimidinyl, pyrrolyl, pyrazolyl, thiazolyl or thiophenyl, wherein the phenyl, pyridinyl, pyrazinyl, pyradizinyl, pyrimidinyl, pyrrolyl, pyrazolyl, thiazolyl or thiophenyl is optionally substituted with from 1 to 2 substituents independently selected from the group consisting of halogen, alkyl, hydroxy and alkoxy.

Another aspect of this invention concerns compounds of Formula (Ia):

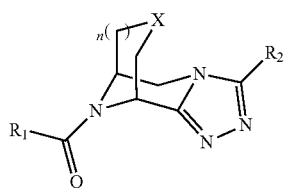

Formula (Ia)

wherein:
n is an integer from 0-1;
X is $CH_2$ when n is 0, or X is $CH_2$ or oxygen when n is 1;
$R_1$ is phenyl or pyridinyl, wherein the phenyl or pyridinyl is optionally substituted with halogen or alkyl; and
$R_2$ is phenyl, pyridinyl, pyrazinyl, pyrimidinyl, pyrrolyl, pyrazolyl, thiazolyl or thiophenyl, wherein the phenyl, pyridinyl, pyrazinyl, pyrimidinyl, pyrrolyl, pyrazolyl, thiazolyl or thiophenyl is optionally substituted with halogen, alkyl, hydroxy or alkoxy.

Further embodiments are provided by a pharmaceutically acceptable salt of a compound of Formula (I). It should be understood that enantiomers and diastereomers of the compounds of Formula (I) are also described, as well as their pharmaceutically acceptable salts.

In certain embodiments, the compound of Formula (I) is a compound selected from those species described or exemplified in the detailed description below.

In a further aspect, the invention relates to pharmaceutical compositions comprising an effective amount of at least one compound of Formula (I), or a pharmaceutically acceptable salt of a compound of Formula (I). Pharmaceutical compositions according to the invention may further comprise one or more pharmaceutically acceptable excipients.

In another aspect, the chemical embodiments of the present invention are useful as P2X7 receptor modulators. Thus, the invention is directed to a method for modulating P2X7 receptor activity, including when such receptor is in a subject, comprising exposing the P2X7 receptor to an effective amount of at least one compound of Formula (I), or a pharmaceutically acceptable salt of a compound of Formula (I).

In another aspect, the invention is directed to a method of treating a subject suffering from or diagnosed with a disease, disorder, or medical condition mediated by P2X7 receptor activity, comprising administering to the subject in need of such treatment an effective amount of at least one compound of Formula (I), or a pharmaceutically acceptable salt of a compound of Formula (I). Additional embodiments of methods of treatment are set forth in the detailed description.

In another aspect, method of studying isotopically labeled compounds in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

An object of the present invention is to overcome or ameliorate at least one of the disadvantages of the conventional methodologies and/or prior art, or to provide a useful alternative thereto.

Additional embodiments of this invention include methods of making a compound of Formula (I), or a pharmaceutically acceptable salt of a compound of Formula (I).

Additional embodiments, features, and advantages of the invention will be apparent from the following detailed description and through practice of the invention.

DETAILED DESCRIPTION OF THE INVENTION

A compound of Formula (I):

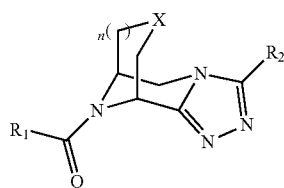

Formula (I)

wherein:
n is an integer from 0-1;
X is $CH_2$ when n is 0, or X is $CH_2$ or oxygen when n is 1;
$R_1$ is phenyl or pyridinyl, wherein the phenyl or pyridinyl is optionally substituted with from 1 to 4 substituents independently selected from halogen and alkyl; and
$R_2$ is phenyl, pyridinyl, pyrazinyl, pyradizinyl, pyrimidinyl, pyrrolyl, pyrazolyl, thiazolyl or thiophenyl, wherein the phenyl, pyridinyl, pyrazinyl, pyradizinyl, pyrimidinyl, pyrrolyl, pyrazolyl, thiazolyl or thiophenyl is optionally substituted with from 1 to 2 substituents independently selected from the group consisting of halogen, alkyl, hydroxy and alkoxy.

Another aspect of this invention concerns compounds of Formula (Ia):

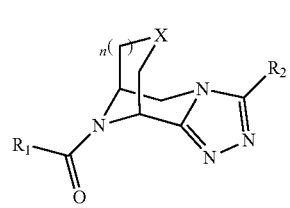

Formula (Ia)

wherein:
n is an integer from 0-1;
X is $CH_2$ when n is 0, or X is $CH_2$ or oxygen when n is 1;
$R_1$ is phenyl or pyridinyl, wherein the phenyl or pyridinyl is optionally substituted with halogen or alkyl; and
$R_2$ is phenyl, pyridinyl, pyrazinyl, pyrimidinyl, pyrrolyl, pyrazolyl, thiazolyl or thiophenyl, wherein the phenyl, pyridinyl, pyrazinyl, pyrimidinyl, pyrrolyl, pyrazolyl, thiazolyl or thiophenyl is optionally substituted with halogen, alkyl, hydroxy or alkoxy.

Enantiomers and diastereomers of the compounds of Formula (I) are also within the scope of the invention. Also within the scope of the invention are the pharmaceutically acceptable salts of the compounds of Formula (I), as well as the pharmaceutically acceptable salts of the enantiomers and diastereomers of the compounds of Formula (I).

The following are various embodiments of compounds of Formula (I), the pharmaceutically acceptable salts of the compounds of Formula (I), as well as the pharmaceutically acceptable salts of the enantiomers and diastereomers of the compounds of Formula (I):

In preferred embodiments, n is 0 and X is $CH_2$.
In certain embodiments, n is 1 and X is $CH_2$. In other embodiments, n is 1 and X is oxygen.
In certain embodiments, $R_1$ is phenyl.
In other embodiments, $R_1$ is phenyl substituted with halogen or alkyl.
In other embodiments, $R_1$ is phenyl di-substituted with halogen, for example chlorine.
In other embodiments, $R_1$ is phenyl di-substituted with alkyl, for example methyl and trifluoromethyl.
In other embodiments, $R_1$ is phenyl di-substituted with halogen and alkyl, for examples chlorine and trifluoromethyl.
In other embodiments, $R_1$ is phenyl ortho substituted with halogen, for example chlorine.
In other embodiments, $R_1$ is phenyl meta substituted with alkyl, for example trifluoromethyl.
In other embodiments, $R_1$ is phenyl di-substituted with halogen at the ortho and para positions, for example chlorine.
In other embodiments, $R_1$ is phenyl di-substituted with alkyl at the ortho and meta positions, for example methyl at the ortho position and trifluoromethyl at the meta position.
In other embodiments, $R_1$ is phenyl tri-substituted with halogen, for example two chlorines and one fluorine.
In other embodiments, $R_1$ is phenyl tri-substituted with halogen at the ortho, meta and para positions, for example two chlorines at the ortho and para positions and one fluorine at the meta position, or two chlorines at the ortho and meta positions and one fluorine at the para position. In preferred embodiments, the ortho and para substitutions are adjacent to the meta substitution.
In other embodiments, $R_1$ is phenyl tri-substituted with halogen and alkyl.

In other embodiments, $R_1$ is phenyl tri-substituted with halogen and alkyl at the ortho, meta and para positions. In preferred embodiments, the ortho and para substitutions are adjacent to the meta substitution.

In certain embodiments, $R_1$ is pyridinyl.

In other embodiments, $R_1$ is pyridinyl that is attached through the 4-position carbon atom.

In other embodiments, $R_1$ is pyridinyl substituted with halogen or alkyl, for example chlorine or fluorine and trifluoromethyl or methyl.

In other embodiments, $R_1$ is pyridinyl that is substituted with halogen and alkyl, for example, chlorine and trifluoromethyl or fluorine and trifluoromethyl.

In other embodiments, $R_1$ is pyridinyl that is di-substituted with alkyl at a meta and an ortho position, for example trifluoromethyl at a meta position and methyl at an ortho position. In preferred embodiments, the alkyl substitutions are adjacent to each other on the phenyl ring.

In other embodiments, $R_1$ is pyridinyl that is di-substituted with alkyl at a meta position and halogen at an ortho position, for examples trifluoromethyl at a meta position and chlorine or fluorine at an ortho position. In preferred embodiments, the alkyl and halogen substitutions are adjacent to each other.

In certain embodiments, $R_2$ is phenyl.

In certain embodiments, $R_2$ is phenyl substituted with halogen, for examples, chlorine or fluorine.

In other embodiments, $R_2$ is phenyl substituted with halogen at the para position, for example fluorine at the para position.

In other embodiments, $R_2$ is pyridinyl.

In other embodiments, $R_2$ is pyridinyl that is attached through the 2-position carbon atom.

In other embodiments, $R_2$ is pyridinyl that is attached through the 3-position carbon atom.

In other embodiments, $R_2$ is pyridinyl that is substituted with alkyl, for example methyl or trifluoromethyl.

In other embodiments, $R_2$ is pyridinyl that is substituted with halogen, for example chlorine or fluorine.

In other embodiments, $R_2$ is pyridinyl that is attached through the 2-position carbon atom and substituted with halogen, for example chlorine or fluorine.

In other embodiments, $R_2$ is pyridinyl that is substituted with halogen at the 5-position of the carbon atom, for example chlorine or fluorine at the 5-position.

In other embodiments, $R_2$ is pyridinyl that is substituted with alkoxy, for example methoxy, ethoxy, propoxy, difluoromethoxy or trifluoromethoxy.

In other embodiments, $R_2$ is pyridinyl that is di-substituted with alkyl and halogen.

In other embodiments, $R_2$ is pyridinyl that is substituted at the 3-position carbon atom.

In other embodiments, $R_2$ is pyridinyl that is substituted with halogen at the 3-position carbon atom, for example fluorine.

In other embodiments, $R_2$ is pyridinyl that is substituted at the 4-position carbon atom.

In other embodiments, $R_2$ is pyridinyl that is substituted with alkyl at the 4-position carbon atom, for example with methyl or trifluoromethyl.

In other embodiments, $R_2$ is pyridinyl that is substituted with alkoxy at the 4-position carbon atom, for example with methoxy.

In other embodiments, $R_2$ is pyridinyl that is substituted at the 5-position carbon atom.

In other embodiments, $R_2$ is pyridinyl that is substituted at the 5-position carbon atom with halogen.

In other embodiments, $R_2$ is pyridinyl that is substituted at the 6-position carbon atom.

In other embodiments, $R_2$ is pyridinyl that is substituted with alkyl at the 6-position carbon atom, for example methyl.

In other embodiments, $R_2$ is pyridinyl that is di-substituted at the 4- and 5-position carbon atom with halogen and alkoxy, for example fluorine and methoxy.

In other embodiments, $R_2$ is pyridinyl that is di-substituted at the 5- and 6-position carbon atom with alkyl and halogen, for example methyl and fluorine.

In other embodiments, $R_2$ is pyrazinyl.

In other embodiments, $R_2$ is pyrazinyl that is attached through the 2-position carbon atom.

In other embodiments, $R_2$ is pyrrolyl.

In other embodiments, $R_2$ is pyrrolyl that is attached through the 2-position carbon atom.

In other embodiments, $R_2$ is pyrimidinyl.

In other embodiments, $R_2$ is pyrimidinyl that is attached through the 2-position carbon atom.

In other embodiments, $R_2$ is pyrimidinyl substituted with halogen.

In other embodiments, $R_2$ is pyrimidinyl substituted with halogen at the 5-position carbon atom.

In other embodiments, $R_2$ is pyrimidinyl substituted with fluorine at the 5-position carbon atom.

In other embodiments, $R_2$ is pyrazolyl.

In other embodiments, $R_2$ is pyrazolyl that is attached through the 2-position carbon atom.

In other embodiments, $R_2$ is pyrazolyl that is attached through the 3-position carbon atom.

In other embodiments, $R_2$ is pyrazolyl that is attached through the 5-position carbon atom.

In other embodiments, $R_2$ is pyrazolyl that is substituted with alkyl.

In other embodiments, $R_2$ is pyrazolyl that is substituted with alkyl at the 3-position carbon atom.

In other embodiments, $R_2$ is pyrazolyl that is substituted with methyl at the 3-position carbon atom.

In other embodiments, $R_2$ is thiazolyl.

In other embodiments, $R_2$ is thiazolyl that is attached through the 2-position carbon atom.

In other embodiments, $R_2$ is thiazolyl that is attached through the 4-position carbon atom.

In other embodiments, $R_2$ is thiazolyl that is attached through the 5-position carbon atom.

In other embodiments, $R_2$ is thiazolyl that is substituted with alkyl.

In other embodiments, $R_2$ is thiazolyl that is substituted with alkyl at the 2-position carbon atom.

In other embodiments, $R_2$ is thiazolyl that is substituted with alkyl at the 4-position carbon atom.

In other embodiments, $R_2$ is thiophenyl.

In other embodiments, $R_2$ is thiophenyl that is attached through the 2-position carbon atom.

In other embodiments, $R_2$ is thiophenyl that is attached through the 3-position carbon atom.

In other embodiments, $R_2$ is thiophenyl that is substituted with alkyl at the 5-position carbon atom.

In other embodiments, $R_2$ is thiazolyl that is substituted with halo at the 5-position carbon atom.

In certain embodiments, $R_1$ is phenyl and $R_2$ is phenyl.

In certain embodiments, $R_1$ is phenyl substituted with halogen and $R_2$ is phenyl substituted with halogen.

In certain embodiments, n is 0, $R_1$ is phenyl substituted with halogen and alkyl and $R_2$ is phenyl substituted with halogen.

In certain embodiments, $R_1$ is phenyl and $R_2$ is pyridinyl.

In other embodiments, $R_1$ is phenyl substituted with alkyl and halogen and $R_2$ is pyridinyl.

In other embodiments, $R_1$ is phenyl substituted with alkyl and halogen and $R_2$ is pyridinyl substituted with halogen.

In other embodiments n is 0, $R_1$ is phenyl and $R_2$ is pyridinyl.

In other embodiments n is 0, $R_1$ is phenyl di-substituted at adjacent ortho and meta positions, and $R_2$ is pyridinyl.

In other embodiments n is 0, $R_1$ is phenyl di-substituted at adjacent ortho and meta positions, and $R_2$ is pyridinyl substituted with halogen.

In certain embodiments, $R_1$ is phenyl and $R_2$ is thiazolyl.

In certain embodiments, $R_1$ is phenyl substituted with one to three halogen and alkyl and $R_2$ is optionally substituted thiazolyl.

In certain embodiments, $R_1$ is pyridinyl substituted with one to three halogen and alkyl and $R_2$ is optionally substituted thiazolyl.

In certain embodiments, $R_1$ is phenyl and $R_2$ is pyrimidinyl.

In certain embodiments, $R_1$ is phenyl substituted with one to three halogen and alkyl and $R_2$ is optionally substituted pyrimidinyl.

In certain embodiments, $R_1$ is pyridinyl substituted with one to three halogen and alkyl and $R_2$ is optionally substituted pyrimidinyl.

In certain embodiments, $R_1$ is phenyl and $R_2$ is pyrazinyl.

In certain embodiments, $R_1$ is phenyl substituted with one to three halogen and alkyl and $R_2$ is optionally substituted pyrazinyl.

In certain embodiments, $R_1$ is pyridinyl substituted with one to three halogen and alkyl and $R_2$ is optionally substituted pyrazinyl.

In certain embodiments, $R_1$ is phenyl and $R_2$ is thiophenyl.

In certain embodiments, $R_1$ is phenyl substituted with one to three halogen and alkyl and $R_2$ is optionally substituted thiophenyl.

In certain embodiments, $R_1$ is pyridinyl substituted with one to three halogen and alkyl and $R_2$ is optionally substituted thiophenyl.

In certain embodiments, $R_1$ is phenyl substituted with from 1 to 3 substituents independently selected from the group consisting of halogen and alkyl.

In certain embodiments, $R_1$ is phenyl substituted with one halogen substituent and one alkyl substituent.

In certain embodiments, $R_1$ is phenyl substituted with three halogen substituents.

In certain embodiments, $R_1$ is pyridinyl optionally substituted with from 1 to 2 substituents independently selected from the group consisting of halogen and alkyl.

In certain embodiments, $R_1$ is 4-pyridinyl optionally substituted with from 1 to 2 substituents independently selected from the group consisting of halogen and alkyl.

In certain embodiments, $R_1$ is 4-pyridinyl substituted with one fluoro substituent and one trifluoromethyl substituent.

In certain embodiments, $R_1$ is 4-pyridinyl substituted with one chloro substituent and one trifluoromethyl substituent.

In certain embodiments, $R_2$ is phenyl substituted with one halogen substituent.

In certain embodiments, $R_2$ is phenyl substituted with one fluorine substituent.

In certain embodiments, $R_2$ is pyridinyl optionally substituted with from 1 to 2 substituents independently selected from the group consisting of halogen, alkyl and alkoxy.

In certain embodiments, $R_2$ is 2-pyridinyl optionally substituted with from 1 to 2 substituents independently selected from the group consisting of halogen, alkyl and alkoxy.

In certain embodiments, $R_2$ is unsubstituted 2-pyridinyl.

In certain embodiments, $R_2$ is pyridinyl substituted with one substituent independently selected from the group consisting of fluorine and chlorine.

In certain embodiments, $R_2$ is pyridinyl substituted with one substituent independently selected from the group consisting of methyl or trifluoromethyl.

In certain embodiments, $R_2$ is unsubstituted pyrazinyl.

In certain embodiments, $R_2$ is pyrimidinyl optionally substituted with one halogen substituent.

In certain embodiments, $R_2$ is pyrimidinyl substituted with one substituent independently selected from the group consisting of fluorine and chlorine.

In certain embodiments, $R_2$ is unsubstituted pyrrolyl.

In certain embodiments, $R_2$ is pyrazolyl optionally substituted with one alkyl substituent.

In certain embodiments, $R_2$ is pyrazolyl substituted with one methyl substituent.

In certain embodiments, $R_2$ is thiazolyl optionally substituted with one alkyl substituent.

In certain embodiments, $R_2$ is thiazolyl substituted with one methyl substituent.

In certain embodiments, $R_2$ is thiophenyl optionally substituted with one substituent independently selected from the group consisting of halogen and alkyl.

In certain embodiments, $R_2$ is thiophenyl substituted with one substituent independently selected from the group consisting of fluorine and chlorine.

In certain embodiments, $R_2$ is thiophenyl substituted with one methyl substituent.

An additional embodiment of the invention is a compound selected from the group consisting of:

11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;

11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;

11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;

11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;

11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;

(6S,10R)-11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;

(6R,10S)-11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;

3-(5-Chloropyridin-2-yl)-1-{[2-chloro-3-(trifluoromethyl)phenyl]carbonyl}-5,6,7,8,9,10-hexahydro-6,10-epimino[1,2,4]triazolo[4,3-a]azocine;

(6S,10R)-3-(5-Chloropyridin-2-yl)-11-{[2-chloro-3-(trifluoromethyl)phenyl]carbonyl}-5,6,7,8,9,10-hexahydro-6,10-epimino[1,2,4]triazolo[4,3-a]azocine;

(6R,10S)-3-(5-Chloropyridin-2-yl)-1-{[2-chloro-3-(trifluoromethyl)phenyl]carbonyl}-5,6,7,8,9,10-hexahydro-6,10-epimino[1,2,4]triazolo[4,3-a]azocine;

11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;

11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;

(6S,10R)-11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;

(6R,10S)-11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;

11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;

(6S,10R)-11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;

(6R,10S)-11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;

(6S,9R)-10-{[2-Chloro-3-(trifluoromethyl)phenyl]carbonyl}-3-(4-fluorophenyl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-pyridin-2-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-pyrazin-2-yl-6,7,8,9-tetrahydro-5H-6,9-epimino[1,2,4]triazolo[4,3-a]azepine;

(6S,9R)-10-{[2-Chloro-4-fluoro-3-(trifluoromethyl)phenyl]carbonyl}-3-pyridin-2-yl-6,7,8,9-tetrahydro-5H-6,9-epimino[1,2,4]triazolo[4,3-a]azepine;

(6S,9R)-10-{[2-Methyl-3-(trifluoromethyl)phenyl]carbonyl}-3-pyridin-2-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(5-fluoropyridin-2-yl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-pyrimidin-2-yl-6,7,8,9-tetrahydro-5H-6,9-epimino[1,2,4]triazolo[4,3-a]azepine;

(6S,9R)-10-[(2,3-Dichloro-4-fluorophenyl)carbonyl]-3-pyrazin-2-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-pyridin-3-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(5-fluoropyrimidin-2-yl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(3-methyl-1H-pyrazol-5-yl)-6,7,8,9-tetrahydro-5H-6,9-epimino[1,2,4]triazolo[4,3-a]azepine;

(6S,9R)-10-{[2-Chloro-4-fluoro-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;

(6S,9R)-10-{[2-Methyl-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;

(6S,9R)-10-[(2,4-Dichloro-3-fluorophenyl)carbonyl]-3-(1,3-thiazol-4-yl)-6,7,8,9-tetrahydro-5H-6,9-epimino[1,2,4]triazolo[4,3-a]azepine;

(6S,9R)-3-(5-Chlorothiophen-2-yl)-10-{[2-chloro-3-(trifluoromethyl)phenyl]carbonyl}-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(2-methyl-1,3-thiazol-4-yl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(1,3-thiazol-5-yl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-thiophen-3-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(4-methyl-1,3-thiazol-5-yl)-6,7,8,9-tetrahydro-5H-6,9-epimino[1,2,4]triazolo[4,3-a]azepine;

(6S,9R)-3-(5-Chlorothiophen-2-yl)-10-{[3-chloro-2-(trifluoromethyl)pyridin-4-yl]carbonyl}-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-thiophen-2-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(1H-pyrrol-2-yl)-6,7,8,9-tetrahydro-5H-6,9-epimino[1,2,4]triazolo[4,3-a]azepine;

(2-chloro-4-fluoro-3-(trifluoromethyl)phenyl)(3-(pyridin-2-yl)-5,6,7,8,9,10-hexahydro-6,10-epimino[1,2,4]triazolo[4,3-a]azocin-11-yl)methanone;

(2-fluoro-3-(trifluoromethyl)phenyl)(3-(pyridin-2-yl)-5,6,7,8,9,10-hexahydro-6,10-epimino[1,2,4]triazolo[4,3-a]azocin-11-yl)methanone;

(3-chloro-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;

((2-methyl-3-(trifluoromethyl)phenyl)(3-(pyridin-2-yl)-5,6,7,8,9,10-hexahydro-6,10-epimino[1,2,4]triazolo[4,3-a]azocin-11-yl)methanone;

(3-methyl-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;

(3-fluoro-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;

(2,4-dichloro-3-fluorophenyl)(3-(pyridin-2-yl)-5,6,7,8,9,10-hexahydro-6,10-epimino[1,2,4]triazolo[4,3-a]azocin-11-yl)methanone;

(2,3-dichloro-4-fluorophenyl)(3-(pyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(3-fluoropyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(3,5-difluoropyridin-2-yl)-5,6,7,8,9,10-hexahydro-6,10-epimino[1,2,4]triazolo[4,3-a]azocin-11-yl)methanone;

((2-chloro-3-(trifluoromethyl)phenyl)(3-(5-fluoro-6-methylpyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(5-fluoro-4-methoxypyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-(trifluoromethoxy)pyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-(difluoromethoxy)pyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-hydroxypyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-ethoxypyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-isopropoxypyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(5-methylpyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-methylpyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-(trifluoromethyl)pyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(5-fluoro-4-methylpyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(5-fluoro-4-(trifluoromethyl)pyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;

((6R,10S)-3-(5-fluoropyrimidin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;

((6R,10S)-3-(5-fluoropyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(pyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(pyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-chloro-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2,3-dichloro-4-fluorophenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-fluoro-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

((6R,10S)-3-(1H-pyrazol-3-yl)-6,7,9,10-tetrahydro-5H-6, 10-epimino[1,2,4]triazolo[3,4-d][1,5]oxazocin-11-yl)(2, 3-dichlorophenyl)methanone;

(2-chloro-3-(trifluoromethyl)phenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-fluorophenyl)-6,7,9,10-tetrahydro-5H-6,10-epimino[1,2,4]triazolo[3,4-d][1,5]oxazocin-11-yl)methanone;

((6R,10S)-3-(4-fluorophenyl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-fluorophenyl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(2-fluoro-3-(trifluoromethyl)phenyl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

(2,3-dichlorophenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

(2,3-dichlorophenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

((6R,10S)-3-(3-fluoropyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(thiazol-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(thiazol-4-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(6R,10S)-11-{[2-Chloro-3-(trifluoromethyl)phenyl]carbonyl}-3-(5-fluoro-6-methylpyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(4-methylpyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyridazin-3-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-[4-(trifluoromethyl)pyridin-2-yl]-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyrimidin-4-yl-5,6,7,8,9,10-hexahydro-6,10-epimino[1,2,4]triazolo[4,3-a]azocine;

(6R,10S)-11-{[3-Fluoro-2-(trifluoromethyl)pyridin-4-yl]carbonyl}-3-pyridin-2-yl-5,6,7,8,9,10-hexahydro-6,10-epimino[1,2,4]triazolo[4,3-a]azocine;

(6R,10S)-11-{[3-Chloro-2-(trifluoromethyl)pyridin-4-yl]carbonyl}-3-pyridin-2-yl-5,6,7,8,9,10-hexahydro-6,10-epimino[1,2,4]triazolo[4,3-a]azocine;

(6R,10S)-11-{[2-Chloro-4-fluoro-3-(trifluoromethyl)phenyl]carbonyl}-3-pyridin-2-yl-5,6,7,8,9,10-hexahydro-6,10-epimino[1,2,4]triazolo[4,3-a]azocine;

(6R,10S)-11-{[2-Methyl-3-(trifluoromethyl)phenyl]carbonyl}-3-pyridin-2-yl-5,6,7,8,9,10-hexahydro-6,10-epimino[1,2,4]triazolo[4,3-a]azocine;

(6R,10S)-11-[(2,4-Dichloro-3-fluorophenyl)carbonyl]-3-pyridin-2-yl-5,6,7,8,9,10-hexahydro-6,10-epimino[1,2,4]triazolo[4,3-a]azocine; and (6R,10S)-11-[(2,3-Dichloro-4-fluorophenyl)carbonyl]-3-pyridin-2-yl-5,6,7,8,9,10-hexahydro-6,10-epimino[1,2,4]triazolo[4,3-a]azocine.

An additional embodiment of the invention is a compound selected from the group consisting of those presented below
11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;

11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;

11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;

11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;

11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;

(6S,10R)-11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;

(6R,10S)-11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;

3-(5-Chloropyridin-2-yl)-1-{[2-chloro-3-(trifluoromethyl)phenyl]carbonyl}-5,6,7,8,9,10-hexahydro-6,10-epimino[1,2,4]triazolo[4,3-a]azocine;

(6S,10R)-3-(5-Chloropyridin-2-yl)-11-{[2-chloro-3-(trifluoromethyl)phenyl]carbonyl}-5,6,7,8,9,10-hexahydro-6,10-epimino[1,2,4]triazolo[4,3-a]azocine;

(6R,10S)-3-(5-Chloropyridin-2-yl)-1-{[2-chloro-3-(trifluoromethyl)phenyl]carbonyl}-5,6,7,8,9,10-hexahydro-6,10-epimino[1,2,4]triazolo[4,3-a]azocine;

11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;

11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;

(6S,10R)-11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;

(6R,10S)-11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;

11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;

(6S,10R)-11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;

(6R,10S)-11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;

(6S,9R)-10-{[2-Chloro-3-(trifluoromethyl)phenyl]carbonyl}-3-(4-fluorophenyl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-pyridin-2-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-pyrazin-2-yl-6,7,8,9-tetrahydro-5H-6,9-epimino[1,2,4]triazolo[4,3-a]azepine;

(6S,9R)-10-{[2-Chloro-4-fluoro-3-(trifluoromethyl)phenyl]carbonyl}-3-pyridin-2-yl-6,7,8,9-tetrahydro-5H-6,9-epimino[1,2,4]triazolo[4,3-a]azepine;

(6S,9R)-10-{[2-Methyl-3-(trifluoromethyl)phenyl]carbonyl}-3-pyridin-2-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(5-fluoropyridin-2-yl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-pyrimidin-2-yl-6,7,8,9-tetrahydro-5H-6,9-epimino[1,2,4]triazolo[4,3-a]azepine;

(6S,9R)-10-[(2,3-Dichloro-4-fluorophenyl)carbonyl]-3-pyrazin-2-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-pyridin-3-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(5-fluoropyrimidin-2-yl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(3-methyl-1H-pyrazol-5-yl)-6,7,8,9-tetrahydro-5H-6,9-epimino[1,2,4]triazolo[4,3-a]azepine;

(6S,9R)-10-{[2-Chloro-4-fluoro-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;

(6S,9R)-10-{[2-Methyl-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;

(6S,9R)-10-[(2,4-Dichloro-3-fluorophenyl)carbonyl]-3-(1,3-thiazol-4-yl)-6,7,8,9-tetrahydro-5H-6,9-epimino[1,2,4]triazolo[4,3-a]azepine;

(6S,9R)-3-(5-Chlorothiophen-2-yl)-10-{[2-chloro-3-(trifluoromethyl)phenyl]carbonyl}-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(2-methyl-1,3-thiazol-4-yl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(1,3-thiazol-5-yl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-thiophen-3-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(4-methyl-1,3-thiazol-5-yl)-6,7,8,9-tetrahydro-5H-6,9-epimino[1,2,4]triazolo[4,3-a]azepine;

(6S,9R)-3-(5-Chlorothiophen-2-yl)-10-{[3-chloro-2-(trifluoromethyl)pyridin-4-yl]carbonyl}-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-thiophen-2-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-(1H-pyrrol-2-yl)-6,7,8,9-tetrahydro-5H-6,9-epimino[1,2,4]triazolo[4,3-a]azepine;

(2-chloro-4-fluoro-3-(trifluoromethyl)phenyl)(3-(pyridin-2-yl)-5,6,7,8,9,10-hexahydro-6,10-epimino[1,2,4]triazolo[4,3-a]azocin-11-yl)methanone;

(2-fluoro-3-(trifluoromethyl)phenyl)(3-(pyridin-2-yl)-5,6,7,8,9,10-hexahydro-6,10-epimino[1,2,4]triazolo[4,3-a]azocin-11-yl)methanone;

(3-chloro-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;

((2-methyl-3-(trifluoromethyl)phenyl)(3-(pyridin-2-yl)-5,6,7,8,9,10-hexahydro-6,10-epimino[1,2,4]triazolo[4,3-a]azocin-11-yl)methanone;

(3-methyl-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;

(3-fluoro-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;

(2,4-dichloro-3-fluorophenyl)(3-(pyridin-2-yl)-5,6,7,8,9,10-hexahydro-6,10-epimino[1,2,4]triazolo[4,3-a]azocin-11-yl)methanone;

(2,3-dichloro-4-fluorophenyl)(3-(pyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(3-fluoropyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(3,5-difluoropyridin-2-yl)-5,6,7,8,9,10-hexahydro-6,10-epimino[1,2,4]triazolo[4,3-a]azocin-11-yl)methanone;

((2-chloro-3-(trifluoromethyl)phenyl)(3-(5-fluoro-6-methylpyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(5-fluoro-4-methoxypyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-(trifluoromethoxy)pyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-(difluoromethoxy)pyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-hydroxypyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-ethoxypyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-isopropoxypyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(5-methylpyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-methylpyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(4-(trifluoromethyl)pyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(5-fluoro-4-methylpyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)(3-(5-fluoro-4-(trifluoromethyl)pyridin-2-yl)-5,6,7,8,9,10-hexahydro-6,10-epimino[1,2,4]triazolo[4,3-a]azocin-11-yl)methanone;

(2-chloro-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;

((6R,10S)-3-(5-fluoropyrimidin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;

((6R,10S)-3-(5-fluoropyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(pyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(pyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-chloro-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2,3-dichloro-4-fluorophenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-fluoro-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2,3-dichlorophenyl)methanone;

(2-chloro-3-(trifluoromethyl)phenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-fluorophenyl)-6,7,9,10-tetrahydro-5H-6,10-epimino[1,2,4]triazolo[3,4-d][1,5]oxazocin-11-yl)methanone;

((6R,10S)-3-(4-fluorophenyl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-fluorophenyl)-6,7,10-tetrahydro-5H-6,10-epimino[1,2,4]triazolo[3,4-d][1,5]oxazocin-11-yl)methanone;

(2,3-dichlorophenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(2-fluoro-3-(trifluoromethyl)phenyl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

(2,3-dichlorophenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

(2,3-dichlorophenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

((6R,10S)-3-(3-fluoropyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(thiazol-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(thiazol-4-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(thiazol-4-yl)-6,7,9,10-tetrahydro-5H-6,10-epimino[1,2,4]triazolo[3,4-d][1,5]oxazocin-11-yl)methanone;

An additional embodiment of the invention is a compound selected from the group consisting of those presented below (6R,10S)-11-{[2-Chloro-3-(trifluoromethyl)phenyl]carbonyl}-3-(5-fluoro-6-methylpyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(4-methylpyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyridazin-3-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-[4-(trifluoromethyl)pyridin-2-yl]-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyrimidin-4-yl-5,6,7,8,9,10-hexahydro-6,10-epimino[1,2,4]triazolo[4,3-a]azocine;

(6R,10S)-11-{[3-Fluoro-2-(trifluoromethyl)pyridin-4-yl]carbonyl}-3-pyridin-2-yl-5,6,7,8,9,10-hexahydro-6,10-epimino[1,2,4]triazolo[4,3-a]azocine;

(6R,10S)-11-{[3-Chloro-2-(trifluoromethyl)pyridin-4-yl]carbonyl}-3-pyridin-2-yl-5,6,7,8,9,10-hexahydro-6,10-epimino[1,2,4]triazolo[4,3-a]azocine;

6R,10S)-11-{[2-Chloro-4-fluoro-3-(trifluoromethyl)phenyl]carbonyl}-3-pyridin-2-yl-5,6,7,8,9,10-hexahydro-6,10-epimino[1,2,4]triazolo[4,3-a]azocine;

(6R,10S)-11-{[2-Methyl-3-(trifluoromethyl)phenyl]carbonyl}-3-pyridin-2-yl-5,6,7,8,9,10-hexahydro-6,10-epimino[1,2,4]triazolo[4,3-a]azocine;

(6R,10S)-11-[(2,4-Dichloro-3-fluorophenyl)carbonyl]-3-pyridin-2-yl-5,6,7,8,9,10-hexahydro-6,10-epimino[1,2,4]triazolo[4,3-a]azocine; and (6R,10S)-11-[(2,3-Dichloro-4-fluorophenyl)carbonyl]-3-pyridin-2-yl-5,6,7,8,9,10-hexahydro-6,10-epimino[1,2,4]triazolo[4,3-a]azocine.

An additional embodiment of the invention is a pharmaceutical composition, comprising:

(a) a therapeutically effective amount of at least one compound of Formula (I):

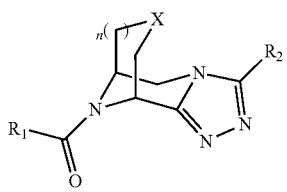

Formula (I)

wherein:

n is an integer from 0-1;

X is $CH_2$ when n is 0, or X is $CH_2$ or oxygen when n is 1;

$R_1$ is phenyl or pyridinyl, wherein the phenyl or pyridinyl is optionally substituted with from 1 to 4 substituents independently selected from halogen and alkyl; and $R_2$ is phenyl, pyridinyl, pyrazinyl, pyradizinyl, pyrimidinyl, pyrrolyl, pyrazolyl, thiazolyl or thiophenyl, wherein the phenyl, pyridinyl, pyrazinyl, pyradizinyl, pyrimidinyl, pyrrolyl, pyrazolyl, thiazolyl or thiophenyl is optionally substituted with from 1 to 2 substituents independently selected from the group consisting of halogen, alkyl, hydroxy and alkoxy, and the pharmaceutically acceptable salts of the compounds of Formula (I), as well as the pharmaceutically acceptable salts of the enantiomers and diastereomers of the compounds of Formula (I); and (b) at least one pharmaceutically acceptable excipient.

An additional embodiment of the invention is a pharmaceutical composition, comprising:

(a) a therapeutically effective amount of at least one compound of Formula (Ia):

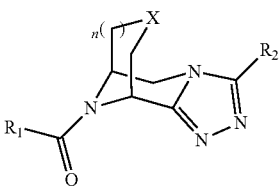

Formula (Ia)

wherein:

n is an integer from 0-1;

X is $CH_2$ when n is 0, or X is $CH_2$ or oxygen when n is 1;

$R_1$ is phenyl or pyridinyl, wherein the phenyl or pyridinyl is optionally substituted with halogen or alkyl; and $R_2$ is phenyl, pyridinyl, pyrazinyl, pyrimidinyl, pyrrolyl, pyrazolyl, thiazolyl or thiophenyl, wherein the phenyl, pyridinyl, pyrazinyl, pyrimidinyl, pyrrolyl, pyrazolyl, thiazolyl or thiophenyl is optionally substituted with halogen, alkyl, hydroxy or alkoxy; and the pharmaceutically acceptable salts of the compounds of Formula (Ia), as well as the pharmaceutically acceptable salts of the enantiomers and diastereomers of the compounds of Formula (Ia); and (b) at least one pharmaceutically acceptable excipient.

An additional embodiment of the invention is a method of treating a subject suffering from or diagnosed with a disease, disorder, or medical condition mediated by P2X7 receptor activity, comprising administering to a subject in need of such treatment an effective amount of at least one compound of Formula (I):

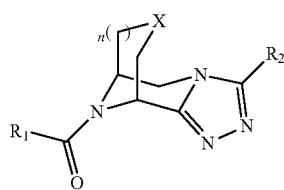

Formula (I)

wherein:

n is an integer from 0-1;

X is $CH_2$ when n is 0, or X is $CH_2$ or oxygen when n is 1;

$R_1$ is phenyl or pyridinyl, wherein the phenyl or pyridinyl is optionally substituted with from 1 to 4 substituents independently selected from halogen and alkyl; and $R_2$ is phenyl, pyridinyl, pyrazinyl, pyradizinyl, pyrimidinyl, pyrrolyl, pyrazolyl, thiazolyl or thiophenyl, wherein the phenyl, pyridinyl, pyrazinyl, pyradizinyl, pyrimidinyl, pyrrolyl, pyrazolyl, thiazolyl or thiophenyl is optionally substituted with from 1 to 2 substituents independently selected from the group consisting of halogen, alkyl, hydroxy and alkoxy; and the pharmaceutically acceptable salts of the compounds of Formula (I), as well as the pharmaceutically acceptable salts of the enantiomers and diastereomers of the compounds of Formula (I).

An additional embodiment of the invention is a method of treating a subject suffering from or diagnosed with a disease, disorder, or medical condition mediated by P2X7 receptor activity, comprising administering to a subject in need of such treatment an effective amount of at least one compound of Formula (Ia):

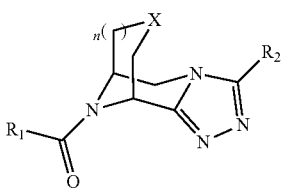

Formula (Ia)

wherein:

n is an integer from 0-1;

X is $CH_2$ when n is 0, or X is $CH_2$ or oxygen when n is 1;

$R_1$ is phenyl or pyridinyl, wherein the phenyl or pyridinyl is optionally substituted with halogen or alkyl; and $R_2$ is phenyl, pyridinyl, pyrazinyl, pyrimidinyl, pyrrolyl, pyrazolyl, thiazolyl or thiophenyl, wherein the phenyl, pyridinyl, pyrazinyl, pyrimidinyl, pyrrolyl, pyrazolyl, thiaz-olyl or thiophenyl is optionally substituted with halogen, alkyl, hydroxy or alkoxy; and the pharmaceutically acceptable salts of the compounds of Formula (I), as well as the pharmaceutically acceptable salts of the enantiomers and diastereomers of the compounds of Formula (I).

In preferred embodiments of the inventive method, the disease, disorder, or medical condition is selected from: diseases of the autoimmune and inflammatory system such as: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease and airway hyper-responsiveness; diseases of the nervous and neuro-immune system such as acute and chronic pain states of neuropathic pain, inflammatory pain, spontaneous pain (opioid induced pain, diabetic neuropathy, postherpetic neuralgia, low back pain, chemotherapy-induced neuropathic pain, fibromyalgia) (Romagnoli, R, et. al., *Expert Opin. Ther. Targets,* 2008, 12(5), 647-661), and diseases involved with and without neuroinflammation of the central nervous system such as mood disorders (major depression, major depressive disorder, treatment resistant depression, bipolar disorder, anxious depression, anxiety) (Friedle, S A, et. al., *Recent Patents on CNS Drug Discovery,* 2010, 5, 35-45, Romagnoli, R, et. al., *Expert Opin. Ther. Targets,* 2008, 12(5), 647-661), cognition, sleep disorders, multiple sclerosis (Sharp A J, et. al., J Neuroinflammation. 2008 Aug. 8; 5:33, Oyanguren-Desez O, et. al., *Cell Calcium.* 2011 November; 50(5):468-72, Grygorowicz T, et. al., *Neurochem Int.* 2010 December; 57(7):823-9), epileptic seizures (Engel T, et. al., *FASEB J.* 2012 April; 26(4):1616-28, Kim J E, et. al. *Neurol Res.* 2009 November; 31(9):982-8, Avignone E, et. al., *J Neurosci.* 2008 Sep. 10; 28(37): 9133-44), Parkinson's disease (Marcellino D, et. al., *J Neural Transm.* 2010 June; 117(6):681-7), schizophrenia, Alzheimer's disease (Diaz-Hernandez J I, et. al., *Neurobiol Aging.* 2012 August; 33(8):1816-28, Delarasse C, *J Biol Chem.* 2011 Jan. 28; 286(4):2596-606, Sanz J M, et. al., *J Immunol.* 2009 Apr. 1; 182(7):4378-85), Huntington's disease (Díaz-Hernández M, et. Al., *FASEB J.* 2009 June; 23(6):1893-906), autism, spinal cord injury and cerebral ischemia/traumatic brain injury (Chu K, et. al., *J Neuroinflammation.* 2012 Apr. 18; 9:69, Arbeloa J, et. al, *Neurobiol Dis.* 2012 March; 45(3):954-61).

P2X7 antagonism may also be beneficial in several stress-related disorders. In addition, P2X7 intervention may be beneficial in diseases of the cardiovascular, metabolic, gastrointestinal and urogenital systems such as diabetes (*Arterioscler Thromb Vasc Biol.* 2004 July; 24(7): 1240-5, *J Cell Physiol.* 2013 January; 228(1):120-9)), thrombosis (Furlan-Freguia C, et. al., *J Clin Invest.* 2011 July; 121(7):2932-44), irritable bowel syndrome, Crohn's disease, ischemic heart disease, hypertension (Ji X, et. al., *Am J Physiol Renal Physiol.* 2012 October; 303(8):F1207-15), myocardial infarction, and lower urinary tract dysfunction such as incontinence. P2X7 antagonism may also present a novel therapeutic strategy for skeletal disorders, namely osteoporosis/osteopetrosis and may also modulate secretory function of exocrine glands. It is also hypothesized that blocking P2X7 may also be beneficial in glaucoma, interstitial cystitis (Martins J P, et. al., *Br J Pharmacol.* 2012 January; 165(1): 183-96) and lower urinary tract syndrome (*Br J Pharmacol.* 2012 January; 165(1):183-96), IBD/IBS (*J Immunol.* 2011 Aug. 1; 187(3):1467-74. Epub 2011 Jun. 22), Sleep, RA/OA, Cough/COPD/asthma, cardiovascular disease, GN, ureteric obstruction, diabetes mellitus, hypertension, sepsis, ischaemia, Amyotrophic Lateral Sclerosis, Chaga's Disease, Chlamydia, Neuroblastoma, Tuberculosis, Polycystic Kidney Disease, and migraine.

An additional embodiment of the invention is a method of treating a subject suffering from or diagnosed with a disease, disorder, or medical condition mediated by P2X7 receptor activity, wherein the disease, disorder, or medical condition is selected from the group consisting of: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease and airway hyper-responsiveness; diseases of the nervous and neuro-immune system such as acute and chronic pain states of neuropathic pain, inflammatory pain, spontaneous pain (opioid induced pain, diabetic neuropathy, postherpetic neuralgia, low back pain, chemotherapy-induced neuropathic pain, fibromyalgia); diseases involved with and without neuroinflammation of the central nervous system such as mood disorders (major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, autism, spinal cord injury and cerebral ischemia/traumatic brain injury, stress-related disorders; diseases of the cardiovascular, metabolic, gastrointestinal and urogenital systems such as diabetes, diabetes mellitus, thrombosis, irritable bowel syndrome, irritable bowel disease, Crohn's disease, ischemic heart disease, ischaemia, hypertension, cardiovascular disease, myocardial infarction, and lower urinary tract dysfunction such as incontinence, lower urinary tract syndrome, Polycystic Kidney Disease, Glomerulonephritis; skeletal disorders, namely osteoporosis/osteopetrosis: and glaucoma, interstitial cystitis, cough, ureteric obstruction, sepsis, Amyotrophic Lateral Sclerosis, Chaga's Disease, chlamydia, neuroblastoma, Tuberculosis, and migraine.

An additional embodiment of the invention is a method of treating a subject suffering from or diagnosed with a disease, disorder, or medical condition mediated by P2X7 receptor activity wherein the disease, disorder or medical condition is treatment resistant depression.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 6 carbon atoms in the chain. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups of the invention can be substituted with, for example, halogen atoms. One exemplary substitutent is fluoro. Preferred substituted alkyl groups of the invention include di- or trihalogenated alkyl groups such as difluoromethyl or trifluoromethyl groups.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. The alkyl group of the alkoxy of the invention can be substituted with, for example, halogen atoms (so that the alkoxy of the invention is a halogenated alkoxy such as difluoromethoxy). One exemplary substitutent of the alkyl group of the alkoxy of the invention is fluoro. Preferred substituted alkyl groups of alkoxy of the invention include di- or trihalogenated alkyl groups such as difluoromethyl or trifluoromethyl groups.

The term "halogen" represents chlorine, fluorine, bromine, or iodine. The term "halo" represents chloro, fluoro, bromo, or iodo.

The terms "hydroxyl" and "hydroxy" refer to an —OH group.

The term "phenyl" represents the following moiety:

Phenyl groups of the inventions can be optionally substituted with, for example, one or more halogens and/or one or more alkyl groups. Exemplary substituents are fluorine, bromine, chlorine, methyl, trifluoromethyl. Preferred substituted phenyl groups of the invention are substituted with one, two, or three halogen, for example two chlorines, two fluorines, or one fluorine and two chlorines. Other preferred substituted phenyl groups of the invention are substituted with one or two alkyl groups, for example a methyl and trifluoromethyl group. Other preferred substituted phenyl groups of the invention are substituted with one or two halogens and one or two alkyl groups, for example one chlorine and one trifluoromethyl group, one fluorine and one trifluoromethyl group, one fluorine and one methyl group, or two halogens (such as a fluorine and chlorine) and one trifluoromethyl group.

The term "pyridinyl" represents the following moiety:

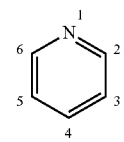

The pyridinyl moiety can be attached through any one of the 2-, 3-, 4-, 5-, or 6-position carbon atoms.

The terms 4-pyridyl, 3-pyridyl and 2-pyridyl represents the following moieties, where the pyridyl nitrogen is designated as the "one" position and the point of attachment is designated as shown below:

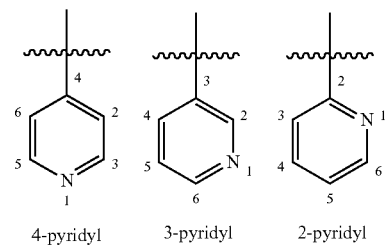

4-pyridyl     3-pyridyl     2-pyridyl

Pyridinyl groups of the invention can be optionally substituted with, for example, one or more alkyl, alkoxy, hydroxy and/or halogen groups. Preferred substituted pyridinyl groups of the invention are substituted with one, two, or three halogens, for example one fluorine, one chlorine, two chlorines, two fluorines, or one fluorine and two chlorines. Other preferred substituted pyridinyl groups of the invention are substituted with one or two alkyl groups, for example a methyl group, a trifluoromethyl group, or a methyl and trifluoromethyl group. Other preferred substituted pyridinyl groups of the invention are substituted with one or two halogens and one or two alkyl groups, for example one chlorine and one trifluoromethyl group, one fluorine and one trifluoromethyl group, one fluorine and one methyl group, or two halogens (such as a fluorine and chlorine) and one trifluoromethyl group. Another preferred substituted pyridinyl group is one or two hydroxyl groups. Another preferred substituted pyridinyl group is one methoxy, difluoromethoxy, trifluoromethoxy, ethoxy or propoxy groups. Another preferred substituted pyridinyl group is one alkoxy and one halogen, for example one methoxy and one fluorine.

The term "pyrimidinyl" represents the following moiety:

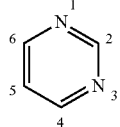

The pyrimidinyl moiety can be attached through any one of the 2-, 4-, 5-, or 6-position carbon atoms. Within the scope of the invention, "pyrimidinyl" groups of the invention can be substituted with one or more halogens, for example one fluorine.

The term "pyrazinyl" represents the following moiety:

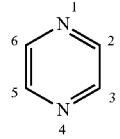

The pyrazinyl moiety can be attached through any one of the 2-, 3-, 5-, or 6-position carbon atoms.

The term "pyradizinyl" represents the following moiety:

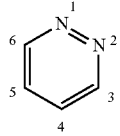

The pyradizinyl moiety can be attached through any one of the 3-, 4-, 5-, or 6-position carbon atoms.

The term "pyrazolyl" represents the following moiety:

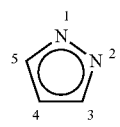

The pyrazolyl moiety can be attached through any one of the 1-, 2-, 3-, 4-, or 5-position carbon atoms. Pyrazolyl groups of the invention can be optionally substituted with, for example, one or more alkyl groups, for example, one methyl group.

The term "pyrrolyl" represents the following moiety:

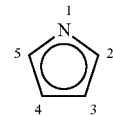

The pyrrolyl moiety can be attached through any one of the 2-, 3-, 4-, or 5-position carbon atoms.

The term "thiazolyl" represents the following moiety:

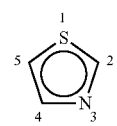

The thiazolyl moiety can be attached through any one of the 2-, 4-, or 5-position carbon atoms. Thiazolyl groups of the invention can be optionally substituted with, for example, one or more alkyl groups, for example, one methyl group.

The term "thiophenyl" represents the following moiety:

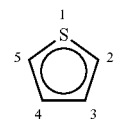

The thiophenyl moiety can be attached through any one of the 2-, 3-, 4-, or 5-position carbon atoms. Thiophenyl groups of the invention can be optionally substituted with, for example, one or more alkyl or halogen groups, for example, one methyl group or one chlorine.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment.

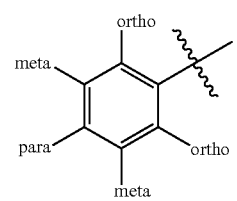

When referring to substituents on the $R_1$ ring, the term "optionally substituted" means that the $R_1$ ring may be substituted with 1 to 4 substituents and the term "substituted" means that the $R_1$ ring is substituted with 1 to 4 substituents.

When referring to substituents on the R₂ ring, the term "optionally substituted" means that the R₂ ring may be substituted with 1 to 2 substituents and the term "substituted" means that the R₂ ring is substituted with 1 to 2 substituents To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting a rotational energy barrier to be overcome to convert from one conformational isomer to another.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enatiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols ▬▬ and ▬◀ are used as meaning the same spatial arrangement in chemical structures shown herein. Analogously, the symbols ⦀⦀⦀⦀ and ⦀⦀⦀⦀ are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) or pharmaceutically acceptable salts of compounds of Formula (I) may be obtained as solvates. Solvates include those formed from the interaction or complexation of compounds of the invention with one or more solvents, either in solution or as a solid or crystalline form. In some embodiments, the solvent is water and then the solvates are hydrates. In addition, certain crystalline forms of compounds of Formula (I) or pharmaceutically acceptable salts of compounds of Formula (I) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The invention includes also pharmaceutically acceptable salts of the compounds of Formula (I), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U. S. Pharmacopoeia or other generally recognized pharmacopoeia for use in animals, and more particularly, in humans.

A "pharmaceutically acceptable salt" is intended to mean a salt of a free acid or base of a compound represented by Formula (I) that is non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "*Pharmaceutical Salts*", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl ($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyl-oxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of the P2X7 receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize or down-regulate the P2X7 receptor expression or activity, and "activators" are compounds that increase, activate, facilitate, sensitize, or up-regulate P2X7 receptor expression or activity.

The term "treat", "treatment" or "treating" as used herein is intended to refer to administration of an active agent or composition of the invention to a subject for the purpose of affecting a therapeutic or prophylactic benefit through modulation of P2X7 receptor activity. Treating includes reversing, ameliorating, alleviating, inhibiting the progress of, lessening the severity of, or preventing a disease, disorder, or condition, or one or more symptoms of such disease, disorder or condition mediated through modulation of P2X7 receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by P2X7 receptor activity, such as: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease (COPD) and airway hyper-responsiveness; diseases of the nervous and neuro-immune system such as acute and chronic pain states of neuropathic pain, inflammatory pain, spontaneous pain (opioid induced pain, diabetic neuropathy, postherpetic neuralgia, low back pain, chemotherapy-induced neuropathic pain, fibromyalgia); diseases involved with and without neuroinflammation of the CNS such as mood disorders (major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, autism, spinal cord injury and cerebral ischemia/traumatic brain injury, stress-related disorders; diseases of the cardiovascular, metabolic, gastrointestinal and urogenital systems such as diabetes, diabetes mellitus, thrombosis, irritable bowel syndrome, IBD, Crohn's disease, ischemic heart disease, ischaemia, hypertension, cardiovascular disease, myocardial infarction, and lower urinary tract dysfunction such as incontinence, lower urinary tract syndrome, Polycystic Kidney Disease, Glomerulonephritis, (GN); skeletal disorders, namely osteoporosis/osteopetrosis: and glaucoma, interstitial cystitis, cough, ureteric obstruction, sepsis, Amyotrophic Lateral Sclerosis, Chaga's Disease, chlamydia, neuroblastoma, Tuberculosis, and migraine.

In treatment methods according to the invention, a therapeutically effective amount of a pharmaceutical agent according to the invention is administered to a subject suffering from or diagnosed as having such a disease, disorder, or condition. The terms "therapeutically effective amount" and "effective amount" mean an amount or dose sufficient to generally bring about the desired therapeutic or prophylactic benefit in patients in need of such treatment for the designated disease, disorder, or condition. Therapeutically effective amounts and effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of compounds of Formula (I) or included with such an agent in a pharmaceutical composition according to the invention. In an exemplary embodiment, additional active ingredients are those that are known or discovered to be effective in the treatment of conditions, disorders, or diseases mediated by P2X7 activity, such as another P2X7 modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semisolid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

EXAMPLES

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Scheme 1

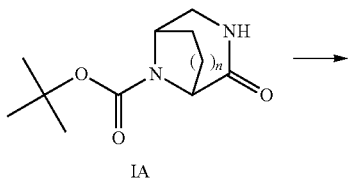

IA

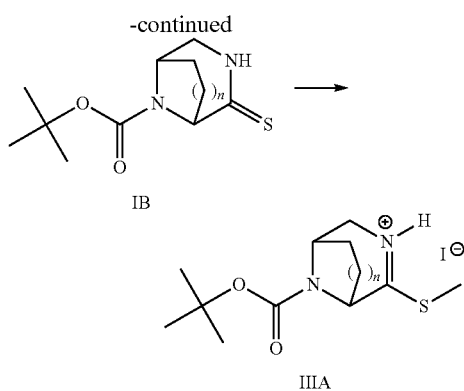

Compound IA can be converted to compound IIA by reaction with Lawesson's reagent, in a solvent such as THF, diethyl ether or DCM. This reaction may be performed at room temperature or heated overnight at or near the boiling point of the solvent.

Compound IIA may be converted to amine IIIA by treatment with an alkylating agent such as methyl iodide in a solvent such as DCM or DMF, at a temperature of between room temperature and 40° C. for between 1 and 48 hours.

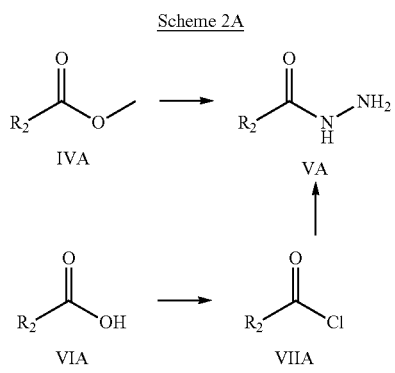

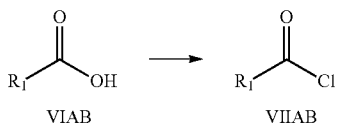

Compound IVA may be converted to compound VA by treatment with hydrazine monohydrate in a solvent such as an alcohol, DCM or DMF at a temperature near room temperature for from 1 to 25 hours. Compound VIA may be converted to compound VIIA by treatment with an appropriate acylating agent such as oxalyl chloride in the presence of a catalyst such as DMF in a solvent such as DCM or DMF for from 1 to 8 hours. Compound VIIA may then also be converted to compound VA by treatment with hydrazine monohydrate in a solvent such as an alcohol, DCM or DMF at a temperature near room temperature for from 1 to 12 hours. Additionally compound VIAB may be converted to compound VIIAB by treatment with an appropriate acylating agent such as oxalyl chloride in the presence of a catalyst such as DMF in a solvent such as DCM or DMF for from 1 to 8 hours. If compounds of type IVA, VIA or VIAB are not commercially available, one skilled in the art will realize there are numerous methods for synthesizing these compounds. These may include hydrolysis of the corresponding nitrile to afford VIA followed by esterification to give IVA. The nitrile in turn can be obtained from a cross-coupling reaction with a suitable halogen containing compound. Hydrolysis of the corresponding nitrile to could also afford VIAB. Or VIA or VIAB can be directly formed from the halogen compound via metal halogen exchange followed by quenching with $CO_2$. VIA or VIAB can also be formed by oxidation of a suitable methyl substituted compound with a reagent, such as, $KMnO_4$ and then IVA may be formed by subsequent esterification of VIA. These compounds can also be formed by oxidation of an appropriately substituted hydroxymethyl compound in either one or two steps to afford VIA or VIAB.

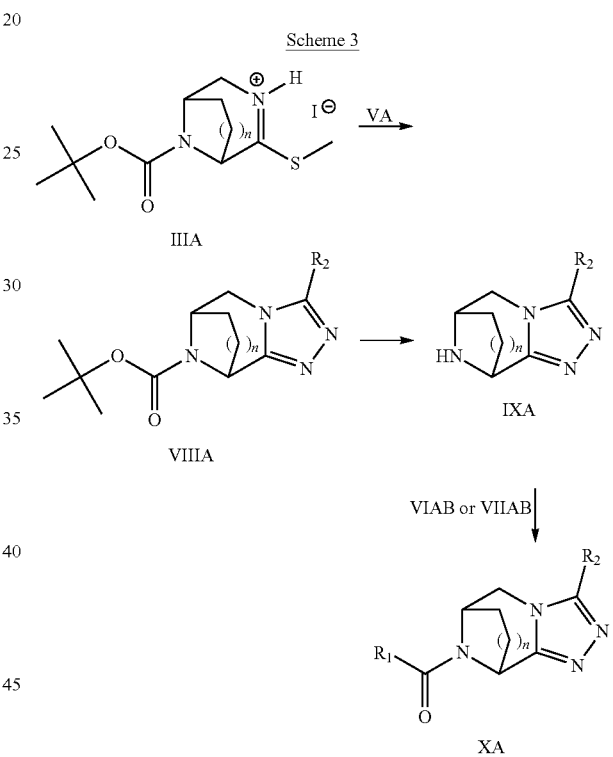

Compound IIIA may be converted to compound VIIIA by the addition of compound VA and a suitable base such as potassium t-butoxide in an alcohol solvent such as methanol. This reaction can be performed at a temperature from room temperature to 120° C. for from 30 minutes to 48 hours. Compound VIIIA can then be converted to compound IXA by addition of a suitable acid such as HCl or TFA, preferably TFA in a solvent such as DCM, DCE or dioxane. This reaction can be performed at a temperature from room temperature to 50° C. for from 30 minutes to 24 hours.

Compound IXA may then be converted to compound XA by the addition of VIIAB and a suitable base such as triethylamine or diisopropylethylamine in a solvent such as DCM, DCE or dioxane at a temperature from room temperature to 50° C. for from 30 minutes to 24 hours. Alternatively compound IXA may be converted to compound XA using compound VIAB and using amide coupling conditions such as HATU, DIPEA in a solvent such as DCM or DMF.

Scheme 4

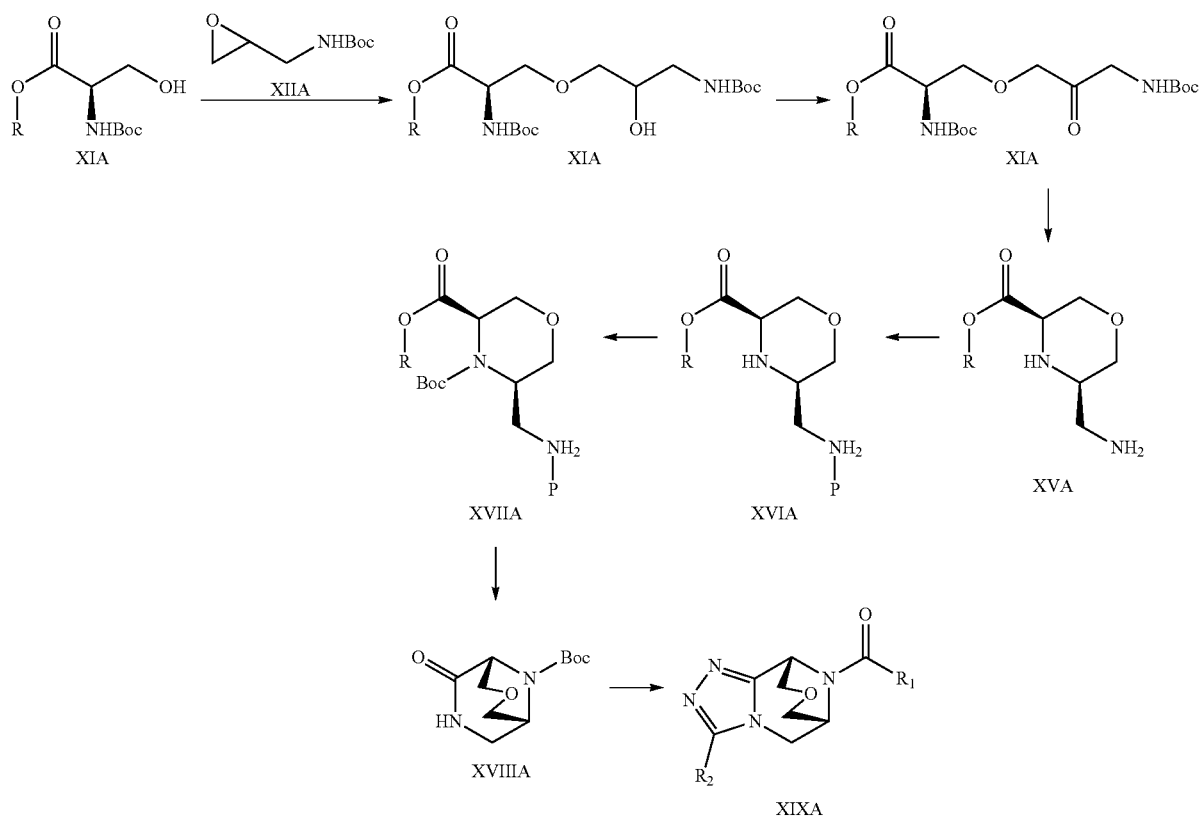

Compound XIA may be converted to compound XIIIA by the addition of XIIA and a suitable base such as sodium hydride in a solvent such as THF or dioxane at a temperature from room temperature to 50° C. for from 30 minutes to 24 hours. Compound XIIIA may then be converted to compound XIVA using as suitable oxidant such as oxalyl chloride and DMSO in a suitable solvent such as DCM, DCE or THF. Compound XIVA may be converted to compound XVA by treatment with an acid such as HCl or TFA followed by the addition of a suitable reductant such as sodium triacetoxyborohydride in a suitable solvent such as THF or dioxane at a temperature from room temperature to 60° C. for from 30 minutes to 24 hours. Compound XVA may be converted to compound XVIA by reaction with a reagent used for the protection of primary amines, such as trifluoroethyl acetate in a solvent such as DCM, DCE or THF at a temperature from room temperature to 50° C. for from 30 minutes to 24 hours. Compound XVIA may then be converted to compound XVIIA by reaction with (Boc)$_2$O in a suitable solvent such as DCM or THF at a temperature around room temperature for from 30 minutes to 24 hours. Compound XVIIA may then be converted to compound XVIIIA by addition of a suitable base such as potassium carbonate in a suitable solvent such as an alcohol, preferably methanol or ethanol at a temperature from room temperature to 70° C. for from 30 minutes to 48 hours. Compound XVIIIA may then be converted to XIXA by the procedures described in Schemes 1-3.

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as Na$_2$SO$_4$ or MgSO$_4$. Where mixtures, solutions, and extracts were "concentrated", they were typically concentrated on a rotary evaporator under reduced pressure. Reactions under microwave irradiation conditions were carried out in a Biotage Initiator or CEM Discover instrument.

Normal-phase silica gel column chromatography (sgc) was performed on silica gel (SiO$_2$) using prepackaged cartridges, eluting with 2 M NH$_3$/MeOH in CH$_2$Cl$_2$ unless otherwise indicated.

Preparative reverse-phase high performance liquid chromatography (HPLC) was performed on a Gilson HPLC with an Xterra Prep RP$_{18}$ (5 μm, 30×100 mm) column, and a gradient of 10 to 99% acetonitrile/water (20 mM NH$_4$OH) over 12 to 18 min, and a flow rate of 30 mL/min.

Preparative supercritical fluid high performance liquid chromatography (SFC) was performed either on a JASCO preparative SFC system, an APS 1010 system from Berger instruments, or a SFC-PICLAB-PREP 200 (PIC SOLUTION, Avignon, France). The separations were conducted between at 100-150 bar with a flow rate ranging from 40-60 mL/min. The columns used were heated to 35-40° C.

Unless otherwise stated, compounds obtained as HCl salts were prepared by the addition of 1 M HCl in diethyl ether to a CH$_2$Cl$_2$ solution of the free base, followed by concentration.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Chemical names were generated using ChemDraw Ultra 6.0.2 (CambridgeSoft Corp., Cambridge, Mass.) or ACD/Name Version 9 (Advanced Chemistry Development, Toronto, Ontario, Canada).

Abbreviations and acronyms used herein include the following:

| Term | Acronym |
| --- | --- |
| High-pressure liquid chromatography | HPLC |
| Diisopropylethylamine | DIPEA |
| Tetrahydrofuran | THF |
| tert-Butylcarbamoyl | Boc or Boc |
| Dichloromethane | DCM |
| Dichloroethane | DCE |
| Trifluoroacetic acid | TFA |
| N,N-Dimethylformamide | DMF |
| Methanol | MeOH |
| Ethanol | EtOH |
| Isopropanol | IPA or iPrOH |
| Potassium tert-butoxide | KOtBu |
| n-Butanol | nBuOH |
| Ethyl Acetate | EtOAc, or EA |
| Triethylamine | TEA |
| 2-(1H-9-Azobenzotriazole-1-yl)-1,1,3,3-tetramethylaminium hexafluorophosphate | HATU |
| N-(3-Dimethylaminopropyl)-N'-ethylcarbodiimide | EDCI |
| 1-Hydroxybenzotriazole | HOBt |
| Supercritical Fluid Chromatography | SFC |
| Isopropyl amine | iPrNH$_2$ |
| Hexane | Hex or hex |
| Not tested | NT |

Intermediate A: tert-Butyl 2-oxo-3,9-diazabicyclo[3.3.1]nonane-9-carboxylate

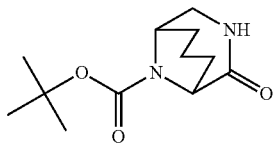 [SMILES: CC(C)(C)OC(=O)N1C2CCCC1C(=O)NC2]

tert-Butyl 2-oxo-3,9-diazabicyclo[3.3.1]nonane-9-carboxylate was prepared according to the procedures in WO 2001042245.

Intermediate B: tert-Butyl 2-thioxo-3,9-diazabicyclo[3.3.1]nonane-9-carboxylate

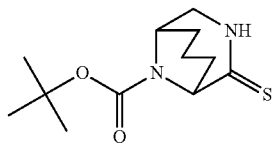 [SMILES: CC(C)(C)OC(=O)N1C2CCCC1C(=S)NC2]

To a solution of tert-butyl 2-oxo-3,9-diazabicyclo[3.3.1]nonane-9-carboxylate (733 mg, 3.05 mmol) in THF (10 mL) was added Lawesson's reagent (700 mg, 1.68 mmol). The mixture was stirred at room temperature overnight and then concentrated in vacuo. The residue was dissolved in EtOAc and washed 3× with saturated aqueous NaHCO$_3$ solution. The combined aqueous layers were extracted several times with EtOAc and the combined organic layers were dried over Na$_2$SO$_4$, filtered and concentrated in vacuo. The residue was chromatographed on SiO$_2$ eluting with EtOAc/Hex to afford the title compound as a colorless foam (622 mg, 79%). MS (ESI): mass calcd. C$_{12}$H$_{20}$N$_2$O$_2$S, 256.12; m/z found, 257.1 [M+H]$^+$. 1H NMR (500 MHz, CDCl$_3$): 8.54-8.20 (m, 1H), 5.23-4.97 (m, 1H), 4.66-4.33 (m, 1H), 3.81-3.63 (m, 1H), 3.28-3.17 (m, 1H), 2.22-2.11 (m, 1H), 1.90-1.58 (m, 5H), 1.47 (s, 9H).

Intermediate C: (E/Z)-(9-(tert-butoxycarbonyl)-3,9-diazabicyclo[3.3.1]nonan-2-ylidene)(methyl)sulfonium Iodide

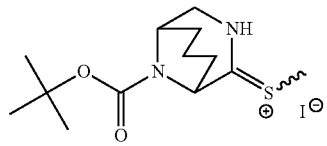

To a solution of Intermediate B (346 mg, 1.35 mmol) in DCM (5 mL) was added MeI (0.42 mL, 6.74 mmol). The mixture was stirred at room temperature for 24 h and then concentrated in vacuo to afford the title compound as an orange foam (540 mg, 100%). MS (ESI): mass calcd. C$_{13}$H$_{22}$N$_2$O$_2$S, 270.14; m/z found, 271.1 [M+H]$^+$.

Intermediate D: Pyrimidine-2-carbohydrazide

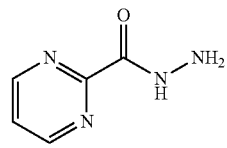

To a slurry of methyl pyrimidine-2-carboxylate (1.0 g, 7.2 mmol) in EtOH (5.6 mL) was added hydrazine monohydrate (0.72 mL, 14 mmol). The reaction mixture became homogeneous and after 5 min a precipitate formed. Stirring was continued for 1 h. The mixture was filtered, and the collected solid was washed with additional EtOH to provide the desired product as a beige solid (720 mg, 72%). MS (ESI): mass calcd. C$_5$H$_6$N$_4$O, 138.1; m/z found, 139.1 [M+H]$^+$. 1H NMR (500 MHz, DMSO-d6): 10.06 (s, 1H), 8.92 (d, J=4.9 Hz, 2H), 7.64 (t, J=4.9 Hz, 1H), 4.64 (s, 2H).

Intermediate E: 2-Chloro-3-(trifluoromethyl)benzoyl Chloride

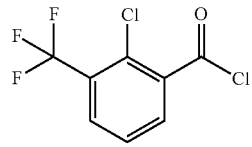 [SMILES: O=C(Cl)c1cccc(C(F)(F)F)c1Cl]

To a suspension of 2-chloro-3-(trifluoromethyl)benzoic acid (15 g, 67 mmol) and catalytic DMF (0.06 mL, 0.67 mmol) in DCM (150 mL) was added oxalyl chloride (6.8 mL, 80 mmol) dropwise. The reaction was let stir (vigorous bubbling) for 4 h and concentrated to an oily solid which became solid after overnight drying on high vacuum.

Intermediate F:
5-Fluoropyrimidine-2-carbohydrazide

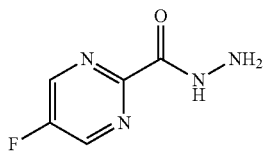 [SMILES: NNC(=O)c1ncc(F)cn1]

Intermediate F, Step a: Methyl 5-fluoropyrimidine-2-carboxylate

To a solution of 5-fluoropyrimidine-2-carbonitrile (513 mg, 4.17 mmol) in MeOH (5 mL) was added 5 mL of concentrated HCl. The mixture was stirred at 80° C. for 2 h. The solution was allowed to cool to room temperature and then treated with a small amount of saturated aqueous $NaHCO_3$ solution and a larger amount of solid $NaHCO_3$. The solution was used to keep everything homogeneous. When the pH reached 6-7 the aqueous layer was extracted with 10% EtOAc/DCM. The combined organic layers containing the ester were dried over $Na_2SO_4$. The aqueous layer was acidified to pH 3-4 with 1 N HCl and then extracted with 10% EtOAc/DCM to afford the acid. The ester layer was filtered, concentrated in vacuo to a white solid (460 mg, 71%). MS (ESI): mass calcd. $C_6H_5FN_2O_2$, 156.03; m/z found, 157.1 [M+H]+. 1H NMR (500 MHz, $CDCl_3$): 8.80 (s, 2H), 4.07 (s, 3H).

Intermediate F, Step b:
5-fluoropyrimidine-2-carbohydrazide

To a heterogeneous mixture of the product of Intermediate F, step a (456 mg, 2.92 mmol) in EtOH (15 mL) was added hydrazine hydrate (0.29 mL, 5.84 mmol). The solid started to go into solution and then a thick white precipitate crashed out. After stirring for 1 h the reaction was complete and concentrated in vacuo to a white solid (487 mg, 100%). MS (ESI): mass calcd. $C_5H_5FN_4O$, 156.04; m/z found, 157.1 [M+H]+. 1H NMR (500 MHz, $CDCl_3$): 8.95-8.79 (m, 1H), 8.73 (s, 2H), 4.26-4.07 (m, 2H).

Intermediate G. 6-Methylpicolinohydrazide

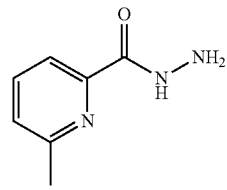

Intermediate G was made in a manner analogous to Intermediate D substituting methyl 6-methylpicolinate for methyl pyrimidine-2-carboxylate to provide the desired compound as a white solid (493 mg, 99%). MS (ESI): mass calcd. $C_7H_9N_3O$, 151.07; m/z found, 152.1 [M+H]+. 1H NMR (500 MHz, $CDCl_3$): 9.67 (s, 1H), 7.85 (t, J=7.7 Hz, 1H), 7.82-7.72 (m, 1H), 7.42 (dd, J=7.7, 0.6 Hz, 1H), 4.59 (s, 2H), 2.56-2.51 (m, 3H).

Intermediate H: (1R,5S)-tert-Butyl 2-oxo-3,8-diazabicyclo[3.2.1]octane-8-carboxylate

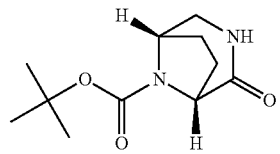 [SMILES: CC(C)(C)OC(=O)N1[C@H]2CC[C@@H]1C(=O)NC2]

(1R,5S)-tert-Butyl 2-oxo-3,8-diazabicyclo[3.2.1]octane-8-carboxylate was prepared according to the procedures in Tetrahedron, 1992, 48, 4985.

Intermediate I: (1R,5S)-tert-butyl 2-thioxo-3,8-diazabicyclo[3.2.1]octane-8-carboxylate

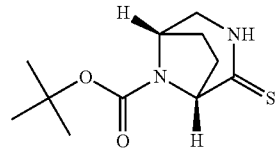 [SMILES: CC(C)(C)OC(=O)N1[C@H]2CC[C@@H]1C(=S)NC2]

Intermediate I was made in a manner analogous to Intermediate B substituting Intermediate H for Intermediate A to provide the desired compound as a white solid (742 mg, 91%). MS (ESI): mass calcd. $C_{11}H_{18}N_2O_2S$, 242.11; m/z found, 243.1 [M+H]+. 1H NMR (500 MHz, $CDCl_3$): 7.64 (s, 1H), 4.89 (s, 1H), 4.51 (s, 1H), 3.79 (s, 1H), 3.10 (dd, J=12.6, 2.7, 1H), 2.28-2.17 (m, 3H), 1.88-1.77 (m, 1H), 1.47 (s, 9H).

Intermediate J: (E/Z)-((1R,5S)-8-(tert-butoxycarbonyl)-3,8-diazabicyclo[3.2.1]octan-2-ylidene)(methyl)sulfonium Iodide

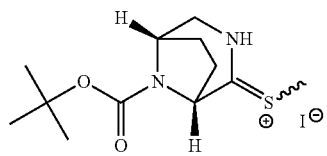

Intermediate J was made in a manner analogous to Intermediate C substituting Intermediate I for Intermediate B to provide the desired compound as a pale yellow foam (258 mg, 100%). MS (ESI): mass calcd. $C_{12}H_{20}N_2O_2S$, 256.12; m/z found, 257.1 [M+H]+.

Example 1: 11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine

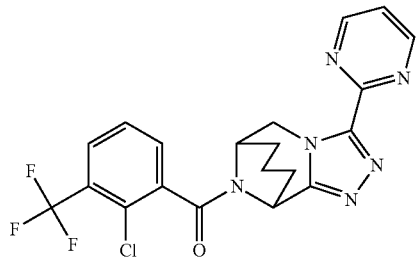

Example 1, Step a: tert-butyl-3-(pyrimidin-2-yl)-5,6,7,8,9,10-hexahydro-6,10-epimino[1,2,4]triazolo[4,3-a]azocine-11-carboxylate To a round bottom flask was added Intermediate C (180 mg, 0.451 mmol), Intermediate D (69 mg, 0.497 mmol) and n-BuOH (2 mL). To this suspension was added KOtBu (63 mg, 0.564 mmol). After 30 min at room temperature, the mixture was heated at 120° C. for 24 h. The mixture was concentrated in vacuo and taken on to the next step without further purification. MS (ESI): mass calcd. $C_{17}H_{22}N_6O_2$, 342.18; m/z found, 343.1 $[M+H]^+$.

Example 1, Step b: 3-(pyrimidin-2-yl)-5,6,7,8,9,10-hexahydro-6,10-epimino[1,2,4]triazolo[4,3-a]azocine To a solution of the product of Example 1, step a (157 mg, 0.459 mmol) in DCM (2 mL) was added TFA (1 mL). The mixture was stirred for 2 h at room temperature and then concentrated in vacuo. The residue was chromatographed on $SiO_2$ eluting with 2 M $NH_3$ in MeOH/DCM to afford the title compound as a colorless foam (68 mg, 61%). MS (ESI): mass calcd. $C_{12}H_{14}N_6$, 242.13; m/z found, 243.1 $[M+H]^+$. 1H NMR (500 MHz, $CDCl_3$): 8.89 (d, J=4.9 Hz, 2H), 7.34 (t, J=4.9 Hz, 1H), 4.68-4.52 (m, 3H), 3.72-3.66 (m, 1H), 2.13-1.62 (m, 6H), 1.33-1.17 (m, 1H).

Example 1, Step c: 11-{[2-chloro-3-(trifluoromethyl)phenyl]carbonyl}-3-pyrimidin-2-yl-5,6,7,8,9,10-hexahydro-6,10-epimino[1,2,4]triazolo[4,3-a]azocine To a solution of the product of Example 1, step b (65 mg, 0.266 mmol) in DCM (3 mL) was added Intermediate E (68 mg, 0.280 mmol) followed by TEA (0.05 mL, 0.320 mmol). The reaction was stirred at room temperature overnight and then loaded directly on a $SiO_2$ column eluting with IPA/EtOAc to afford the title compound (103 mg, 86%). MS (ESI): mass calcd. $C_{20}H_{16}ClF_3N_6O$, 448.10; m/z found, 448.9 $[M+H]^+$. 1H NMR (500 MHz, $CDCl_3$): 8.95-8.86 (m, 2H), 7.83-7.76 (m, 1H), 7.61-7.34 (m, 3H), 6.49-5.44 (m, 1H), 5.09-3.98 (m, 3H), 2.24-1.75 (m, 5H), 1.46-1.32 (m, 1H).

Example 2: (6S*,10R*)-11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine

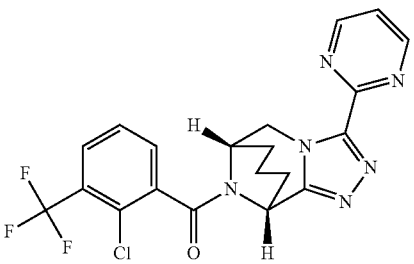 [SMILES: O=C(c1cccc(C(F)(F)F)c1Cl)N1[C@H]2CCC[C@@H]1c1nnc(-c3ncccn3)n1C2]

The title compound, absolute configuration unknown, was obtained as a single enantiomer by Chiral SFC purification of Example 1 performed using a CHIRALCEL OD-H (250×20 mm) column and a mobile phase of 75% $CO_2$, 25% MeOH. The enantiomeric purity was confirmed by analytical SFC using a CHIRALCEL OD-H (250×4.6 mm) column and a mobile phase of 70% $CO_2$, 30% MeOH containing 0.3% $iPrNH_2$ over 7 minutes. (100% single enantiomer, 2.94 min retention time). MS (ESI): mass calcd. $C_{20}H_{16}ClF_3N_6O$, 448.10; m/z found, 448.8 $[M+H]^+$.

Example 3: (6R*,10S*)-11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine

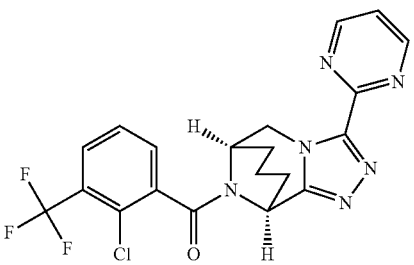 [SMILES: O=C(c1cccc(C(F)(F)F)c1Cl)N1[C@@H]2CCC[C@H]1c1nnc(-c3ncccn3)n1C2]

The title compound, absolute configuration unknown, was obtained as a single enantiomer by Chiral SFC purification of Example 1 performed using a CHIRALCEL OD-H (250×20 mm) column and a mobile phase of 75% $CO_2$, 25% MeOH. The enantiomeric purity was confirmed by analytical SFC using a CHIRALCEL OD-H (250×4.6 mm) column and a mobile phase of 70% $CO_2$, 30% MeOH containing 0.3% $iPrNH_2$ over 7 minutes. (100% single enantiomer, 3.66 min retention time). MS (ESI): mass calcd. $C_{20}H_{16}ClF_3N_6O$, 448.10; m/z found, 448.8 $[M+H]^+$.

Example 4: 11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine

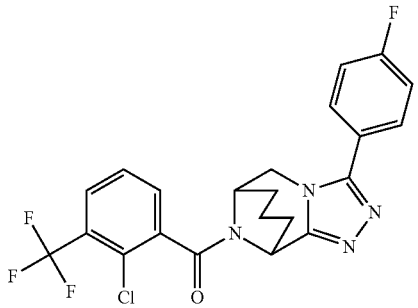 [SMILES: O=C(c1cccc(C(F)(F)F)c1Cl)N1C2CCCC1c1nnc(-c3ccc(F)cc3)n1C2]

The title compound was prepared in a manner analogous to Example 1 substituting 4-fluorobenzohydrazide for Intermediate D. MS (ESI): mass calcd. $C_{22}H_{17}ClF_4N_4$, 464.10; m/z found, 464.9 [M+H]$^+$. 1H NMR (500 MHz, CDCl$_3$): 7.84-7.69 (m, 3H), 7.59-7.30 (m, 2H), 7.26-7.17 (m, 2H), 5.51-5.44 (m, 1H), 5.07-3.94 (m, 3H), 2.23-1.74 (m, 5H), 1.35-1.23 (m, 1H).

Example 5: (6S*,10R*)-11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine

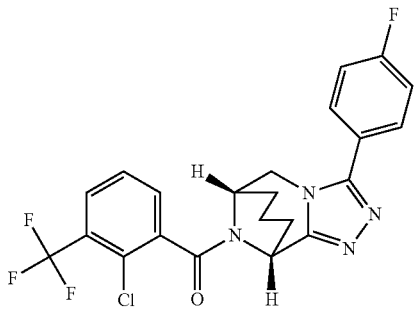 [SMILES: O=C(c1cccc(C(F)(F)F)c1Cl)N1[C@H]2CCC[C@@H]1c1nnc(-c3ccc(F)cc3)n1C2]

The title compound, absolute configuration unknown, was obtained as a single enantiomer by Chiral SFC purification of Example 4 performed using a CHIRALPAK IA (250×20 mm) column and a mobile phase of 70% CO$_2$, 30% mixture of EtOH/iPrOH 50/50 (v/v). The enantiomeric purity was confirmed by analytical SFC using a CHIRALPAK IA (250×4.6 mm) column and a mobile phase of 70% CO$_2$, 15% EtOH, 15% iPrOH containing 0.3% iPrNH$_2$ over 7 minutes. (100% single enantiomer, 3.05 min retention time). MS (ESI): mass calcd. $C_{22}H_{17}ClF_4N_4O$, 464.10; m/z found, 464.9 [M+H]$^+$.

Example 6: (6R*,10S*)-11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine

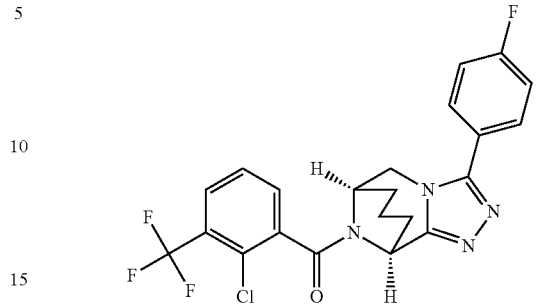

The title compound, absolute configuration unknown, was obtained as a single enantiomer by Chiral SFC purification of Example 4 performed using a CHIRALPAK IA (250×20 mm) column and a mobile phase of 70% CO$_2$, 30% mixture of EtOH/iPrOH 50/50 (v/v). The enantiomeric purity was confirmed by analytical SFC using a CHIRALPAK IA (250×4.6 mm) column and a mobile phase of 70% CO$_2$, 15% EtOH, 15% iPrOH containing 0.3% iPrNH$_2$ over 7 minutes. (98.8% single enantiomer, 3.31 min retention time). MS (ESI): mass calcd. $C_{22}H_{17}ClF_4N_4O$, 464.10; m/z found, 464.8 [M+H]$^+$.

Example 7: 11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine

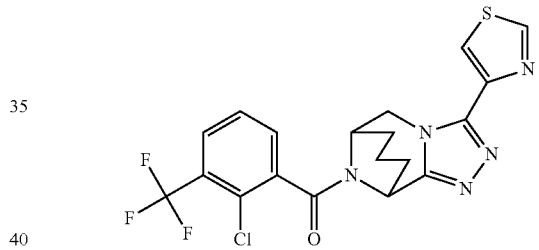

The title compound was prepared in a manner analogous to Example 1 substituting thiazole-4-carboxylic acid hydrazide for Intermediate D. MS (ESI): mass calcd. $C_{19}H_{15}ClF_3N_5OS$, 453.06; m/z found, 453.9 [M+H]$^+$. 1H NMR (500 MHz, CDCl$_3$): 8.95-8.84 (m, 1H), 8.31-8.25 (m, 1H), 7.82-7.77 (m, 1H), 7.60-7.39 (m, 2H), 6.44-5.44 (m, 1H), 5.04-3.97 (m, 3H), 2.23-1.73 (m, 5H), 1.47-1.32 (m, 1H).

Example 8: (6S*,10R*)-11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine

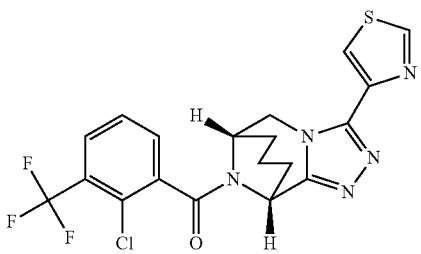 [SMILES: O=C(c1cccc(C(F)(F)F)c1Cl)N1[C@H]2CCC[C@@H]1c1nnc(-c3cscn3)n1C2]

The title compound, absolute configuration unknown, was obtained as a single enantiomer by Chiral SFC purification of Example 7 performed using a CHIRALCEL OD-H (250× 20 mm) column and a mobile phase of 75% $CO_2$, 25% MeOH. The enantiomeric purity was confirmed by analytical SFC using a CHIRALCEL OD-H (250×4.6 mm) column and a mobile phase of 70% $CO_2$, 25% MeOH containing 0.3% $iPrNH_2$ over 7 minutes. (100% single enantiomer, 5.10 min retention time). MS (ESI): mass calcd. $C_{19}H_{15}ClF_3N_5OS$, 453.06; m/z found, 453.8 $[M+H]^+$.

Example 9: (6R*,10S*)-11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine

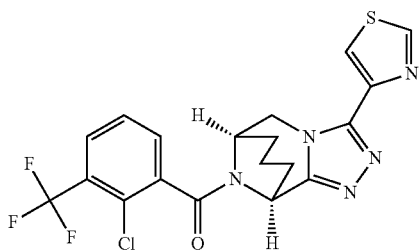 [SMILES: O=C(c1cccc(C(F)(F)F)c1Cl)N1[C@@H]2CCC[C@H]1c1nnc(-c3cscn3)n1C2]

The title compound, absolute configuration unknown, was obtained as a single enantiomer by Chiral SFC purification of Example 7 performed using a CHIRALCEL OD-H (250× 20 mm) column and a mobile phase of 75% $CO_2$, 25% MeOH. The enantiomeric purity was confirmed by analytical SFC using a CHIRALCEL OD-H (250×4.6 mm) column and a mobile phase of 70% $CO_2$, 25% MeOH containing 0.3% $iPrNH_2$ over 7 minutes. (99.3% single enantiomer, 6.00 min retention time). MS (ESI): mass calcd. $C_{19}H_{15}ClF_3N_5OS$, 453.06; m/z found, 453.8 $[M+H]^+$.

Example 10: 11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine

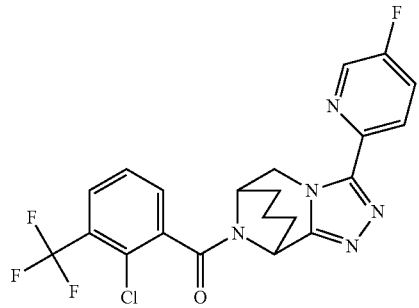

The title compound was prepared in a manner analogous to Example 1 substituting 5-fluoro-pyridine-2-carboxylic acid hydrazide for Intermediate D. MS (ESI): mass calcd. $C_{21}H_{16}ClF_4N_5O$, 465.10; m/z found, 466.1 $[M+H]^+$.

Example 11: (6S*,10R*)-11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine

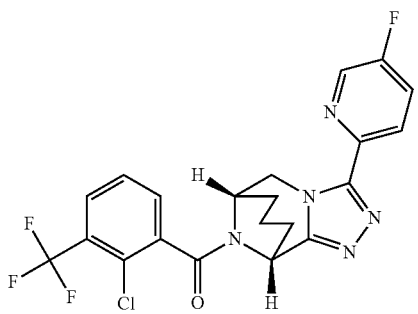

The title compound, absolute configuration unknown, was obtained as a single enantiomer by Chiral SFC purification of Example 10 performed using a CHIRALPAK AD-H (250×20 mm) column and a mobile phase of 70% $CO_2$, 30% mixture of EtOH/iPrOH 50/50 (v/v). The enantiomeric purity was confirmed by analytical SFC using a Chiralpak AD-H (250×4.6 mm) column and a mobile phase of 70% $CO_2$, 15% EtOH, 15% iPrOH containing 0.3% $iPrNH_2$ over 7 minutes. (100% single enantiomer, 3.50 min retention time). MS (ESI): mass calcd. $C_{21}H_{16}ClF_4N_5O$, 465.10; m/z found, 465.8 $[M+H]^+$.

Example 12: (6R*,10S*)-11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine

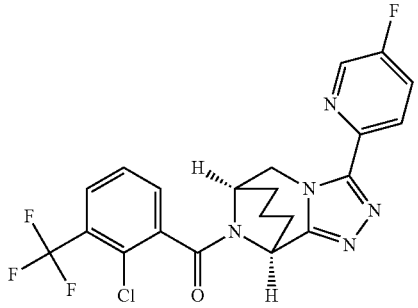 [SMILES: O=C(c1cccc(C(F)(F)F)c1Cl)N1[C@@H]2CCC[C@H]1c1nnc(-c3ccc(F)cn3)n1C2]

The title compound, absolute configuration unknown, was obtained as a single enantiomer by Chiral SFC purification of Example 10 performed using a CHIRALPAK AD-H (250×20 mm) column and a mobile phase of 70% $CO_2$, 30% mixture of EtOH/iPrOH 50/50 (v/v). The enantiomeric purity was confirmed by analytical SFC using a CHIRALPAK AD-H (250×4.6 mm) column and a mobile phase of 70% $CO_2$, 15% EtOH, 15% iPrOH containing 0.3% $iPrNH_2$ over 7 minutes. (100% single enantiomer, 4.30 min retention time). MS (ESI): mass calcd. $C_{21}H_{16}ClF_4N_5O$, 465.10; m/z found, 465.8 $[M+H]^+$.

Example 13: 11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine

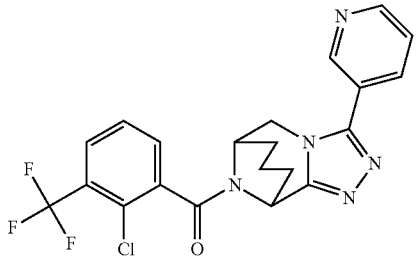 [SMILES: O=C(c1cccc(C(F)(F)F)c1Cl)N1C2CCCC1c1nnc(-c3cccnc3)n1C2]

The title compound was prepared in a manner analogous to Example 1 substituting nicotinic acid hydrazide for Intermediate D. MS (ESI): mass calcd. $C_{21}H_{17}ClF_3N_5O$, 447.11; m/z found, 448.1 $[M+H]^+$.

Example 14: (6S*,10R*)-11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine

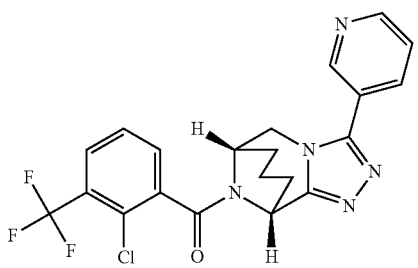 [SMILES: O=C(c1cccc(C(F)(F)F)c1Cl)N1[C@H]2CCC[C@@H]1c1nnc(-c3cccnc3)n1C2]

The title compound, absolute configuration unknown, was obtained as a single enantiomer by Chiral SFC purification of Example 13 performed using a CHIRALPAK AD-H (250×20 mm) column and a mobile phase of 70% $CO_2$, 30% mixture of EtOH/iPrOH 50/50 (v/v). The enantiomeric purity was confirmed by analytical SFC using a CHIRALPAK AD-H (250×4.6 mm) column and a mobile phase of 70% $CO_2$, 15% EtOH, 15% iPrOH containing 0.3% $iPrNH_2$ over 7 minutes. (100% single enantiomer, 2.76 min retention time). MS (ESI): mass calcd. $C_{21}H_{17}ClF_3N_5O$, 447.11; m/z found, 447.8 $[M+H]^+$. 1H NMR (500 MHz, $CDCl_3$): 9.06-8.90 (m, 1H), 8.82-8.72 (m, 1H), 8.18-8.12 (m, 1H), 7.86-7.79 (m, 1H), 7.61-7.31 (m, 3H), 6.48-5.46 (m, 1H), 5.10-3.99 (m, 3H), 2.26-1.72 (m, 5H), 1.39-1.19 (m, 1H).

Example 15: (6R*,10S*)-11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine

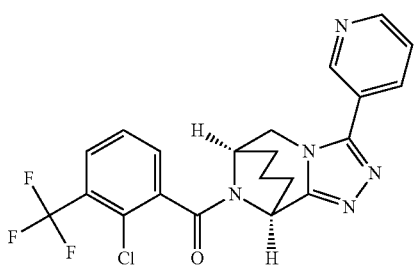 [SMILES: O=C(c1cccc(C(F)(F)F)c1Cl)N1[C@@H]2CCC[C@H]1c1nnc(-c3cccnc3)n1C2]

The title compound, absolute configuration unknown, was obtained as a single enantiomer by Chiral SFC purification of Example 13 performed using a CHIRALPAK AD-H (250×20 mm) column and a mobile phase of 70% $CO_2$, 30% mixture of EtOH/iPrOH 50/50 (v/v). The enantiomeric purity was confirmed by analytical SFC using a CHIRALPAK AD-H (250×4.6 mm) column and a mobile phase of 70% $CO_2$, 15% EtOH, 15% iPrOH containing 0.3% $iPrNH_2$ over 7 minutes. (100% single enantiomer, 3.79 min retention time). MS (ESI): mass calcd. $C_{21}H_{17}ClF_3N_5O$, 447.11; m/z found, 447.8 $[M+H]^+$.

Example 16: 11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine

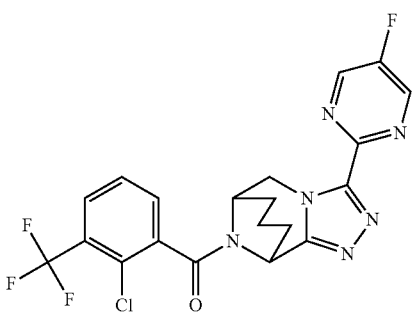 [SMILES: O=C(c1cccc(C(F)(F)F)c1Cl)N1C2CCCC1c1nnc(-c3ncc(F)cn3)n1C2]

The title compound was prepared in a manner analogous to Example 1 substituting Intermediate F for Intermediate D. MS (ESI): mass calcd. $C_{20}H_{15}ClF_4N_6O$, 466.09; m/z found, 467.1 $[M+H]^+$.

Example 17: (6S*,10R*)-11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine

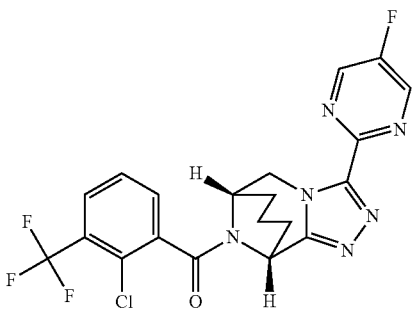 [SMILES: O=C(c1cccc(C(F)(F)F)c1Cl)N1[C@H]2CCC[C@@H]1c1nnc(-c3ncc(F)cn3)n1C2]

The title compound, absolute configuration unknown, was obtained as a single enantiomer by Chiral SFC purification of Example 16 performed using a CHIRALPAK AD-H (250×20 mm) column and a mobile phase of 60% $CO_2$, 40% mixture of EtOH/iPrOH 50/50 (v/v). The enantiomeric purity was confirmed by analytical SFC using a CHIRALPAK AD-H (250×4.6 mm) column and a mobile phase of 60% $CO_2$, 20% EtOH, 20% iPrOH containing 0.3% $iPrNH_2$ over 7 minutes. (100% single enantiomer, 2.41 min retention time). MS (ESI): mass calcd. $C_{20}H_{15}ClF_4N_6O$, 466.09; m/z found, 466.8 $[M+H]^+$.

Example 18: (6R*,10S*)-11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine

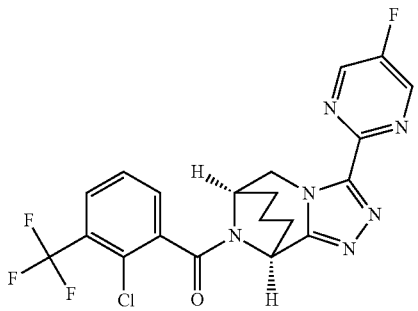 [SMILES: O=C(c1cccc(C(F)(F)F)c1Cl)N1[C@@H]2CCC[C@H]1c1nnc(-c3ncc(F)cn3)n1C2]

The title compound, absolute configuration unknown, was obtained as a single enantiomer by Chiral SFC purification of Example 16 performed using a CHIRALPAK AD-H (250×20 mm) column and a mobile phase of 60% $CO_2$, 40% mixture of EtOH/iPrOH 50/50 (v/v). The enantiomeric purity was confirmed by analytical SFC using a CHIRALPAK AD-H (250×4.6 mm) column and a mobile phase of 60% $CO_2$, 20% EtOH, 20% iPrOH containing 0.3% $iPrNH_2$ over 7 minutes. (100% single enantiomer, 2.96 min retention time). MS (ESI): mass calcd. $C_{20}H_{15}ClF_4N_6O$, 466.09; m/z found, 466.8 [M+H]$^+$.

Example 19: 11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine

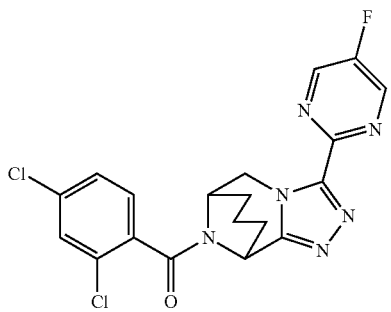 [SMILES: O=C(c1ccc(Cl)cc1Cl)N1C2CCCC1c1nnc(-c3ncc(F)cn3)n1C2]

The title compound was prepared in a manner analogous to Example 1 substituting Intermediate F for Intermediate D, in Example 1 step a, and substituting 2,4 dichlorobenzoyl chloride for Intermediate E in Example 1 step c. MS (ESI): mass calcd. $C_{19}H_{15}Cl_2FN_6O$, 432.07; m/z found, 433.1 [M+H]$^+$.

Example 20: (6S*,10R*)-11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine

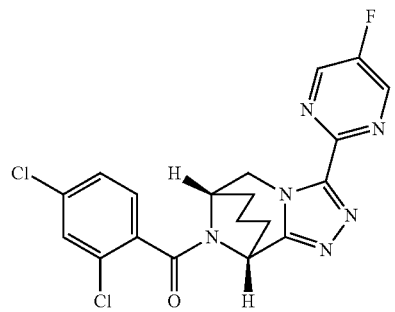 [SMILES: O=C(c1ccc(Cl)cc1Cl)N1[C@H]2CCC[C@@H]1c1nnc(-c3ncc(F)cn3)n1C2]

The title compound, absolute configuration unknown, was obtained as a single enantiomer by Chiral SFC purification of Example 19 performed using a CHIRALPAK AD-H (250×20 mm) column and a mobile phase of 60% $CO_2$, 40% mixture of EtOH/iPrOH 50/50 (v/v) containing 0.3% $iPrNH_2$. The enantiomeric purity was confirmed by analytical SFC using a CHIRALPAK AD-H (250×4.6 mm) column and a mobile phase of 60% $CO_2$, 20% EtOH, 20% iPrOH containing 0.3% $iPrNH_2$ over 7 minutes. (100% single enantiomer, 3.70 min retention time). MS (ESI): mass calcd. $C_{19}H_{15}Cl_2FN_6O$, 432.07; m/z found, 432.8 [M+H]$^+$.

Example 21: (6R*,10S*)-11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine

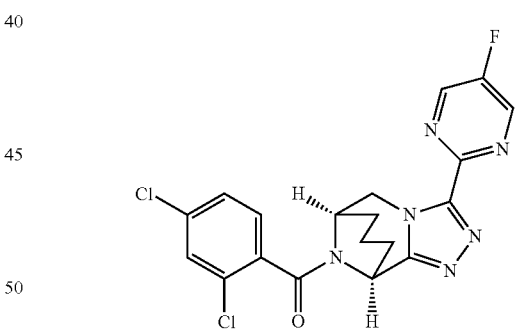

The title compound, absolute configuration unknown, was obtained as a single enantiomer by Chiral SFC purification of Example 19 performed using a CHIRALPAK AD-H (250×20 mm) column and a mobile phase of 60% $CO_2$, 40% mixture of EtOH/iPrOH 50/50 (v/v) containing 0.3% $iPrNH_2$. The enantiomeric purity was confirmed by analytical SFC using a CHIRALPAK AD-H (250×4.6 mm) column and a mobile phase of 60% $CO_2$, 20% EtOH, 20% iPrOH containing 0.3% $iPrNH_2$ over 7 minutes. (100% single enantiomer, 5.39 min retention time). MS (ESI): mass calcd. $C_{19}H_{15}Cl_2FN_6O$, 432.07; m/z found, 432.8 [M+H]$^+$. 1H NMR (400 MHz, CDCl$_3$): 8.83-8.71 (m, 2H), 7.55-7.28 (m, 2H), 7.22-6.99 (m, 1H), 6.46-5.42 (m, 1H), 5.12-4.03 (m, 3H), 2.25-1.74 (m, 5H), 1.43-1.24 (m, 1H).

Example 22: 11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine

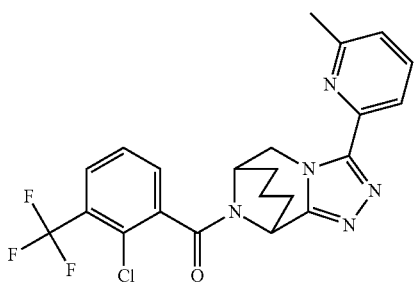 [SMILES: Cc1cccc(-c2nnc3n2CC2CCCC3N2C(=O)c2cccc(C(F)(F)F)c2Cl)n1]

The title compound was prepared in a manner analogous to Example 1 substituting Intermediate G for Intermediate D. MS (ESI): mass calcd. $C_{22}H_{19}ClF_3N_5O$, 461.12; m/z found, 462.1 $[M+H]^+$.

Example 23: (6S*,10R*)-11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine

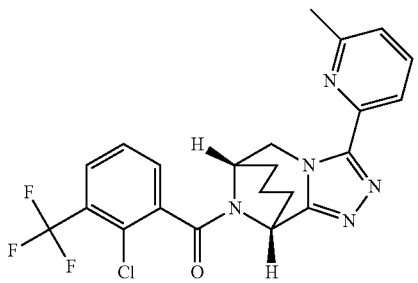 [SMILES: Cc1cccc(-c2nnc3n2C[C@@H]2CCC[C@H]3N2C(=O)c2cccc(C(F)(F)F)c2Cl)n1]

The title compound, absolute configuration unknown, was obtained as a single enantiomer by Chiral SFC purification of Example 22 performed using a CHIRALPAK AD-H (250×20 mm) column and a mobile phase of 75% $CO_2$, 25% iPrOH. The enantiomeric purity was confirmed by analytical SFC using a CHIRALPAK AD-H (250×4.6 mm) column and a mobile phase of 75% $CO_2$, 25% iPrOH containing 0.3% $iPrNH_2$ over 7 minutes. (100% single enantiomer, 3.95 min retention time). MS (ESI): mass calcd. $C_{22}H_{19}ClF_3N_5O$, 461.12; m/z found, 461.8 $[M+H]^+$. 1H NMR (500 MHz, CDCl$_3$): 8.22-8.11 (m, 1H), 7.83-7.76 (m, 1H), 7.76-7.69 (m, 1H), 7.61-7.27 (m, 2H), 7.25-7.16 (m, 1H), 6.45-5.43 (m, 1H), 5.06-4.00 (m, 3H), 2.65-2.50 (m, 3H), 2.24-1.72 (m, 5H), 1.45-1.31 (m, 1H).

Example 24: (6R*,10S*)-11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine

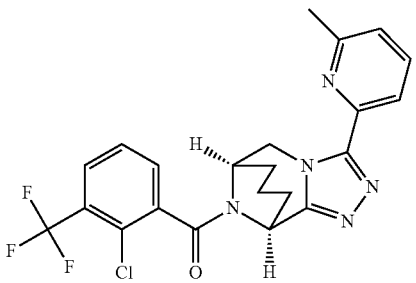 [SMILES: Cc1cccc(-c2nnc3n2C[C@H]2CCC[C@@H]3N2C(=O)c2cccc(C(F)(F)F)c2Cl)n1]

The title compound, absolute configuration unknown, was obtained as a single enantiomer by Chiral SFC purification of Example 22 performed using a CHIRALPAK AD-H (250×20 mm) column and a mobile phase of 75% $CO_2$, 25% iPrOH. The enantiomeric purity was confirmed by analytical SFC using a CHIRALPAK AD-H (250×4.6 mm) column and a mobile phase of 75% $CO_2$, 25% iPrOH containing 0.3% $iPrNH_2$ over 7 minutes. (100% single enantiomer, 4.87 min retention time). MS (ESI): mass calcd. $C_{22}H_{19}ClF_3N_5O$, 461.12; m/z found, 461.8 $[M+H]^+$.

Example 25: 11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine

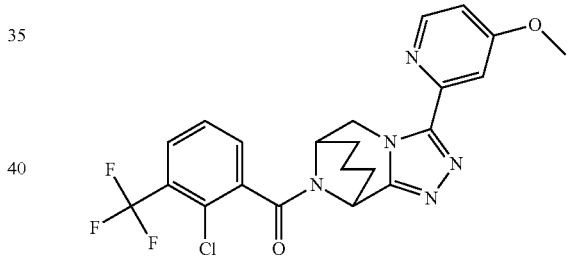

The title compound was prepared in a manner analogous to Example 1 substituting 4-methoxy-pyridine-2-carboxylic acid hydrazide for Intermediate D. MS (ESI): mass calcd. $C_{22}H_{19}ClF_3N_5O_2$, 477.12; m/z found, 478.1 $[M+H]^+$.

Example 26: (6S*,10R*)-11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine

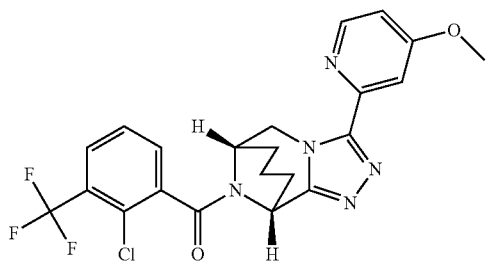 [SMILES: COc1ccnc(-c2nnc3n2C[C@@H]2CCC[C@H]3N2C(=O)c2cccc(C(F)(F)F)c2Cl)c1]

The title compound, absolute configuration unknown, was obtained as a single enantiomer by Chiral SFC purification of Example 25 performed using a CHIRALCEL OD-H (250×20 mm) column and a mobile phase of 80% $CO_2$, 20% MeOH. The enantiomeric purity was confirmed by analytical SFC using a CHIRALCEL OD-H (250×4.6 mm) and a mobile phase of 75% $CO_2$, 25% MeOH containing 0.3% $iPrNH_2$ over 7 minutes. (100% single enantiomer, 3.30 min retention time). MS (ESI): mass calcd. $C_{22}H_{19}ClF_3N_5O_2$, 477.12; m/z found, 477.8 $[M+H]^+$.

Example 27: (6R*,10S*)-11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine

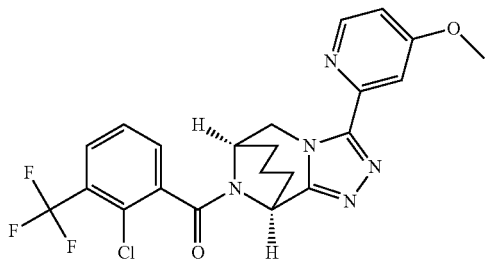 [SMILES: COc1ccnc(-c2nnc3n2C[C@H]2CCC[C@@H]3N2C(=O)c2cccc(C(F)(F)F)c2Cl)c1]

The title compound, absolute configuration unknown, was obtained as a single enantiomer by Chiral SFC purification of Example 25 performed using a CHIRALCEL OD-H (250×20 mm) column and a mobile phase of 80% $CO_2$, 20% MeOH. The enantiomeric purity was confirmed by analytical SFC using a CHIRALCEL OD-H (250×4.6 mm) and a mobile phase of 75% $CO_2$, 25% MeOH containing 0.3% $iPrNH_2$ over 7 minutes. (98.9% single enantiomer, 4.04 min retention time). MS (ESI): mass calcd. $C_{22}H_{19}ClF_3N_5O_2$, 477.12; m/z found, 477.8 $[M+H]^+$. 1H NMR (400 MHz, $CDCl_3$): 8.48-8.31 (m, 1H), 7.95-7.85 (m, 1H), 7.84-7.75 (m, 1H), 7.62-7.25 (m, 2H), 6.93-6.83 (m, 1H), 6.46-5.41 (m, 1H), 5.07-3.96 (m, 3H), 3.97-3.90 (m, 3H), 2.26-1.72 (m, 5H), 1.47-1.29 (m, 1H).

Example 28: 3-(5-Chloropyridin-2-yl)-1-{[2-chloro-3-(trifluoromethyl)phenyl]carbonyl}-5,6,7,8,9,10-hexahydro-6,10-epimino[1,2,4]triazolo[4,3-a]azocine

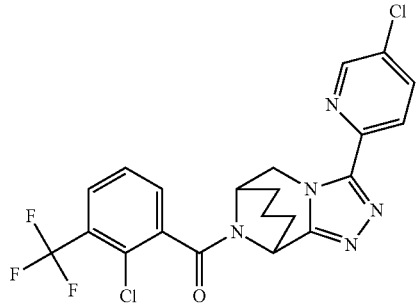 [SMILES: O=C(c1cccc(C(F)(F)F)c1Cl)N1C2CCCC1c1nnc(-c3ccc(Cl)cn3)n1C2]

The title compound was prepared in a manner analogous to Example 1 substituting 5-chloro-2-pyridinecarbohydrazide for Intermediate D. MS (ESI): mass calcd. $C_{21}H_{16}Cl_2F_3N_5O$, 481.07; m/z found, 482.1 $[M+H]^+$.

Example 29: (6S*,10R*)-3-(5-Chloropyridin-2-yl)-1-{[2-chloro-3-(trifluoromethyl)phenyl]carbonyl}-5,6,7,8,9,10-hexahydro-6,10-epimino[1,2,4]triazolo[4,3-a]azocine

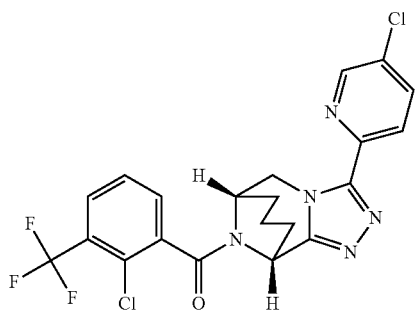

The title compound, absolute configuration unknown, was obtained as a single enantiomer by Chiral SFC purification of Example 28 performed using a CHIRALPAK AD-H (250×20 mm) column and a mobile phase of 60% $CO_2$, 40% EtOH. The enantiomeric purity was confirmed by analytical SFC using a CHIRALPAK AD-H (250×4.6 mm) column and a mobile phase of 60% $CO_2$, 40% EtOH containing 0.3% $iPrNH_2$ over 7 minutes. (100% single enantiomer, 2.51 min retention time). MS (ESI): mass calcd. $C_{21}H_{16}Cl_2F_3N_5O$, 481.07; m/z found, 481.7 $[M+H]^+$.

Example 30: (6R*,10S*)-3-(5-Chloropyridin-2-yl)-1-{[2-chloro-3-(trifluoromethyl)phenyl]carbonyl}-5,6,7,8,9,10-hexahydro-6,10-epimino[1,2,4]triazolo[4,3-a]azocine

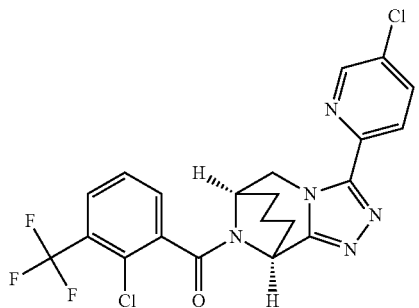 [SMILES: O=C(c1cccc(C(F)(F)F)c1Cl)N1[C@@H]2CCC[C@H]1c1nnc(-c3ccc(Cl)cn3)n1C2]

The title compound, absolute configuration unknown, was obtained as a single enantiomer by Chiral SFC purification of Example 28 performed using a CHIRALPAK AD-H (250×20 mm) column and a mobile phase of 60% $CO_2$, 40% EtOH. The enantiomeric purity was confirmed by analytical SFC using a CHIRALPAK AD-H (250×4.6 mm) column and a mobile phase of 60% $CO_2$, 40% EtOH containing 0.3% $iPrNH_2$ over 7 minutes. (100% single enantiomer, 3.59 min retention time). MS (ESI): mass calcd. $C_{21}H_{16}Cl_2F_3N_5O$, 481.07; m/z found, 481.7 $[M+H]^+$.

Example 31: 11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine

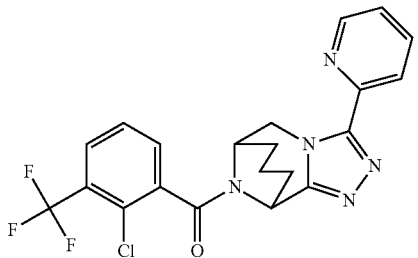 [SMILES: O=C(c1cccc(C(F)(F)F)c1Cl)N1C2CCCC1c1nnc(-c3ccccn3)n1C2]

The title compound was prepared in a manner analogous to Example 1 substituting 2-picolinyl hydrazide for Intermediate D. MS (ESI): mass calcd. $C_{21}H_{17}ClF_3N_5O$, 447.11; m/z found, 448.1 [M+H]$^+$.

Example 32: (6S*,10R*)-11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine

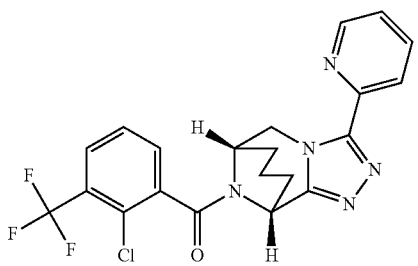

The title compound, absolute configuration unknown, was obtained as a single enantiomer by Chiral SFC purification of Example 31 performed using a CHIRALPAK AD-H (250×20 mm) column and a mobile phase of 75% CO$_2$, 25% EtOH. The enantiomeric purity was confirmed by analytical SFC using a CHIRALPAK AD-H (250×4.6 mm) column and a mobile phase of 75% CO$_2$, 25% EtOH containing 0.3% iPrNH$_2$ over 7 minutes. (100% single enantiomer, 4.05 min retention time). MS (ESI): mass calcd. $C_{21}H_{17}ClF_3N_5O$, 447.11; m/z found, 447.7 [M+H]$^+$. 1H NMR (500 MHz, CDCl$_3$): 8.69-8.55 (m, 1H), 8.42-8.32 (m, 1H), 7.88-7.77 (m, 2H), 7.60-7.27 (m, 3H), 6.45-5.43 (m, 1H), 5.06-3.98 (m, 3H), 2.23-1.96 (m, 3H), 1.92-1.73 (m, 2H), 1.47-1.32 (m, 1H).

Example 33: (6R*,10S*)-11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine

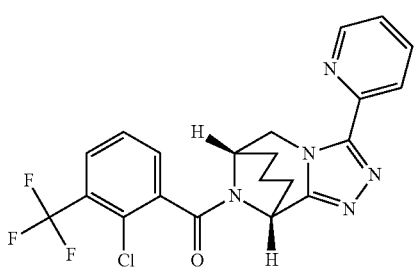

The title compound, absolute configuration unknown, was obtained as a single enantiomer by Chiral SFC purification of Example 31 performed using a CHIRALPAK AD-H (250×20 mm) column and a mobile phase of 75% CO$_2$, 25% EtOH. The enantiomeric purity was confirmed by analytical SFC using a CHIRALPAK AD-H (250×4.6 mm) and a mobile phase of 75% CO$_2$, 25% EtOH containing 0.3% iPrNH$_2$ over 7 minutes. (99.2% single enantiomer, 4.79 min retention time). MS (ESI): mass calcd. $C_{21}H_{17}ClF_3N_5O$, 447.11; m/z found, 447.7 [M+H]$^+$.

Example 34: 11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine

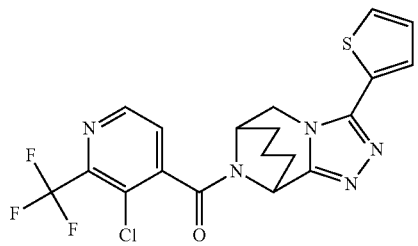 [SMILES: O=C(c1ccnc(C(F)(F)F)c1Cl)N1C2CCCC1c1nnc(-c3cccs3)n1C2]

Example 34, Step a: tert-butyl 3-(thiophen-2-yl)-5,6,7,8,9,10-hexahydro-6,10-epimino[1,2,4]triazolo[4,3-a]azocine-11-carboxylate To a round bottom flask was added Intermediate C (305 mg, 0.766 mmol), 2-thiophenecarboxylic acid hydrazide (122 mg, 0.843 mmol) and EtOH (3 mL). This heterogeneous mixture was stirred at room temperature for 60 h. To this suspension was added KOtBu (107 mg, 0.958 mmol). After 30 min at room temperature, the mixture was heated at 100° C. for 15 h. The mixture was concentrated in vacuo and chromatographed on SiO$_2$ eluting with EtOAc/Hex to afford the desired compound (204 mg, 77%). MS (ESI): mass calcd. $C_{17}H_{22}N_4O_2S$, 346.15; m/z found, 347.2 [M+H]$^+$. 1H NMR (500 MHz, CDCl$_3$): 7.55-7.45 (m, 2H), 7.18 (dd, J=5.1, 3.7 Hz, 1H), 5.79-5.54 (m, 1H), 4.98-4.71 (m, 1H), 4.43-4.32 (m, 1H), 4.09 (d, J=12.3 Hz, 1H), 2.05-1.88 (m, 3H), 1.80-1.65 (m, 2H), 1.48 (s, 9H), 1.30-1.18 (m, 1H).

Example 34, Step b: 3-(thiophen-2-yl)-5,6,7,8,9,10-hexahydro-6,10-epimino[1,2,4]triazolo[4,3-a]azocine To a solution of the product of Example 34, step a (201 mg, 0.582 mmol) in DCM (3 mL) was added TFA (1 mL). The mixture was stirred for 2 h at room temperature and then concentrated in vacuo. The residue was chromatographed on SiO$_2$ eluting with 2 M NH$_3$ in MeOH/DCM to afford the title compound as a colorless foam (140 mg, 98%). MS (ESI): mass calcd. $C_{12}H_{14}N_4S$, 246.09; m/z found, 247.1 [M+H]$^+$. 1H NMR (500 MHz, CDCl$_3$): 7.53 (dd, J=3.7, 1.1 Hz, 1H), 7.48 (dd, J=5.1, 1.1 Hz, 1H), 7.17 (dd, J=5.1, 3.7 Hz, 1H), 4.58 (t, J=3.4 Hz, 1H), 4.36-4.29 (m, 1H), 4.10 (d, J=12.4 Hz, 1H), 3.76-3.70 (m, 1H), 2.08-1.95 (m, 3H), 1.75-1.63 (m, 2H), 1.29-1.16 (m, 1H).

Example 34, Step c: 11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine To a solution of the product of Example 34, step b (138 mg, 0.560 mmol) in DCM (6 mL) was added 3-chloro-2-(trifluoromethyl)-4-pyridinecarboxylic acid (139 mg, 0.616 mmol) followed by HOBt (53 mg, 0.392 mmol), EDCl (161 mg, 0.840 mmol) and TEA (0.16 mL, 0.320 mmol). The reaction was stirred at room temperature overnight and then loaded directly on a $SiO_2$ column eluting with EtOAc/Hex to afford the title compound (202 mg, 79%). MS (ESI): mass calcd. $C_{19}H_{15}ClF_3N_5OS$, 453.06; m/z found, 454.1 $[M+H]^+$.

Example 35: (6S*,10R*)-11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine

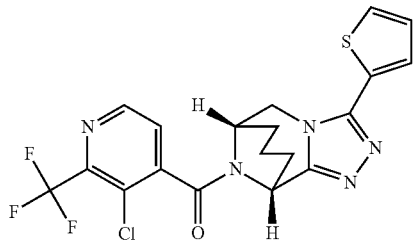 [SMILES: O=C(c1ccnc(C(F)(F)F)c1Cl)N1[C@H]2CCC[C@@H]1c1nnc(-c3cccs3)n1C2]

The title compound, absolute configuration unknown, was obtained as a single enantiomer by Chiral SFC purification of Example 34 performed using a CHIRALPAK AD-H (250×20 mm) column and a mobile phase of 70% $CO_2$, 30% EtOH. The enantiomeric purity was confirmed by analytical SFC using a CHIRALPAK AD-H (250×4.6 mm) column and a mobile phase of 70% $CO_2$, 30% EtOH containing 0.3% $iPrNH_2$ over 7 minutes. (100% single enantiomer, 3.55 min retention time). MS (ESI): mass calcd. $C_{19}H_{15}ClF_3N_5OS$, 453.06; m/z found, 453.7 $[M+H]^+$.

Example 36: (6R*,10S*)-11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine

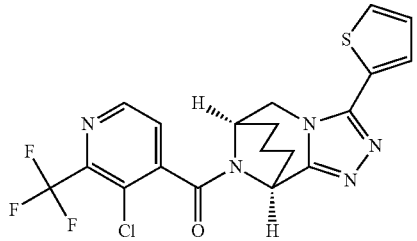 [SMILES: O=C(c1ccnc(C(F)(F)F)c1Cl)N1[C@@H]2CCC[C@H]1c1nnc(-c3cccs3)n1C2]

The title compound, absolute configuration unknown, was obtained as a single enantiomer by Chiral SFC purification of Example 34 performed using a CHIRALPAK AD-H (250×20 mm) column and a mobile phase of 70% $CO_2$, 30% EtOH. The enantiomeric purity was confirmed by analytical SFC using a CHIRALPAK AD-H (250×4.6 mm) and a mobile phase of 70% $CO_2$, 30% EtOH containing 0.3% $iPrNH_2$ over 7 minutes. (100% single enantiomer, 4.44 min retention time). MS (ESI): mass calcd. $C_{19}H_{15}ClF_3N_5OS$, 453.06; m/z found, 453.7 $[M+H]^+$. 1H NMR (500 MHz, CDCl3): 8.75-8.60 (m, 1H), 7.59-7.45 (m, 3H), 7.24-7.12 (m, 1H), 5.53-5.46 (m, 1H), 4.95 (s, 1H), 4.60-4.47 (m, 1H), 4.31-3.98 (m, 1H), 2.24-1.77 (m, 5H), 1.44-1.29 (m, 1H).

Example 37: 11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine

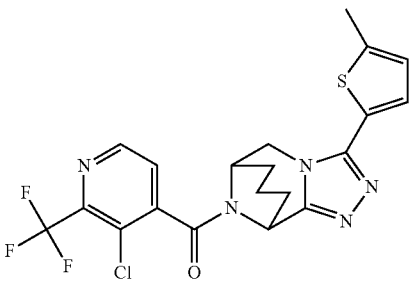 [SMILES: Cc1ccc(-c2nnc3n2CC2CCCC3N2C(=O)c2ccnc(C(F)(F)F)c2Cl)s1]

The title compound was prepared in a manner analogous to Example 34 substituting 5-methyl-2-thiophenecarboxylic acid hydrazide for 2-thiophenecarboxylic acid hydrazide. MS (ESI): mass calcd. $C_{20}H_{17}ClF_3N_5OS$, 467.08; m/z found, 468.1 $[M+H]^+$.

Example 38: (6S*,10R*)-11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine

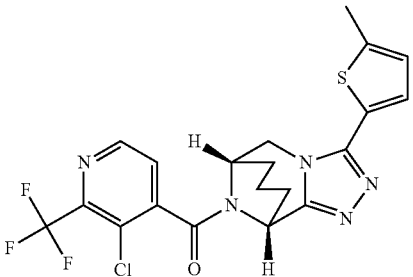 [SMILES: Cc1ccc(-c2nnc3n2C[C@@H]2CCC[C@H]3N2C(=O)c2ccnc(C(F)(F)F)c2Cl)s1]

The title compound, absolute configuration unknown, was obtained as a single enantiomer by Chiral SFC purification of Example 37 performed using a CHIRALPAK AD-H (250×20 mm) column and a mobile phase of 65% $CO_2$, 35% EtOH containing 0.3% $iPrNH_2$. The enantiomeric purity was confirmed by analytical SFC using a CHIRALPAK AD-H (250×4.6 mm) column and a mobile phase of 70% $CO_2$, 30% EtOH containing 0.3% $iPrNH_2$ over 7 minutes. (100% single enantiomer, 3.41 min retention time). MS (ESI): mass calcd. $C_{20}H_{17}ClF_3N_5OS$, 467.08; m/z found, 467.7 $[M+H]^+$.

Example 39: (6R*,10S*)-11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine

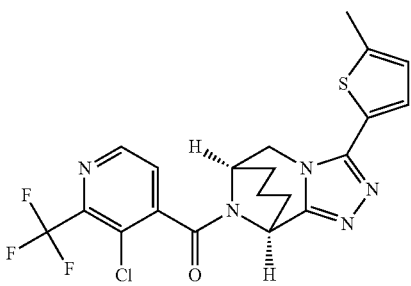 [SMILES: Cc1ccc(-c2nnc3n2C[C@H]2CCC[C@@H]3N2C(=O)c2ccnc(C(F)(F)F)c2Cl)s1]

The title compound, absolute configuration unknown, was obtained as a single enantiomer by Chiral SFC purification of Example 37 performed using a CHIRALPAK AD-H (250×20 mm) column and a mobile phase of 65% $CO_2$, 35% EtOH containing 0.3% $iPrNH_2$. The enantiomeric purity was confirmed by analytical SFC using a CHIRALPAK AD-H (250×4.6 mm) column and a mobile phase of 70% $CO_2$, 30% EtOH containing 0.3% $iPrNH_2$ over 7 minutes. (100% single enantiomer, 4.99 min retention time). MS (ESI): mass calcd. $C_{20}H_{17}ClF_3N_5OS$, 467.08; m/z found, 467.7 $[M+H]^+$.

Example 40: (6S,9R)-10-{[2-Chloro-3-(trifluoromethyl)phenyl]carbonyl}-3-(4-fluorophenyl)-6,7,8,9-tetrahydro-5H-6,9-epimino[1,2,4]triazolo[4,3-a]azepine

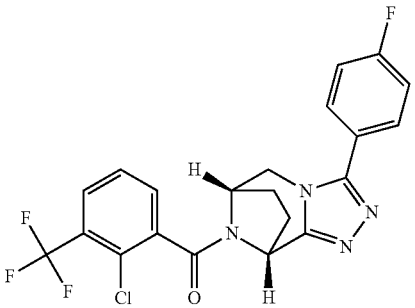 [SMILES: O=C(c1cccc(C(F)(F)F)c1Cl)N1[C@H]2CC[C@@H]1c1nnc(-c3ccc(F)cc3)n1C2]

Example 40, Step a: (6S,9R)-tert-butyl-3-(4-fluorophenyl)-6,7,8,9-tetrahydro-5H-6,9-epimino[1,2,4]triazolo[4,3-a]azepine-10-carboxylate To a round bottom flask was added Intermediate I (120 mg, 0.494 mmol), 4-fluorobenzohydrazide (119 mg, 0.742 mmol) and n-BuOH (2 mL). The mixture was heated at 140° C. for 72 h and then concentrated in vacuo and taken on to the next step without further purification. MS (ESI): mass calcd. $C_{18}H_{21}FN_4O_2$, 344.16; m/z found, 345.2 $[M+H]^+$.

Example 40, Step b: (6S,9R)-3-(4-fluorophenyl)-6,7,8,9-tetrahydro-5H-6,9-epimino[1,2,4]triazolo[4,3-a]azepine To a solution of the product of Example 40, step a (170 mg, 0.494 mmol) in DCM (5 mL) was added TFA (2 mL). The mixture was stirred for 2 h at room temperature and then concentrated in vacuo. The residue was chromatographed on $SiO_2$ eluting with 2 M $NH_3$ in MeOH/DCM to afford the title compound as a white solid (114 mg, 94%). MS (ESI): mass calcd. $C_{13}H_{13}FN_4$, 244.11; m/z found, 245.1 $[M+H]^+$. 1H NMR (500 MHz, $CDCl_3$): 7.74-7.67 (m, 2H), 7.21-7.14 (m, 2H), 4.81-4.77 (m, 1H), 4.24-4.18 (m, 1H), 4.09-4.04 (m, 1H), 3.85-3.81 (m, 1H), 2.28-2.10 (m, 3H), 1.72-1.65 (m, 1H).

Example 40, Step c: (6S,9R)-10-{[2-Chloro-3-(trifluoromethyl)phenyl]carbonyl}-3-(4-fluorophenyl)-6,7,8,9-tetrahydro-5H-6,9-epimino[1,2,4]triazolo[4,3-a]azepine To a solution of the product of Example 40, step b (111 mg, 0.453 mmol) in DCM (3 mL) was added Intermediate E (116 mg, 0.476 mmol) followed by TEA (0.08 mL, 0.544 mmol). The reaction was stirred at room temperature overnight and then loaded directly on a $SiO_2$ column eluting with EtOAc/Hex to afford the title compound (186 mg, 91%). MS (ESI): mass calcd. $C_{21}H_{15}ClF_4N_4O$, 450.09; m/z found, 451.1 $[M+H]^+$. 1H NMR (500 MHz, $CDCl_3$): 7.86-7.29 (m, 5H), 7.26-7.14 (m, 2H), 5.43-5.32 (m, 1H), 5.02-4.92 (m, 1H), 4.71-4.55 (m, 1H), 4.07-3.79 (m, 1H), 2.60-2.18 (m, 3H), 1.92-1.77 (m, 1H).

Example 41: (6S,9R)-10-{[2-Chloro-3-(trifluoromethyl)phenyl]carbonyl}-3-pyridin-2-yl-6,7,8,9-tetrahydro-5H-6,9-epimino[1,2,4]triazolo[4,3-a]azepine

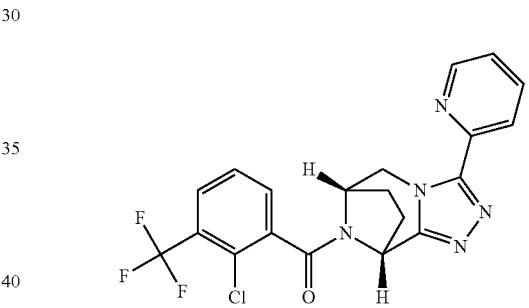

The title compound was prepared in a manner analogous to Example 40 substituting 2-picolinyl hydrazide for 4-fluorobenzohydrazide. MS (ESI): mass calcd. $C_{20}H_{15}ClF_3N_5O$, 433.09; m/z found, 434.1 $[M+H]^+$. 1H NMR (500 MHz, $CDCl_3$): 8.68-8.51 (m, 1H), 8.40-8.29 (m, 1H), 7.88-7.75 (m, 2H), 7.56-7.27 (m, 3H), 5.43-5.31 (m, 1H), 5.03-4.49 (m, 3H), 2.60-2.19 (m, 3H), 2.01-1.85 (m, 1H).

Example 42: (6S,9R)-10-{[2-Chloro-3-(trifluoromethyl)phenyl]carbonyl}-3-pyrazin-2-yl-6,7,8,9-tetrahydro-5H-6,9-epimino[1,2,4]triazolo[4,3-a]azepine

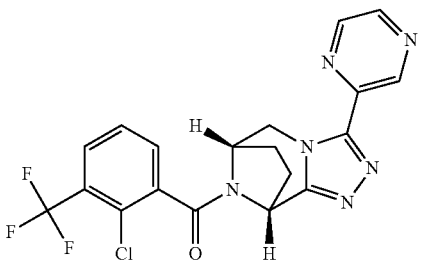 [SMILES: O=C(c1cccc(C(F)(F)F)c1Cl)N1[C@H]2CC[C@@H]1c1nnc(-c3cnccn3)n1C2]

The title compound was prepared in a manner analogous to Example 40 substituting 2-pyrazinecarbohydrazide for 4-fluorobenzohydrazide. MS (ESI): mass calcd. $C_{19}H_{14}ClF_3N_6O$, 434.09; m/z found, 435.1 [M+H]$^+$. 1H NMR (500 MHz, CDCl$_3$): 9.67-9.53 (m, 1H), 8.69-8.46 (m, 2H), 7.85-7.75 (m, 1H), 7.60-7.27 (m, 2H), 5.44-5.31 (m, 1H), 5.04-4.45 (m, 3H), 2.62-2.20 (m, 3H), 2.01-1.86 (m, 1H).

Example 43: (6S,9R)-10-{[2-Chloro-4-fluoro-3-(trifluoromethyl)phenyl]carbonyl}-3-pyridin-2-yl-6,7,8,9-tetrahydro-5H-6,9-epimino[1,2,4]triazolo[4,3-a]azepine

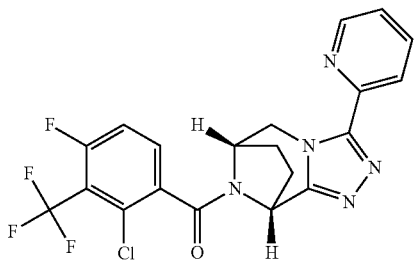 [SMILES: O=C(c1ccc(F)c(C(F)(F)F)c1Cl)N1[C@H]2CC[C@@H]1c1nnc(-c3ccccn3)n1C2]

Example 43, Step a: (6S,9R)-tert-butyl 3-(pyridin-2-yl)-6,7,8,9-tetrahydro-5H-6,9-epimino[1,2,4]triazolo[4,3-a]azepine-10-carboxylate The title compound was prepared in a manner analogous to Example 40 step a, substituting 2-picolinyl hydrazide for 4-fluorobenzohydrazide. MS (ESI): mass calcd. $C_{17}H_{21}N_5O_2$, 327.17; m/z found, 328.2 [M+H]$^+$.

Example 43, Step b: (6S,9R)-3-(pyridin-2-yl)-6,7,8,9-tetrahydro-5H-6,9-epimino[1,2,4]triazolo[4,3-a]azepine The title compound was prepared in a manner analogous to Example 40 step b, substituting the product of Example 43 step a, for the product of Example 40, step a. MS (ESI): mass calcd. $C_{12}H_{13}N_5$, 227.12; m/z found, 228.1 [M+H]$^+$. 1H NMR (500 MHz, CDCl$_3$): 8.61-8.56 (m, 1H), 8.31-8.24 (m, 1H), 7.82-7.75 (m, 1H), 7.33-7.27 (m, 1H), 4.86-4.78 (m, 1H), 4.56-4.45 (m, 2H), 4.13-4.04 (m, 1H), 2.32-2.12 (m, 3H), 1.82-1.73 (m, 1H).

Example 43, Step c: (6S,9R)-10-{[2-Chloro-4-fluoro-3-(trifluoromethyl)phenyl]carbonyl}-3-pyridin-2-yl-6,7,8,9-tetrahydro-5H-6,9-epimino[1,2,4]triazolo[4,3-a]azepine The title compound was prepared in a manner analogous to Example 34 step c, substituting the product of Example 43 step b, for the product of Example 34 step b, and 2-chloro-4-fluoro-3-(trifluoromethyl)benzoic acid for 3-chloro-2-(trifluoromethyl)-4-pyridinecarboxylic acid. MS (ESI): mass calcd. $C_{20}H_{14}ClF_4N_5O$, 451.08; m/z found, 452.1 [M+H]$^+$. 1H NMR (500 MHz, CDCl$_3$): 8.67-8.52 (m, 1H), 8.39-8.29 (m, 1H), 7.89-7.78 (m, 1H), 7.55-7.28 (m, 2H), 7.25-7.10 (m, 1H), 5.39-5.27 (m, 1H), 5.01-4.54 (m, 3H), 2.58-2.20 (m, 3H), 2.02-1.88 (m, 1H).

Example 44: (6S,9R)-10-{[2-Methyl-3-(trifluoromethyl)phenyl]carbonyl}-3-pyridin-2-yl-6,7,8,9-tetrahydro-5H-6,9-epimino[1,2,4]triazolo[4,3-a]azepine

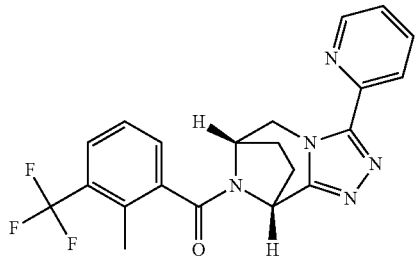

The title compound was prepared in a manner analogous to Example 43 substituting 2-methyl-3-(trifluoromethyl)benzoic acid for and 2-chloro-4-fluoro-3-(trifluoromethyl)benzoic acid. MS (ESI): mass calcd. $C_{21}H_{18}F_3N_5O$, 413.15; m/z found, 414.2 [M+H]$^+$. 1H NMR (500 MHz, CDCl$_3$) δ 8.68-8.53 (m, 1H), 8.41-8.31 (m, 1H), 7.88-7.81 (m, 1H), 7.75-7.67 (m, 1H), 7.45-7.29 (m, 3H), 6.22 (s, 0.2H), 5.44-5.31 (m, 0.8H), 5.02-4.92 (m, 0.8H), 4.86-4.79 (m, 0.8H), 4.79-4.72 (m, 0.8H), 4.61-4.54 (m, 0.2H), 4.39-4.32 (m, 0.2H), 4.21-4.13 (m, 0.2H), 2.69-1.79 (m, 7H).

Example 45: (6S,9R)-10-{[2-Chloro-3-(trifluoromethyl)phenyl]carbonyl}-3-(5-fluoropyridin-2-yl)-6,7,8,9-tetrahydro-5H-6,9-epimino[1,2,4]triazolo[4,3-a]azepine

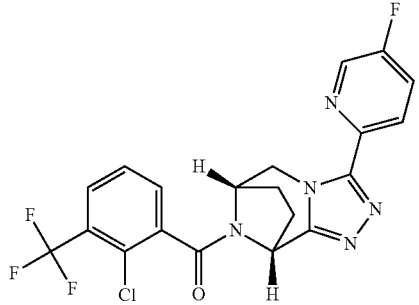 [SMILES: O=C(c1cccc(C(F)(F)F)c1Cl)N1[C@H]2CC[C@@H]1c1nnc(-c3ccc(F)cn3)n1C2]

The title compound was prepared in a manner analogous to Example 40 substituting 5-fluoro-pyridine-2-carboxylic acid hydrazide for 4-fluorobenzohydrazide. MS (ESI): mass calcd. $C_{20}H_{14}ClF_4N_5O$, 451.08; m/z found, 452.1 [M+H]$^+$. 1H NMR (500 MHz, CDCl$_3$): 8.56-8.31 (m, 2H), 7.84-7.74 (m, 1H), 7.60-7.28 (m, 3H), 6.24-6.18 (m, 0.25H), 5.43-5.31 (m, 0.75H), 5.03-4.16 (m, 3H), 2.60-2.19 (m, 3H), 2.01-1.85 (m, 1H).

Example 46: (6S,9R)-10-{[2-Chloro-3-(trifluoromethyl)phenyl]carbonyl}-3-pyrimidin-2-yl-6,7,8,9-tetrahydro-5H-6,9-epimino[1,2,4]triazolo[4,3-a]azepine

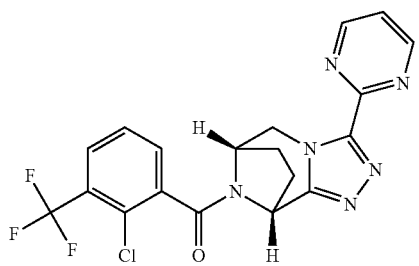 [SMILES: O=C(c1cccc(C(F)(F)F)c1Cl)N1[C@H]2CC[C@@H]1c1nnc(-c3ncccn3)n1C2]

The title compound was prepared in a manner analogous to Example 40 substituting Intermediate D for 4-fluorobenzohydrazide. MS (ESI): mass calcd. $C_{19}H_{14}ClF_3N_6O$, 434.09; m/z found, 435.1 [M+H]+. 1H NMR (500 MHz, CDCl3): 8.93-8.83 (m, 2H), 7.84-7.76 (m, 1H), 7.58-7.27 (m, 3H), 6.28-6.20 (m, 0.2H), 5.45-5.32 (m, 0.8H), 5.01-4.18 (m, 3H), 2.60-2.22 (m, 3H), 2.01-1.84 (m, 1H).

Example 47: (6S,9R)-10-[(2,3-Dichloro-4-fluorophenyl)carbonyl]-3-pyrazin-2-yl-6,7,8,9-tetrahydro-5H-6,9-epimino[1,2,4]triazolo[4,3-a]azepine

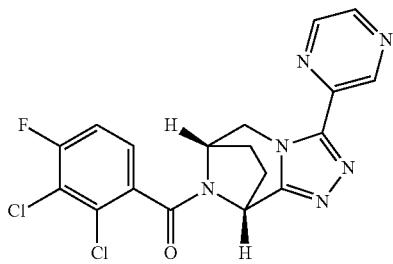 [SMILES: O=C(c1ccc(F)c(Cl)c1Cl)N1[C@H]2CC[C@@H]1c1nnc(-c3cnccn3)n1C2]

The title compound was prepared in a manner analogous to Example 43 substituting 2-pyrazinecarbohydrazide for 2-picolinyl hydrazide in Example 43 step a, and 2,3-dichloro-4-fluorobenzoic acid for 2-chloro-4-fluoro-3-(trifluoromethyl)benzoic acid in Example 43 step c. MS (ESI): mass calcd. $C_{18}H_{13}Cl_2FN_6O$, 418.05; m/z found, 419.1 [M+H]+. 1H NMR (500 MHz, CDCl3): 9.63-9.56 (m, 1H), 8.67-8.49 (m, 2H), 7.26-6.92 (m, 2H), 5.37-5.31 (m, 1H), 5.06-4.19 (m, 3H), 2.59-2.19 (m, 3H), 2.00-1.85 (m, 1H).

Example 48: (6S,9R)-10-{[2-Chloro-3-(trifluoromethyl)phenyl]carbonyl}-3-pyridin-3-yl-6,7,8,9-tetrahydro-5H-6,9-epimino[1,2,4]triazolo[4,3-a]azepine

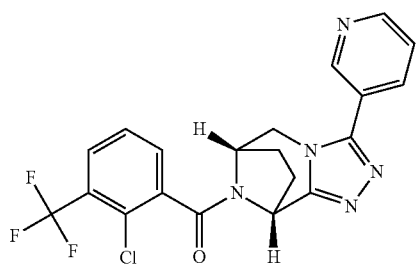

The title compound was prepared in a manner analogous to Example 40 substituting nicotinic acid hydrazide for 4-fluorobenzohydrazide. MS (ESI): mass calcd. $C_{20}H_{15}ClF_3N_5O$, 433.09; m/z found, 434.1 [M+H]+. 1H NMR (500 MHz, CDCl3): 9.04-8.86 (m, 1H), 8.82-8.70 (m, 1H), 8.19-8.07 (m, 1H), 7.86-7.77 (m, 1H), 7.60-7.31 (m, 3H), 5.49-5.31 (m, 1H), 5.06-3.86 (m, 3H), 2.65-2.20 (m, 3H), 1.94-1.77 (m, 1H).

Example 49: (6S,9R)-10-{[2-Chloro-3-(trifluoromethyl)phenyl]carbonyl}-3-(1,3-thiazol-4-yl)-6,7,8,9-tetrahydro-5H-6,9-epimino[1,2,4]triazolo[4,3-a]azepine

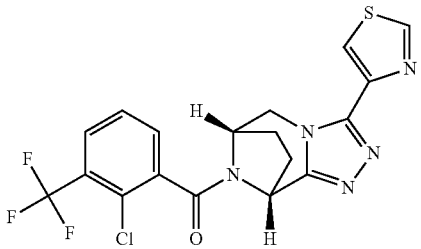 [SMILES: O=C(c1cccc(C(F)(F)F)c1Cl)N1[C@H]2CC[C@@H]1c1nnc(-c3cscn3)n1C2]

The title compound was prepared in a manner analogous to Example 40 substituting thiazole-4-carboxylic acid hydrazide for 4-fluorobenzohydrazide. MS (ESI): mass calcd. $C_{18}H_{13}ClF_3N_5OS$, 439.05; m/z found, 440.0 [M+H]+. 1H NMR (500 MHz, CDCl3): 8.96-8.80 (m, 1H), 8.29-8.23 (m, 1H), 7.83-7.76 (m, 1H), 7.55-7.27 (m, 2H), 5.42-5.31 (m, 1H), 4.99-4.16 (m, 3H), 2.59-2.19 (m, 3H), 2.01-1.85 (m, 1H).

Example 50: (6S,9R)-10-{[2-Chloro-3-(trifluoromethyl)phenyl]carbonyl}-3-(5-fluoropyrimidin-2-yl)-6,7,8,9-tetrahydro-5H-6,9-epimino[1,2,4]triazolo[4,3-a]azepine

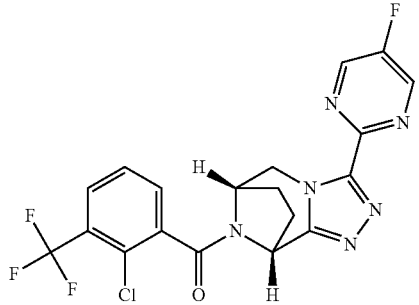

The title compound was prepared in a manner analogous to Example 40 substituting Intermediate F for 4-fluorobenzohydrazide. MS (ESI): mass calcd. $C_{19}H_{13}ClF_4N_6O$, 452.08; m/z found, 453.1 [M+H]+. 1H NMR (500 MHz, CDCl3): 8.81-8.69 (m, 2H), 7.84-7.76 (m, 1H), 7.57-7.27 (m, 2H), 5.43-5.33 (m, 1H), 5.02-4.18 (m, 3H), 2.63-2.21 (m, 3H), 2.00-1.84 (m, 1H).

Example 51: (6S,9R)-10-{[2-Chloro-3-(trifluoromethyl)phenyl]carbonyl}-3-(3-methyl-1H-pyrazol-5-yl)-6,7,8,9-tetrahydro-5H-6,9-epimino[1,2,4]triazolo[4,3-a]azepine

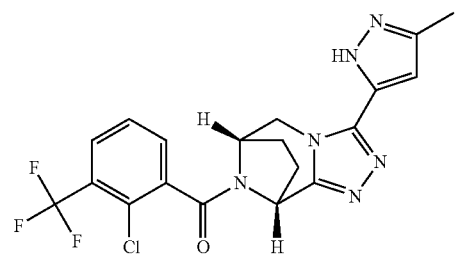 [SMILES: Cc1cc(-c2nnc3n2C[C@@H]2CC[C@H]3N2C(=O)c2cccc(C(F)(F)F)c2Cl)[nH]n1]

The title compound was prepared in a manner analogous to Example 40 substituting 3-methyl-1H-pyrazole-5-carbohydrazide for 4-fluorobenzohydrazide. MS (ESI): mass calcd. $C_{19}H_{16}ClF_3N_6O$, 436.10; m/z found, 437.1 [M+H]+. 1H NMR (500 MHz, CDCl$_3$): 7.82-7.75 (m, 1H), 7.56-7.27 (m, 2H), 6.77-6.71 (m, 1H), 5.44-5.32 (m, 1H), 5.00-4.90 (m, 1H), 4.75-4.08 (m, 2H), 2.59-2.18 (m, 6H), 2.01-1.83 (m, 1H).

Example 52: (6S,9R)-10-{[2-Chloro-4-fluoro-3-(trifluoromethyl)phenyl]carbonyl}-3-(1,3-thiazol-4-yl)-6,7,8,9-tetrahydro-5H-6,9-epimino[1,2,4]triazolo[4,3-a]azepine

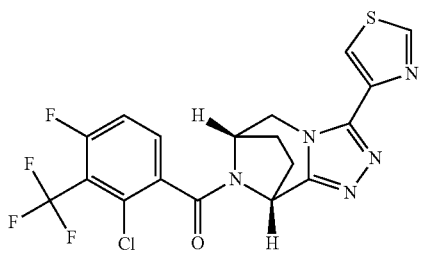 [SMILES: O=C(c1ccc(F)c(C(F)(F)F)c1Cl)N1[C@H]2CC[C@@H]1c1nnc(-c3cscn3)n1C2]

The title compound was prepared in a manner analogous to Example 43 substituting thiazole-4-carboxylic acid hydrazide for 2-picolinyl hydrazide in Example 43. MS (ESI): mass calcd. $C_{18}H_{12}ClF_4N_5OS$, 457.04; m/z found, 458.0 [M+H]+. 1H NMR (500 MHz, CDCl$_3$): 8.94-8.82 (m, 1H), 8.29-8.23 (m, 1H), 7.57-7.41 (m, 1H), 7.26-7.12 (m, 1H), 5.39-5.31 (m, 1H), 4.98-4.16 (m, 3H), 2.60-2.19 (m, 3H), 2.02-1.87 (m, 1H).

Example 53: (6S,9R)-10-{[2-Methyl-3-(trifluoromethyl)phenyl]carbonyl}-3-(1,3-thiazol-4-yl)-6,7,8,9-tetrahydro-5H-6,9-epimino[1,2,4]triazolo[4,3-a]azepine

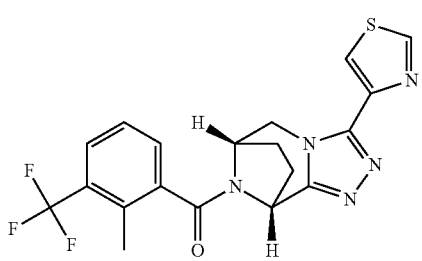 [SMILES: Cc1c(C(=O)N2[C@H]3CC[C@@H]2c2nnc(-c4cscn4)n2C3)cccc1C(F)(F)F]

The title compound was prepared in a manner analogous to Example 43 substituting thiazole-4-carboxylic acid hydrazide for 2-picolinyl hydrazide in Example 43 step a, and 2-methyl-3-(trifluoromethyl)benzoic acid for 2-chloro-4-fluoro-3-(trifluoromethyl)benzoic acid in Example 43, step c. MS (ESI): mass calcd. $C_{19}H_{16}F_3N_5OS$, 419.10; m/z found, 420.1 [M+H]+. 1H NMR (500 MHz, CDCl$_3$): 8.93-8.83 (m, 1H), 8.30-8.20 (m, 1H), 7.75-7.67 (m, 1H), 7.45-7.27 (m, 2H), 5.42-5.32 (m, 1H), 5.00-4.11 (m, 3H), 2.64-1.84 (m, 7H).

Example 54: (6S,9R)-10-[(2,4-Dichloro-3-fluorophenyl)carbonyl]-3-(1,3-thiazol-4-yl)-6,7,8,9-tetrahydro-5H-6,9-epimino[1,2,4]triazolo[4,3-a]azepine

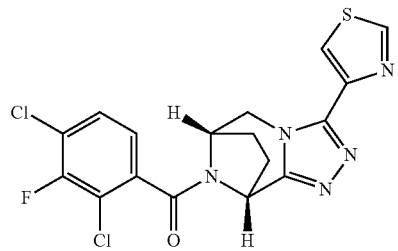 [SMILES: O=C(c1ccc(Cl)c(F)c1Cl)N1[C@H]2CC[C@@H]1c1nnc(-c3cscn3)n1C2]

The title compound was prepared in a manner analogous to Example 43 substituting thiazole-4-carboxylic acid hydrazide for 2-picolinyl hydrazide in Example 43 step a, and 2,4-dichloro-3-fluorobenzoic acid for 2-chloro-4-fluoro-3-(trifluoromethyl)benzoic acid in Example 43, step c. MS (ESI): mass calcd. $C_{17}H_{12}Cl_2FN_5OS$, 423.01; m/z found, 424.0 [M+H]+. 1H NMR (500 MHz, CDCl$_3$): 8.92-8.81 (m, 1H), 8.28-8.23 (m, 1H), 7.46-7.32 (m, 1H), 7.13-6.89 (m, 1H), 5.36-5.31 (m, 1H), 5.02-4.19 (m, 3H), 2.56-2.18 (m, 3H), 1.99-1.86 (m, 1H).

Example 55: (6S,9R)-3-(5-Chlorothiophen-2-yl)-10-{[2-chloro-3-(trifluoromethyl)phenyl]carbonyl}-6,7,8,9-tetrahydro-5H-6,9-epimino[1,2,4]triazolo[4,3-a]azepine

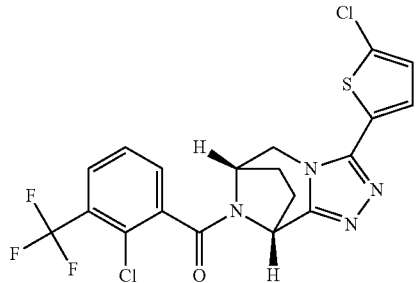 [SMILES: O=C(c1cccc(C(F)(F)F)c1Cl)N1[C@H]2CC[C@@H]1c1nnc(-c3ccc(Cl)s3)n1C2]

Example 55, Step a: tert-butyl (6S,9R)-3-(5-chlorothiophen-2-yl)-6,7,8,9-tetrahydro-5H-6,9-epimino[1,2,4]triazolo[4,3-a]azepine-10-carboxylate To a round bottom flask was added Intermediate J (258 mg, 0.673 mmol), 5-chloro-2-thiophenecarboxylic acid hydrazide (133 mg, 0.740 mmol) and n-BuOH (3 mL). This heterogeneous mixture was stirred at room temperature for 4 h. To this suspension was added KOtBu (94 mg, 0.841 mmol). After 30 min at room temperature, the mixture was heated at 100° C. for 15 h. The mixture was concentrated in vacuo and chromatographed on SiO$_2$ eluting with EtOAc/Hex to afford the desired compound (218 mg, 88%). MS (ESI): mass calcd. $C_{16}H_{19}ClN_4O_2S$, 366.09; m/z found, 367.1 [M+H]+. 1H NMR (500 MHz, CDCl$_3$): 7.20 (d, J=4.0 Hz, 1H), 6.97 (d, J=4.0 Hz, 1H), 5.51-5.40 (m, 1H), 4.85-4.72 (m, 1H), 4.45-4.30 (m, 1H), 3.94-3.86 (m, 1H), 2.44-2.35 (m, 1H), 2.31-2.22 (m, 1H), 2.17-2.09 (m, 1H), 1.78-1.70 (m, 1H), 1.44 (s, 9H).

Example 55, Step b: (6S,9R)-3-(5-Chlorothiophen-2-yl)-6,7,8,9-tetrahydro-5H-6,9-epimino[1,2,4]triazolo[4,3-a]azepine To a solution of the product of Example 55 step a (215 mg, 0.586 mmol) in DCM (3 mL) was added TFA (1 mL). The mixture was stirred for 2 h at room temperature and then concentrated in vacuo. The residue was chromatographed on SiO$_2$ eluting with 2 M NH$_3$ in MeOH/DCM to afford the title compound as a colorless foam (127 mg, 81%). MS (ESI): mass calcd. C$_{11}$H$_{11}$ClN$_4$S, 266.04; m/z found, 267.1 [M+H]$^+$. $^1$H NMR (500 MHz, CDCl$_3$): 7.16 (d, J=4.0 Hz, 1H), 6.93 (d, J=4.0 Hz, 1H), 4.76-4.72 (m, 1H), 4.22-4.16 (m, 1H), 4.11-4.06 (m, 1H), 3.92-3.87 (m, 1H), 2.30-2.09 (m, 3H), 1.74-1.66 (m, 2H).

Example 55, Step c: (6S,9R)-3-(5-Chlorothiophen-2-yl)-10-{[2-chloro-3-(trifluoromethyl)phenyl]carbonyl}-6,7,8,9-tetrahydro-5H-6,9-epimino[1,2,4]triazolo[4,3-a]azepine To a solution of the product of Example 55 step b (50 mg, 0.186 mmol) in DCM (2 mL) was added Intermediate E (47 mg, 0.195 mmol) followed by TEA (0.03 mL, 0.223 mmol). The reaction was stirred at room temperature overnight and then loaded directly on a SiO$_2$ column eluting with IPA/EtOAc to afford the title compound (82 mg, 93%). MS (ESI): mass calcd. C$_{19}$H$_{13}$Cl$_2$F$_3$N$_4$OS, 472.01; m/z found, 473.0 [M+H]$^+$. 1H NMR (500 MHz, CDCl$_3$): 7.84-7.77 (m, 1H), 7.58-7.27 (m, 2H), 7.25-7.15 (m, 1H), 7.03-6.93 (m, 1H), 5.44-5.34 (m, 1H), 5.00-3.90 (m, 3H), 2.64-2.19 (m, 3H), 1.97-1.83 (m, 1H).

Example 56: (6S,9R)-10-{[2-Chloro-3-(trifluoromethyl)phenyl]carbonyl}-3-(2-methyl-1,3-thiazol-4-yl)-6,7,8,9-tetrahydro-5H-6,9-epimino[1,2,4]triazolo[4,3-a]azepine

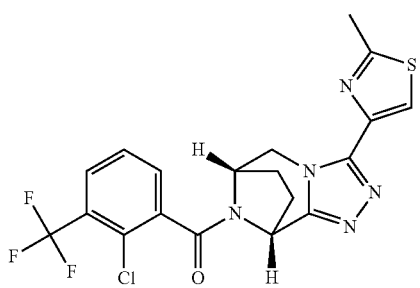 [SMILES: Cc1nc(-c2nnc3n2C[C@@H]2CC[C@H]3N2C(=O)c2cccc(C(F)(F)F)c2Cl)cs1]

The title compound was prepared in a manner analogous to Example 55 substituting 2-methyl-thiazole-4-carboxylic acid hydrazide for 5-chloro-2-thiophenecarboxylic acid hydrazide. MS (ESI): mass calcd. C$_{19}$H$_{15}$ClF$_3$N$_5$OS, 453.06; m/z found, 454.1 [M+H]$^+$. 1H NMR (500 MHz, CDCl$_3$): 8.04-7.98 (m, 1H), 7.83-7.76 (m, 1H), 7.56-7.27 (m, 2H), 5.40-4.15 (m, 4H), 2.81-2.67 (m, 3H), 2.59-2.17 (m, 3H), 2.01-1.85 (m, 1H).

Example 57: (6S,9R)-10-{[2-Chloro-3-(trifluoromethyl)phenyl]carbonyl}-3-(1,3-thiazol-5-yl)-6,7,8,9-tetrahydro-5H-6,9-epimino[1,2,4]triazolo[4,3-a]azepine

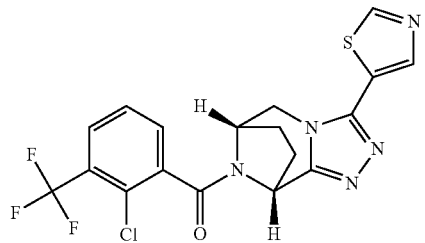 [SMILES: O=C(c1cccc(C(F)(F)F)c1Cl)N1[C@H]2CC[C@@H]1c1nnc(-c3cncs3)n1C2]

The title compound was prepared in a manner analogous to Example 55 substituting thiazole-5-carboxylic acid hydrazide for 5-chloro-2-thiophenecarboxylic acid hydrazide. MS (ESI): mass calcd. C$_{18}$H$_{13}$ClF$_3$N$_5$OS, 439.05; m/z found, 439.9 [M+H]$^+$. 1H NMR (500 MHz, CDCl$_3$): 8.99-8.90 (m, 1H), 8.31-8.13 (m, 1H), 7.86-7.77 (m, 1H), 7.57-7.28 (m, 2H), 5.47-3.95 (m, 4H), 2.65-2.21 (m, 3H), 1.99-1.84 (m, 1H).

Example 58: (6S,9R)-10-{[2-Chloro-3-(trifluoromethyl)phenyl]carbonyl}-3-thiophen-3-yl-6,7,8,9-tetrahydro-5H-6,9-epimino[1,2,4]triazolo[4,3-a]azepine

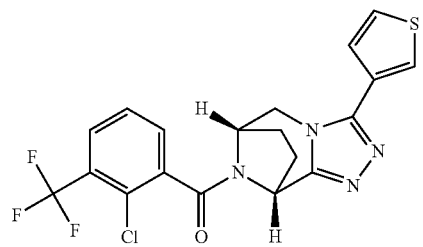 [SMILES: O=C(c1cccc(C(F)(F)F)c1Cl)N1[C@H]2CC[C@@H]1c1nnc(-c3ccsc3)n1C2]

The title compound was prepared in a manner analogous to Example 55 substituting 3-thiophenecarboxylic acid hydrazide for 5-chloro-2-thiophenecarboxylic acid hydrazide. MS (ESI): mass calcd. C$_{19}$H$_{14}$ClF$_3$N$_4$OS, 438.05; m/z found, 438.9 [M+H]$^+$. 1H NMR (500 MHz, CDCl$_3$): 7.84-7.28 (m, 6H), 5.46-5.31 (m, 1H), 5.02-4.91 (m, 1H), 4.74-4.55 (m, 1H), 4.26-3.87 (m, 1H), 2.61-2.19 (m, 3H), 1.95-1.81 (m, 1H).

Example 59: (6S,9R)-10-{[2-Chloro-3-(trifluoromethyl)phenyl]carbonyl}-3-(4-methyl-1,3-thiazol-5-yl)-6,7,8,9-tetrahydro-5H-6,9-epimino[1,2,4]triazolo[4,3-a]azepine

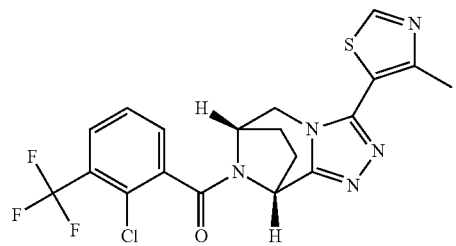 [SMILES: Cc1ncsc1-c1nnc2n1C[C@@H]1CC[C@H]2N1C(=O)c1cccc(C(F)(F)F)c1Cl]

The title compound was prepared in a manner analogous to Example 55 substituting 3-methylthiazole-5-carboxylic acid hydrazide for 5-chloro-2-thiophenecarboxylic acid hydrazide. MS (ESI): mass calcd. $C_{19}H_{15}ClF_3N_5OS$, 453.06; m/z found, 453.9 [M+H]$^+$. 1H NMR (500 MHz, CDCl$_3$): 8.95-8.83 (m, 1H), 7.85-7.78 (m, 1H), 7.56-7.29 (m, 2H), 5.44-5.29 (m, 1H), 5.05-4.89 (m, 1H), 4.53-4.18 (m, 1H), 4.00-3.82 (m, 1H), 2.70 (br s, 3H), 2.61-2.21 (m, 3H), 1.95-1.80 (m, 1H).

Example 60: (6S,9R)-3-(5-Chlorothiophen-2-yl)-10-{[3-chloro-2-(trifluoromethyl)pyridin-4-yl]carbonyl}-6,7,8,9-tetrahydro-5H-6,9-epimino[1,2,4]triazolo[4,3-a]azepine

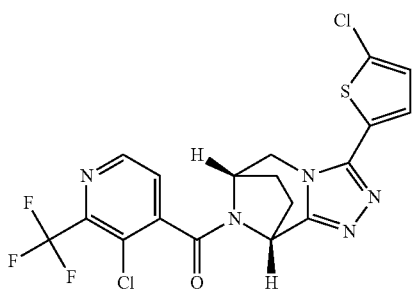 [SMILES: O=C(c1ccnc(C(F)(F)F)c1Cl)N1[C@H]2CC[C@@H]1c1nnc(-c3ccc(Cl)s3)n1C2]

To a solution of (6S,9R)-3-(5-chlorothiophen-2-yl)-6,7,8,9-tetrahydro-5H-6,9-epimino[1,2,4]triazolo[4,3-a]azepine (Example 55, step b)(35 mg, 0.132 mmol) in DCM (2 mL) was added 3-chloro-2-(trifluoromethyl)-4-pyridinecarboxylic acid (30 mg, 0.132 mmol) followed by HOBt (12 mg, 0.09 mmol), EDCl (38 mg, 0.197 mmol) and TEA (0.04 mL, 0.263 mmol). The reaction was stirred at room temperature overnight and then loaded directly on a SiO$_2$ column eluting with IPA/EtOAc to afford the title compound (53 mg, 85%). MS (ESI): mass calcd. $C_{18}H_{12}Cl_2F_3N_5OS$, 473.01; m/z found, 473.8 [M+H]$^+$. 1H NMR (500 MHz, CDCl$_3$): 8.75-8.59 (m, 1H), 7.68-7.30 (m, 1H), 7.26-7.13 (m, 1H), 7.03-6.92 (m, 1H), 5.46-5.31 (m, 1H), 4.98-4.87 (m, 1H), 4.65-4.50 (m, 1H), 4.25-3.94 (m, 1H), 2.63-2.23 (m, 3H), 2.00-1.86 (m, 1H).

Example 61: (6S,9R)-10-{[2-Chloro-3-(trifluoromethyl)phenyl]carbonyl}-3-thiophen-2-yl-6,7,8,9-tetrahydro-5H-6,9-epimino[1,2,4]triazolo[4,3-a]azepine

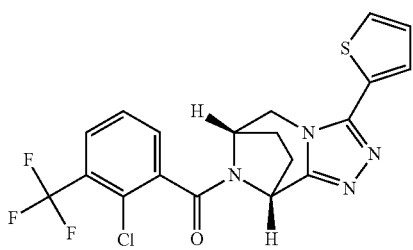 [SMILES: O=C(c1cccc(C(F)(F)F)c1Cl)N1[C@H]2CC[C@@H]1c1nnc(-c3cccs3)n1C2]

The title compound was prepared in a manner analogous to Example 55 substituting 2-thiophenecarboxylic acid hydrazide for 5-chloro-2-thiophenecarboxylic acid hydrazide. MS (ESI): mass calcd. $C_{19}H_{14}ClF_3N_4OS$, 438.05; m/z found, 438.9 [M+H]$^+$. 1H NMR (500 MHz, CDCl$_3$): 7.84-7.76 (m, 1H), 7.58-7.28 (m, 4H), 7.21-7.13 (m, 1H), 5.46-5.34 (m, 1H), 5.00-3.94 (m, 3H), 2.63-2.19 (m, 3H), 1.98-1.83 (m, 1H).

Example 62: (6S,9R)-10-{[2-Chloro-3-(trifluoromethyl)phenyl]carbonyl}-3-(1H-pyrrol-2-yl)-6,7,8,9-tetrahydro-5H-6,9-epimino[1,2,4]triazolo[4,3-a]azepine

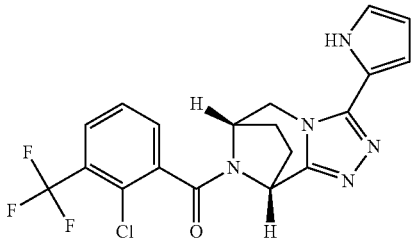 [SMILES: O=C(c1cccc(C(F)(F)F)c1Cl)N1[C@H]2CC[C@@H]1c1nnc(-c3ccc[nH]3)n1C2]

The title compound was prepared in a manner analogous to Example 55 substituting pyrrole-2-carboxylic acid hydrazide for 5-chloro-2-thiophenecarboxylic acid hydrazide. MS (ESI): mass calcd. $C_{19}H_{15}ClF_3N_5O$, 421.09; m/z found, 422.0 [M+H]$^+$. 1H NMR (500 MHz, CDCl$_3$): 11.05-10.57 (m, 1H), 7.84-7.74 (m, 1H), 7.59-7.27 (m, 2H), 7.08-7.02 (m, 1H), 6.57-6.13 (m, 2H), 5.47-3.80 (m, 4H), 2.62-2.14 (m, 3H), 2.00-1.81 (m, 1H).

Examples 63 to 192 are made in accordance with the synthetic schemes, and in light of the specific examples, provided above.

Example 63: (2-chloro-4-fluoro-3-(trifluoromethyl)phenyl)(3-(pyridin-2-yl)-5,6,7,8,9,10-hexahydro-6,10-epimino[1,2,4]triazolo[4,3-a]azocin-11-yl)methanone

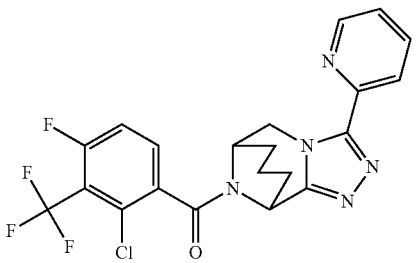 [SMILES: O=C(c1ccc(F)c(C(F)(F)F)c1Cl)N1C2CCCC1c1nnc(-c3ccccn3)n1C2]

Example 64: (2-fluoro-3-(trifluoromethyl)phenyl)(3-(pyridin-2-yl)-5,6,7,8,9,10-hexahydro-6,10-epimino[1,2,4]triazolo[4,3-a]azocin-11-yl)methanone

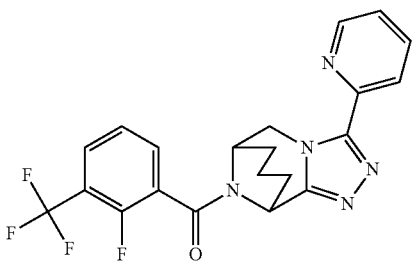 [SMILES: O=C(c1cccc(C(F)(F)F)c1F)N1C2CCCC1c1nnc(-c3ccccn3)n1C2]

Example 65: (3-chloro-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone

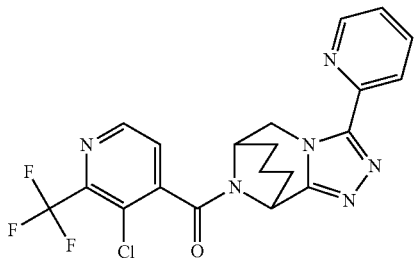 [SMILES: O=C(c1ccnc(C(F)(F)F)c1Cl)N1C2CCCC1c1nnc(-c3ccccn3)n1C2]

Example 66: ((2-methyl-3-(trifluoromethyl)phenyl)(3-(pyridin-2-yl)-5,6,7,8,9,10-hexahydro-6,10-epimino[1,2,4]triazolo[4,3-a]azocin-11-yl)methanone

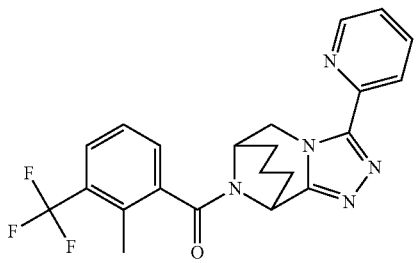 [SMILES: Cc1c(C(=O)N2C3CCCC2c2nnc(-c4ccccn4)n2C3)cccc1C(F)(F)F]

Example 67: (3-methyl-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone

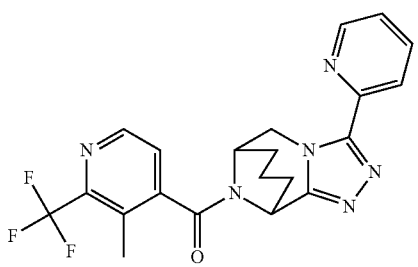

Example 68: (3-fluoro-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone

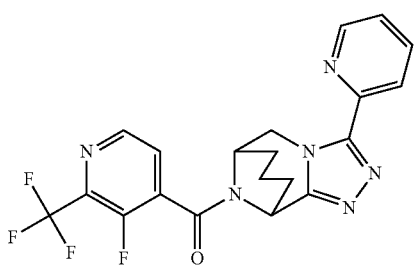 [SMILES: O=C(c1ccnc(C(F)(F)F)c1F)N1C2CCCC1c1nnc(-c3ccccn3)n1C2]

Example 69: (2,4-dichloro-3-fluorophenyl)(3-(pyridin-2-yl)-5,6,7,8,9,10-hexahydro-6,10-epimino[1,2,4]triazolo[4,3-a]azocin-11-yl)methanone

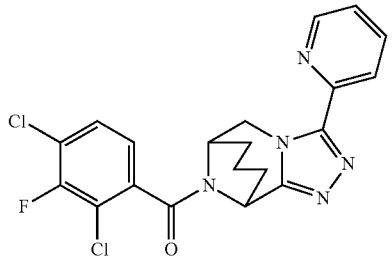 [SMILES: O=C(c1ccc(Cl)c(F)c1Cl)N1C2CCCC1c1nnc(-c3ccccn3)n1C2]

Example 70: (2,3-dichloro-4-fluorophenyl)(3-(pyridin-2-yl)-5,6,7,8,9,10-hexahydro-6,10-epimino[1,2,4]triazolo[4,3-a]azocin-11-yl)methanone

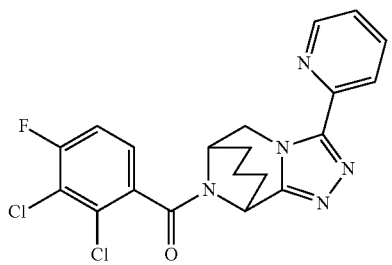 [SMILES: O=C(c1ccc(F)c(Cl)c1Cl)N1C2CCCC1c1nnc(-c3ccccn3)n1C2]

Example 71: (2-chloro-3-(trifluoromethyl)phenyl)(3-(3-fluoropyridin-2-yl)-5,6,7,8,9,10-hexahydro-6,10-epimino[1,2,4]triazolo[4,3-a]azocin-11-yl)methanone

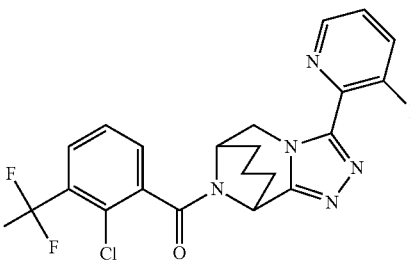

Example 72: (2-chloro-3-(trifluoromethyl)phenyl)(3-(3,5-difluoropyridin-2-yl)-5,6,7,8,9,10-hexahydro-6,10-epimino[1,2,4]triazolo[4,3-a]azocin-11-yl)methanone

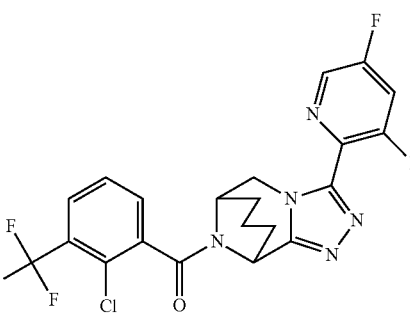

Example 73: ((2-chloro-3-(trifluoromethyl)phenyl)(3-(5-fluoro-6-methylpyridin-2-yl)-5,6,7,8,9,10-hexahydro-6,10-epimino[1,2,4]triazolo[4,3-a]azocin-11-yl)methanone

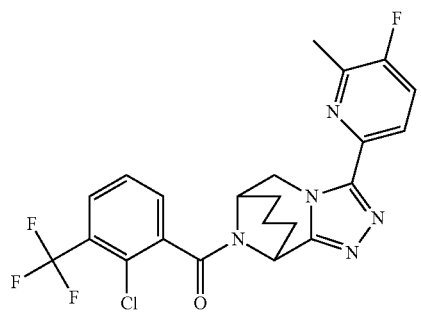 [SMILES: Cc1nc(-c2nnc3n2CC2CCCC3N2C(=O)c2cccc(C(F)(F)F)c2Cl)ccc1F]

Example 74: (2-chloro-3-(trifluoromethyl)phenyl)(3-(5-fluoro-4-methoxypyridin-2-yl)-5,6,7,8,9,10-hexahydro-6,10-epimino[1,2,4]triazolo[4,3-a]azocin-11-yl)methanone

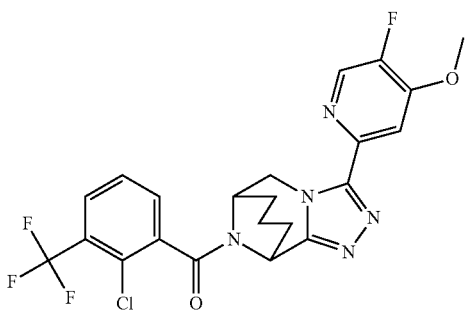 [SMILES: COc1cc(-c2nnc3n2CC2CCCC3N2C(=O)c2cccc(C(F)(F)F)c2Cl)ncc1F]

Example 75: (2-chloro-3-(trifluoromethyl)phenyl)(3-(4-(trifluoromethoxy)pyridin-2-yl)-5,6,7,8,9,10-hexahydro-6,10-epimino[1,2,4]triazolo[4,3-a]azocin-11-yl)methanone

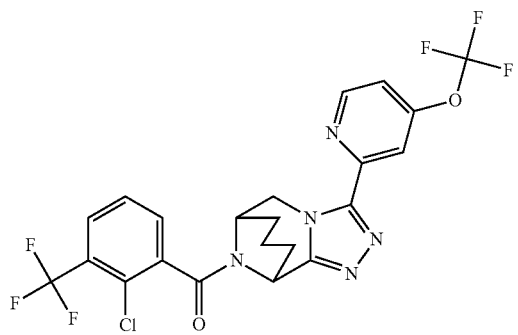 [SMILES: O=C(c1cccc(C(F)(F)F)c1Cl)N1C2CCCC1c1nnc(-c3cc(OC(F)(F)F)ccn3)n1C2]

Example 76: (2-chloro-3-(trifluoromethyl)phenyl)(3-(4-(difluoromethoxy)pyridin-2-yl)-5,6,7,8,9,10-hexahydro-6,10-epimino[1,2,4]triazolo[4,3-a]azocin-11-yl)methanone

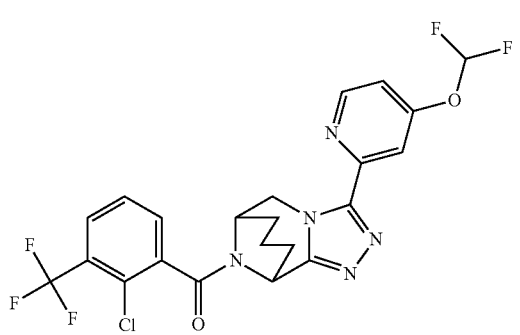 [SMILES: O=C(c1cccc(C(F)(F)F)c1Cl)N1C2CCCC1c1nnc(-c3cc(OC(F)F)ccn3)n1C2]

Example 77: (2-chloro-3-(trifluoromethyl)phenyl)(3-(4-hydroxypyridin-2-yl)-5,6,7,8,9,10-hexahydro-6,10-epimino[1,2,4]triazolo[4,3-a]azocin-11-yl)methanone

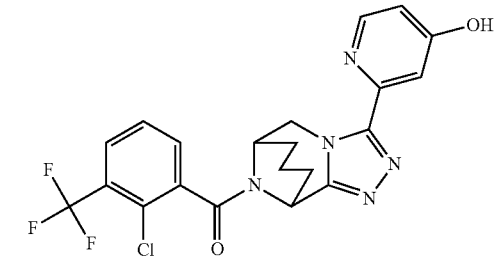 [SMILES: O=C(c1cccc(C(F)(F)F)c1Cl)N1C2CCCC1c1nnc(-c3cc(O)ccn3)n1C2]

Example 78: (2-chloro-3-(trifluoromethyl)phenyl)(3-(4-ethoxypyridin-2-yl)-5,6,7,8,9,10-hexahydro-6,10-epimino[1,2,4]triazolo[4,3-a]azocin-11-yl)methanone

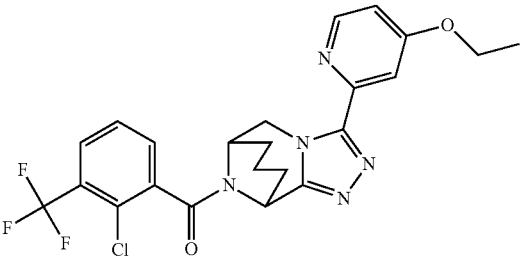 [SMILES: CCOc1ccnc(-c2nnc3n2CC2CCCC3N2C(=O)c2cccc(C(F)(F)F)c2Cl)c1]

Example 79: (2-chloro-3-(trifluoromethyl)phenyl) (3-(4-isopropoxypyridin-2-yl)-5,6,7,8,9,10-hexahydro-6,10-epimino[1,2,4]triazolo[4,3-a]azocin-11-yl)methanone

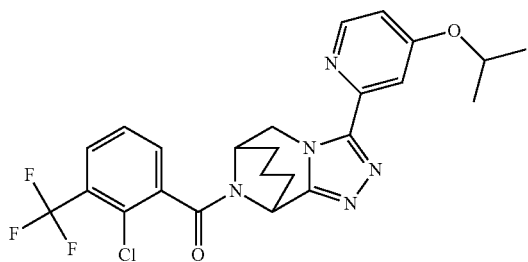 [SMILES: CC(C)Oc1ccnc(-c2nnc3n2CC2CCCC3N2C(=O)c2cccc(C(F)(F)F)c2Cl)c1]

Example 80: (2-chloro-3-(trifluoromethyl)phenyl) (3-(5-methylpyridin-2-yl)-5,6,7,8,9,10-hexahydro-6,10-epimino[1,2,4]triazolo[4,3-a]azocin-11-yl)methanone

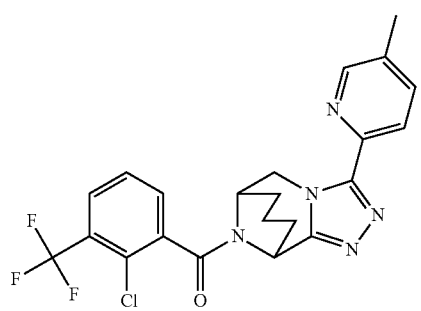 [SMILES: Cc1ccc(-c2nnc3n2CC2CCCC3N2C(=O)c2cccc(C(F)(F)F)c2Cl)nc1]

Example 81: (2-chloro-3-(trifluoromethyl)phenyl) (3-(4-methylpyridin-2-yl)-5,6,7,8,9,10-hexahydro-6,10-epimino[1,2,4]triazolo[4,3-a]azocin-11-yl)methanone

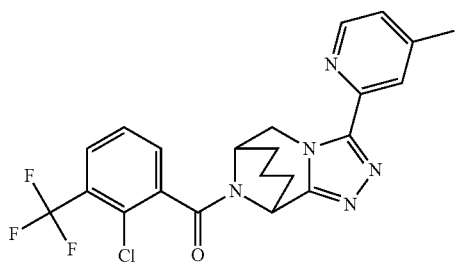 [SMILES: Cc1ccnc(-c2nnc3n2CC2CCCC3N2C(=O)c2cccc(C(F)(F)F)c2Cl)c1]

Example 82: (2-chloro-3-(trifluoromethyl)phenyl) (3-(4-(trifluoromethyl)pyridin-2-yl)-5,6,7,8,9,10-hexahydro-6,10-epimino[1,2,4]triazolo[4,3-a]azocin-11-yl)methanone

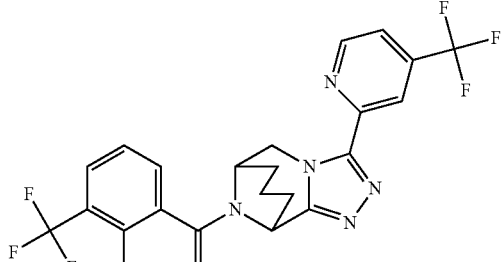

Example 83: (2-chloro-3-(trifluoromethyl)phenyl) (3-(5-fluoro-4-methyl pyridin-2-yl)-5,6,7,8,9,10-hexahydro-6,10-epimino[1,2,4]triazolo[4,3-a]azocin-11-yl)methanone

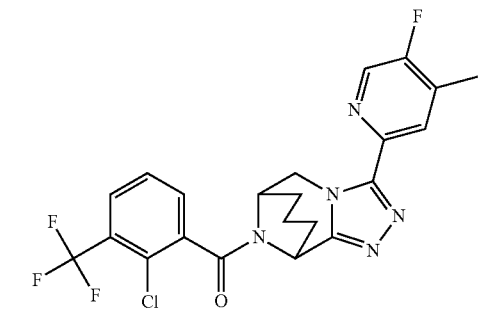 [SMILES: Cc1cc(-c2nnc3n2CC2CCCC3N2C(=O)c2cccc(C(F)(F)F)c2Cl)ncc1F]

Example 84: (2-chloro-3-(trifluoromethyl)phenyl) (3-(5-fluoro-4-(trifluoromethyl)pyridin-2-yl)-5,6,7,8,9,10-hexahydro-6,10-epimino[1,2,4]triazolo[4,3-a] azocin-11-yl)methanone

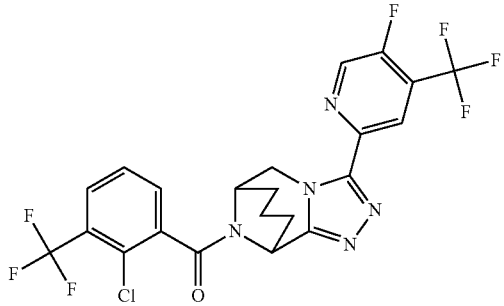 [SMILES: O=C(c1cccc(C(F)(F)F)c1Cl)N1C2CCCC1c1nnc(-c3cc(C(F)(F)F)c(F)cn3)n1C2]

Example 85: (2-chloro-3-(trifluoromethyl)phenyl)
((6R,10S)-3-(pyrazin-2-yl)-6,7,9,10-tetrahydro-5H-
6,10-epimino[1,2,4]triazolo[3,4-d][1,5]oxazocin-11-
yl)methanone

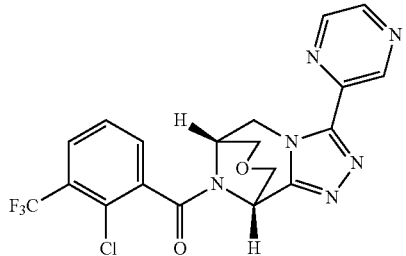 [SMILES: O=C(c1cccc(C(F)(F)F)c1Cl)N1[C@H]2COC[C@@H]1c1nnc(-c3cnccn3)n1C2]

Example 86: (2,3-dichloro-4-fluorophenyl)((6R,
10S)-3-(pyrazin-2-yl)-6,7,9,10-tetrahydro-5H-6,10-
epimino[1,2,4]triazolo[3,4-d][1,5]oxazocin-11-yl)
methanone

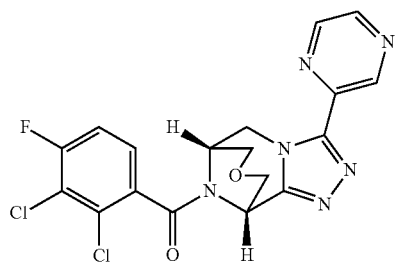 [SMILES: O=C(c1ccc(F)c(Cl)c1Cl)N1[C@H]2COC[C@@H]1c1nnc(-c3cnccn3)n1C2]

Example 87: (2-methyl-3-(trifluoromethyl)phenyl)
((6R,10S)-3-(pyrazin-2-yl)-6,7,9,10-tetrahydro-5H-
6,10-epimino[1,2,4]triazolo[3,4-d][1,5]oxazocin-11-
yl)methanone

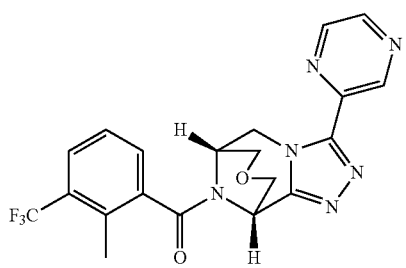 [SMILES: Cc1c(C(=O)N2[C@H]3COC[C@@H]2c2nnc(-c4cnccn4)n2C3)cccc1C(F)(F)F]

Example 88: (2-fluoro-3-(trifluoromethyl)phenyl)
((6R,10S)-3-(pyrazin-2-yl)-6,7,9,10-tetrahydro-5H-
6,10-epimino[1,2,4]triazolo[3,4-d][1,5]oxazocin-11-
yl)methanone

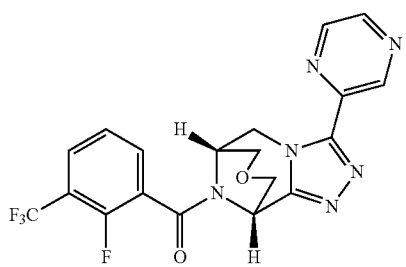

Example 89: (3-fluoro-2-(trifluoromethyl)pyridin-4-
yl)((6R,10S)-3-(pyrazin-2-yl)-6,7,9,10-tetrahydro-
5H-6,10-epimino[1,2,4]triazolo[3,4-d][1,5]oxazocin-
11-yl)methanone

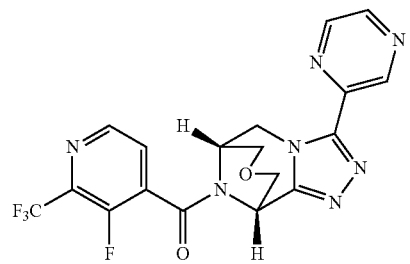 [SMILES: O=C(c1ccnc(C(F)(F)F)c1F)N1[C@H]2COC[C@@H]1c1nnc(-c3cnccn3)n1C2]

Example 90: (2,3-dichlorophenyl)((6R,10S)-3-
(pyrazin-2-yl)-6,7,9,10-tetrahydro-5H-6,10-epimino
[1,2,4]triazolo[3,4-d][1,5]oxazocin-11-yl)methanone

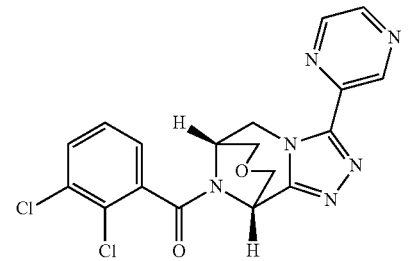 [SMILES: O=C(c1cccc(Cl)c1Cl)N1[C@H]2COC[C@@H]1c1nnc(-c3cnccn3)n1C2]

Example 91: (2-chloro-3-(trifluoromethyl)phenyl)
((6R,10S)-3-(pyrimidin-2-yl)-6,7,9,10-tetrahydro-
5H-6,10-epimino[1,2,4]triazolo[3,4-d][1,5]oxazocin-
11-yl)methanone

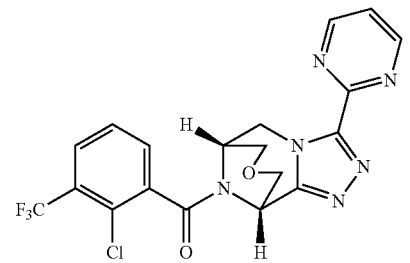 [SMILES: O=C(c1cccc(C(F)(F)F)c1Cl)N1[C@H]2COC[C@@H]1c1nnc(-c3ncccn3)n1C2]

Example 92: (2,3-dichloro-4-fluorophenyl)((6R,
10S)-3-(pyrimidin-2-yl)-6,7,9,10-tetrahydro-5H-6,
10-epimino[1,2,4]triazolo[3,4-d][1,5]oxazocin-11-
yl)methanone

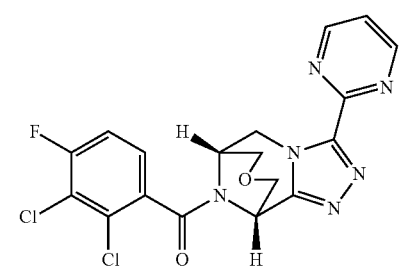 [SMILES: O=C(c1ccc(F)c(Cl)c1Cl)N1[C@H]2COC[C@@H]1c1nnc(-c3ncccn3)n1C2]

Example 93: (2-methyl-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone

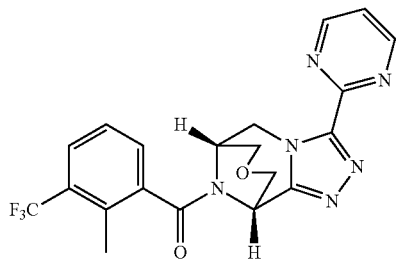 [SMILES: Cc1c(C(=O)N2[C@H]3COC[C@@H]2c2nnc(-c4ncccn4)n2C3)cccc1C(F)(F)F]

Example 94: (2-fluoro-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone

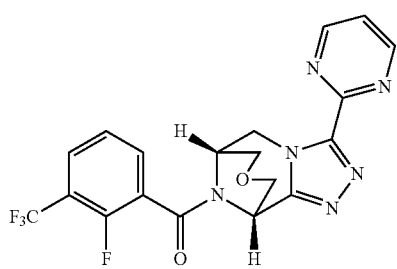 [SMILES: O=C(c1cccc(C(F)(F)F)c1F)N1[C@H]2COC[C@@H]1c1nnc(-c3ncccn3)n1C2]

Example 95: (3-fluoro-2-(trifluoromethyl)pyridin-4-yl)((6R,10S)-3-(pyrazin-2-yl)-6,7,9,10-tetrahydro-5H-6,10-epimino[1,2,4]triazolo[3,4-d][1,5]oxazocin-11-yl)methanone

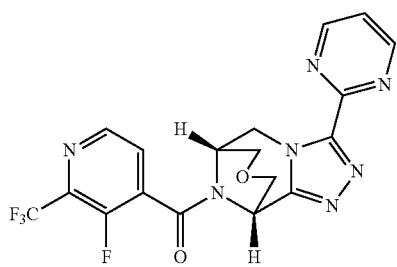 [SMILES: O=C(c1ccnc(C(F)(F)F)c1F)N1[C@H]2COC[C@@H]1c1nnc(-c3ncccn3)n1C2]

Example 96: (2,3-dichlorophenyl)((6R,10S)-3-(pyrimidin-2-yl)-6,7,9,10-tetrahydro-5H-6,10-epimino[1,2,4]triazolo[3,4-d][1,5]oxazocin-11-yl)methanone

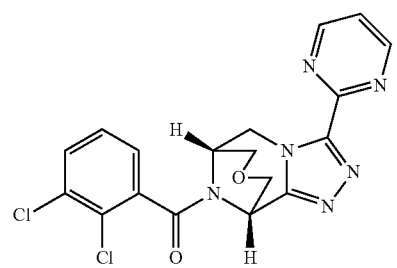 [SMILES: O=C(c1cccc(Cl)c1Cl)N1[C@H]2COC[C@@H]1c1nnc(-c3ncccn3)n1C2]

Example 97: (2-chloro-3-(trifluoromethyl)phenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone

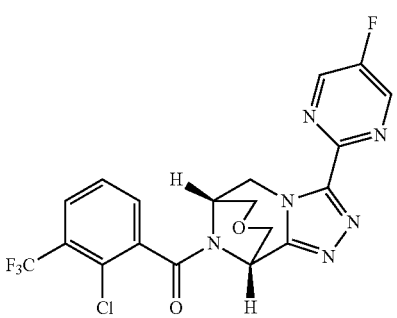 [SMILES: O=C(c1cccc(C(F)(F)F)c1Cl)N1[C@H]2COC[C@@H]1c1nnc(-c3ncc(F)cn3)n1C2]

Example 98: (2,3-dichloro-4-fluorophenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone

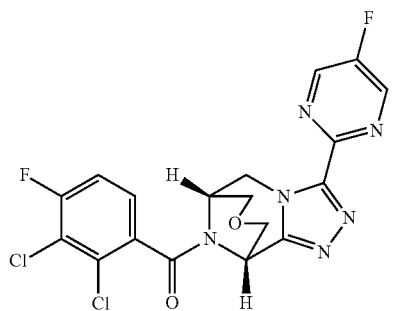

Example 99: ((6R,10S)-3-(5-fluoropyrimidin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone

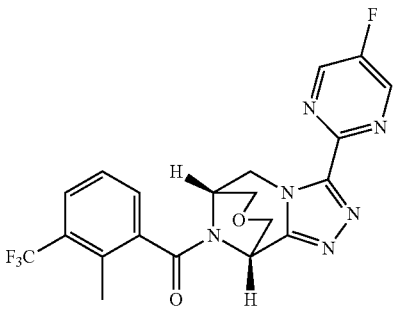 [SMILES: Cc1c(C(=O)N2[C@H]3COC[C@@H]2c2nnc(-c4ncc(F)cn4)n2C3)cccc1C(F)(F)F]

Example 100: (2-fluoro-3-(trifluoromethyl)phenyl)
((6R,10S)-3-(5-fluoropyrimidin-2-yl)-6,7,9,10-tetra-
hydro-5H-6,10-epimino[1,2,4]triazolo[3,4-d][1,5]
oxazocin-11-yl)methanone

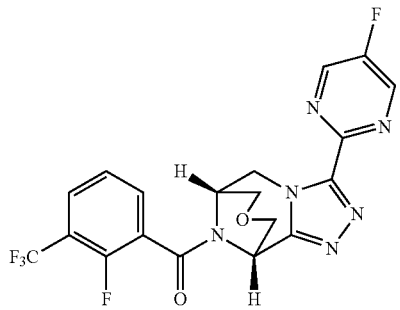

Example 101: (3-fluoro-2-(trifluoromethyl)pyridin-
4-yl)((6R,10S)-3-(5-fluoropyrimidin-2-yl)-6,7,9,10-
tetrahydro-5H-6,10-epimino[1,2,4]triazolo[3,4-d][1,
5]oxazocin-11-yl)methanone

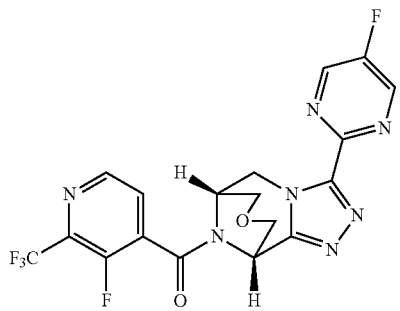 [SMILES: O=C(c1ccnc(C(F)(F)F)c1F)N1[C@H]2COC[C@@H]1c1nnc(-c3ncc(F)cn3)n1C2]

Example 102: (2,3-dichlorophenyl)((6R,10S)-3-(5-
fluoropyrimidin-2-yl)-6,7,9,10-tetrahydro-5H-6,10-
epimino[1,2,4]triazolo[3,4-d][1,5]oxazocin-11-yl)
methanone

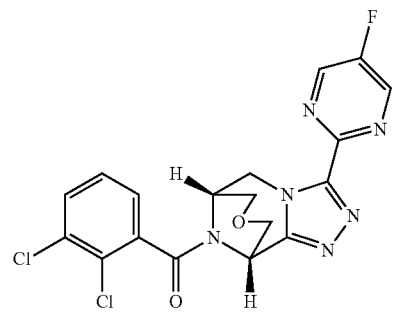

Example 103: (2-chloro-3-(trifluoromethyl)phenyl)
((6R,10S)-3-(5-fluoropyridin-2-yl)-6,7,9,10-tetra-
hydro-5H-6,10-epimino[1,2,4]triazolo[3,4-d][1,5]
oxazocin-11-yl)methanone

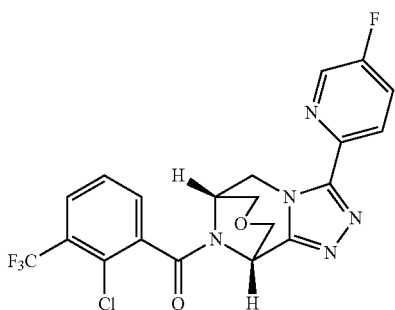 [SMILES: O=C(c1cccc(C(F)(F)F)c1Cl)N1[C@H]2COC[C@@H]1c1nnc(-c3ccc(F)cn3)n1C2]

Example 104: (2,3-dichloro-4-fluorophenyl)((6R,
10S)-3-(5-fluoropyridin-2-yl)-6,7,9,10-tetrahydro-
5H-6,10-epimino[1,2,4]triazolo[3,4-d][1,5]oxazocin-
11-yl)methanone

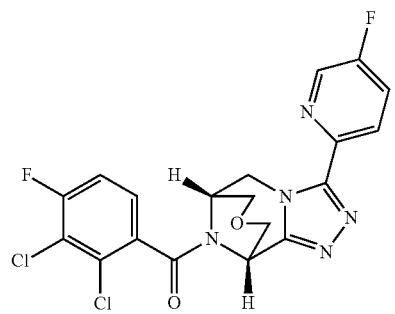

Example 105: ((6R,10S)-3-(5-fluoropyridin-2-yl)-6,
7,9,10-tetrahydro-5H-6,10-epimino[1,2,4]triazolo[3,
4-d][1,5]oxazocin-11-yl)(2-methyl-3-(trifluorom-
ethyl)phenyl)methanone

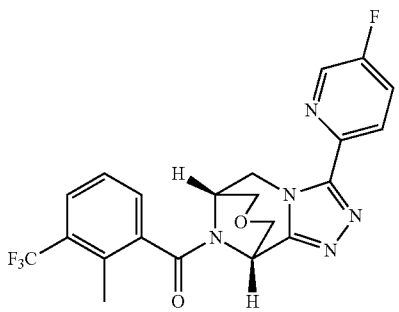 [SMILES: Cc1c(C(=O)N2[C@H]3COC[C@@H]2c2nnc(-c4ccc(F)cn4)n2C3)cccc1C(F)(F)F]

Example 106: (2-fluoro-3-(trifluoromethyl)phenyl)
((6R,10S)-3-(5-fluoropyridin-2-yl)-6,7,9,10-tetra-
hydro-5H-6,10-epimino[1,2,4]triazolo[3,4-d][1,5]
oxazocin-11-yl)methanone

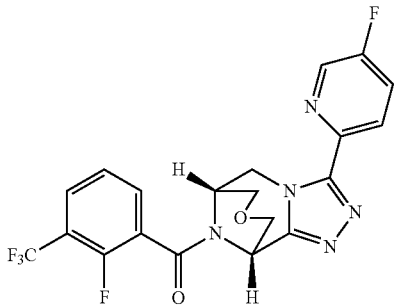

Example 107: (3-fluoro-2-(trifluoromethyl)pyridin-
4-yl)((6R,10S)-3-(5-fluoropyridin-2-yl)-6,7,9,10-
tetrahydro-5H-6,10-epimino[1,2,4]triazolo[3,4-d][1,
5]oxazocin-11-yl)methanone

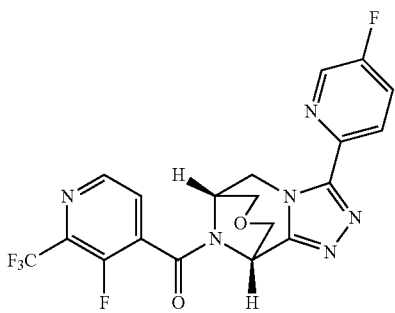

Example 108: (2,3-dichlorophenyl)((6R,10S)-3-(5-
fluoropyridin-2-yl)-6,7,9,10-tetrahydro-5H-6,10-
epimino[1,2,4]triazolo[3,4-d][1,5]oxazocin-11-yl)
methanone

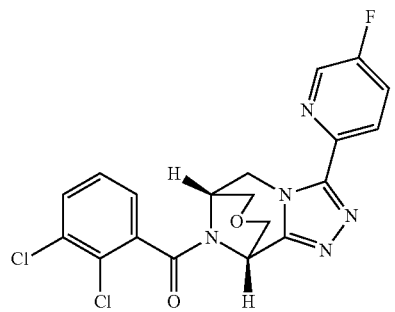 [SMILES: O=C(c1cccc(Cl)c1Cl)N1[C@H]2COC[C@@H]1c1nnc(-c3ccc(F)cn3)n1C2]

Example 109: (2-chloro-3-(trifluoromethyl)phenyl)
((6R,10S)-3-(4-methoxypyridin-2-yl)-6,7,9,10-tetra-
hydro-5H-6,10-epimino[1,2,4]triazolo[3,4-d][1,5]
oxazocin-11-yl)methanone

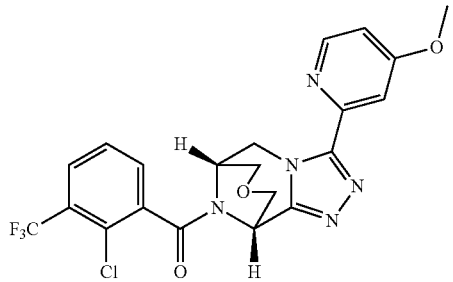 [SMILES: COc1ccnc(-c2nnc3n2C[C@@H]2COC[C@H]3N2C(=O)c2cccc(C(F)(F)F)c2F)c1]

Example 110: (2,3-dichloro-4-fluorophenyl)((6R,
10S)-3-(4-methoxypyridin-2-yl)-6,7,9,10-tetrahydro-
5H-6,10-epimino[1,2,4]triazolo[3,4-d][1,5]oxazocin-
11-yl)methanone

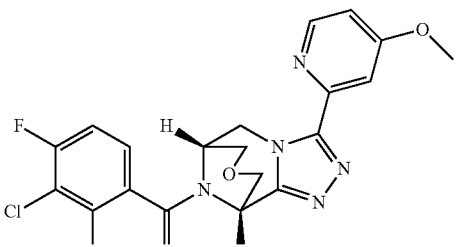

Example 111: ((6R,10S)-3-(4-methoxypyridin-2-yl)-
6,7,9,10-tetrahydro-5H-6,10-epimino[1,2,4]triazolo
[3,4-d][1,5]oxazocin-11-yl)(2-methyl-3-(trifluorom-
ethyl)phenyl)methanone

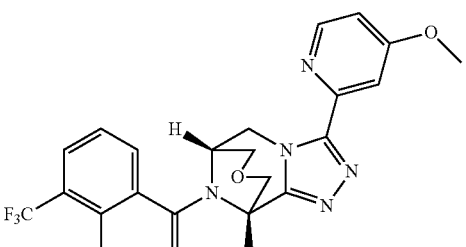

Example 112: (2-fluoro-3-(trifluoromethyl)phenyl)
((6R,10S)-3-(4-methoxypyridin-2-yl)-6,7,9,10-tetra-
hydro-5H-6,10-epimino[1,2,4]triazolo[3,4-d][1,5]
oxazocin-11-yl)methanone

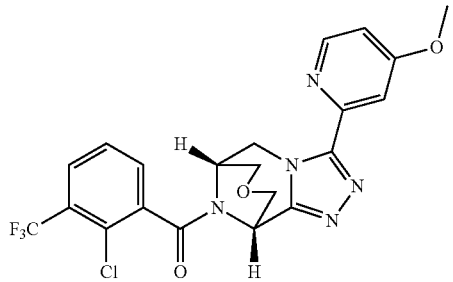 [SMILES: COc1ccnc(-c2nnc3n2C[C@@H]2COC[C@H]3N2C(=O)c2cccc(C(F)(F)F)c2F)c1]

Example 113: (3-fluoro-2-(trifluoromethyl)pyridin-4-yl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone

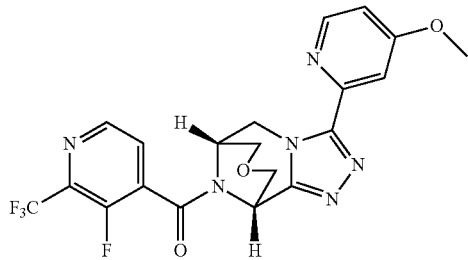 [SMILES: COc1ccnc(-c2nnc3n2C[C@@H]2COC[C@H]3N2C(=O)c2ccnc(C(F)(F)F)c2F)c1]

Example 114: (2,3-dichlorophenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone

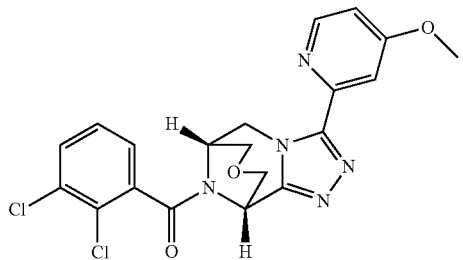 [SMILES: COc1ccnc(-c2nnc3n2C[C@@H]2COC[C@H]3N2C(=O)c2cccc(Cl)c2Cl)c1]

Example 115: (2-chloro-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone

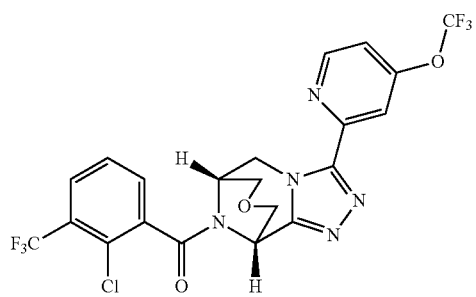

Example 116: (2,3-dichloro-4-fluorophenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone

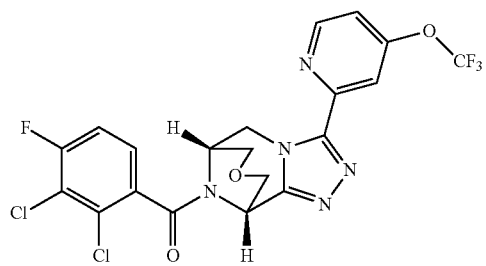 [SMILES: O=C(c1ccc(F)c(Cl)c1Cl)N1[C@H]2COC[C@@H]1c1nnc(-c3cc(OC(F)(F)F)ccn3)n1C2]

Example 117: (2-methyl-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone

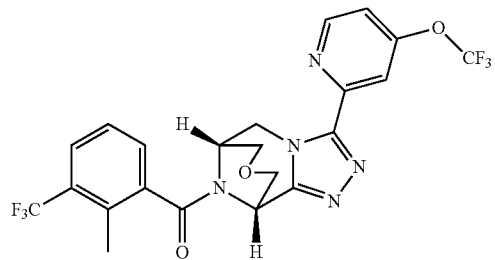 [SMILES: Cc1c(C(=O)N2[C@H]3COC[C@@H]2c2nnc(-c4cc(OC(F)(F)F)ccn4)n2C3)cccc1C(F)(F)F]

Example 118: (2-fluoro-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone

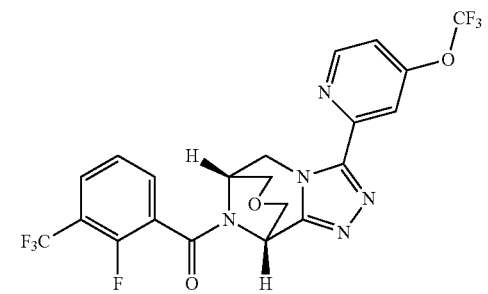 [SMILES: O=C(c1cccc(C(F)(F)F)c1F)N1[C@H]2COC[C@@H]1c1nnc(-c3cc(OC(F)(F)F)ccn3)n1C2]

Example 119: (3-fluoro-2-(trifluoromethyl)pyridin-4-yl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone

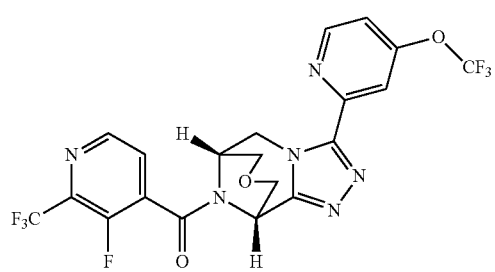 [SMILES: O=C(c1ccnc(C(F)(F)F)c1F)N1[C@H]2COC[C@@H]1c1nnc(-c3cc(OC(F)(F)F)ccn3)n1C2]

Example 120: (2,3-dichlorophenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone

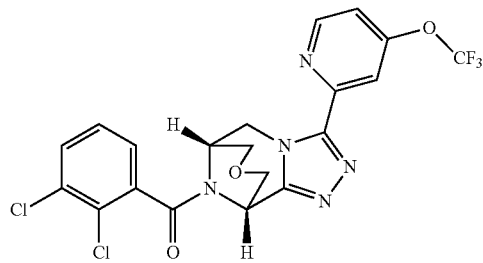 [SMILES: O=C(c1cccc(Cl)c1Cl)N1[C@H]2COC[C@@H]1c1nnc(-c3cc(OC(F)(F)F)ccn3)n1C2]

Example 121: (2-chloro-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone

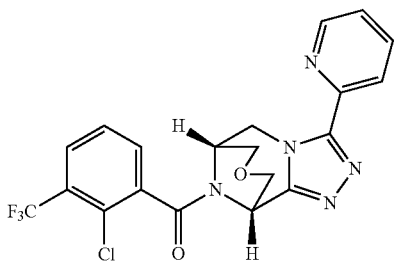

Example 122: (2,3-dichloro-4-fluorophenyl)((6R,10S)-3-(pyridin-2-yl)-6,7,9,10-tetrahydro-5H-6,10-epimino[1,2,4]triazolo[3,4-d][1,5]oxazocin-11-yl)methanone

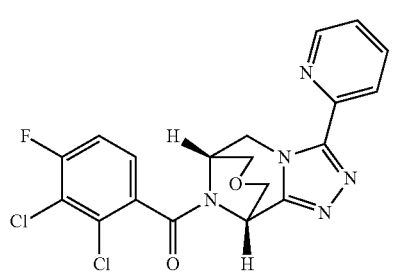 [SMILES: O=C(c1ccc(F)c(Cl)c1Cl)N1[C@H]2COC[C@@H]1c1nnc(-c3ccccn3)n1C2]

Example 123: (2-methyl-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone

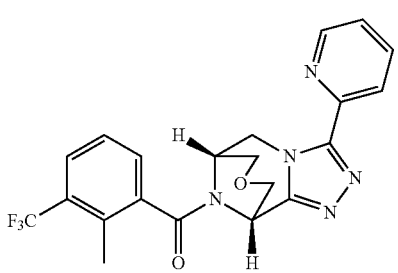 [SMILES: Cc1c(C(=O)N2[C@H]3COC[C@@H]2c2nnc(-c4ccccn4)n2C3)cccc1C(F)(F)F]

Example 124: (2-fluoro-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone

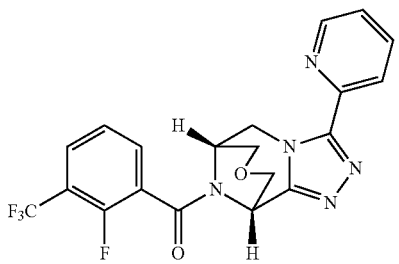 [SMILES: O=C(c1cccc(C(F)(F)F)c1F)N1[C@H]2COC[C@@H]1c1nnc(-c3ccccn3)n1C2]

Example 125: (3-fluoro-2-(trifluoromethyl)pyridin-4-yl)((6R,10S)-3-(pyridin-2-yl)-6,7,9,10-tetrahydro-5H-6,10-epimino[1,2,4]triazolo[3,4-d][1,5]oxazocin-11-yl)methanone

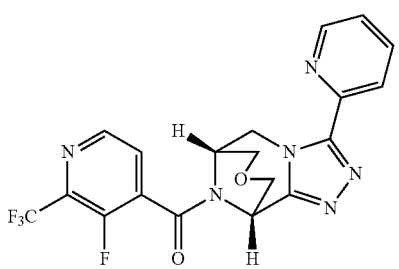 [SMILES: O=C(c1ccnc(C(F)(F)F)c1F)N1[C@H]2COC[C@@H]1c1nnc(-c3ccccn3)n1C2]

Example 126: (2,3-dichlorophenyl)((6R,10S)-3-(pyridin-2-yl)-6,7,9,10-tetrahydro-5H-6,10-epimino[1,2,4]triazolo[3,4-d][1,5]oxazocin-11-yl)methanone

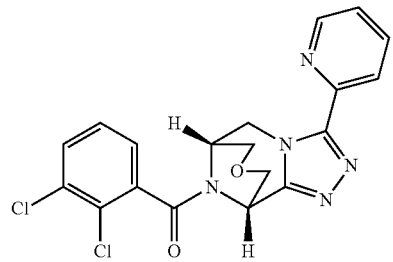 [SMILES: O=C(c1cccc(Cl)c1Cl)N1[C@H]2COC[C@@H]1c1nnc(-c3ccccn3)n1C2]

Example 127: (2-chloro-3-(trifluoromethyl)phenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone

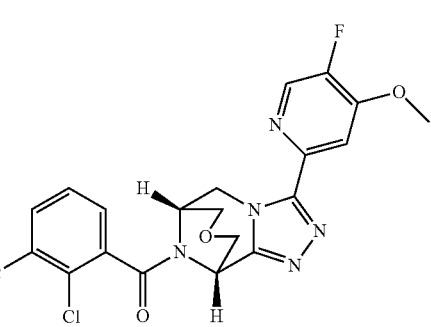

Example 128: (2,3-dichloro-4-fluorophenyl)(((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone

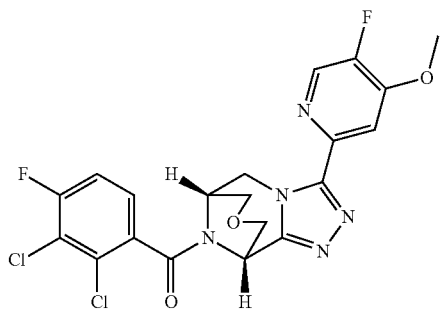 [SMILES: COc1cc(-c2nnc3n2C[C@@H]2COC[C@H]3N2C(=O)c2ccc(F)c(Cl)c2Cl)ncc1F]

Example 129: ((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone

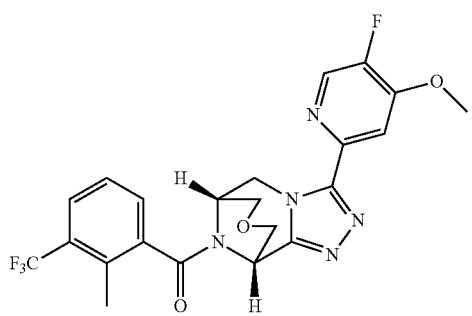 [SMILES: COc1cc(-c2nnc3n2C[C@@H]2COC[C@H]3N2C(=O)c2cccc(C(F)(F)F)c2C)ncc1F]

Example 130: (2-fluoro-3-(trifluoromethyl)phenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone

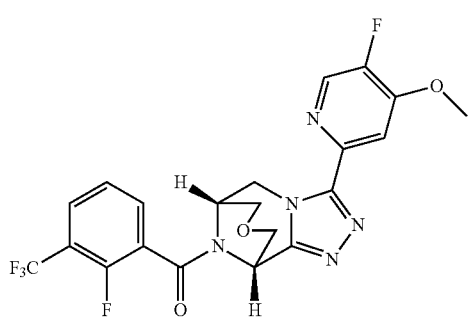 [SMILES: COc1cc(-c2nnc3n2C[C@@H]2COC[C@H]3N2C(=O)c2cccc(C(F)(F)F)c2F)ncc1F]

Example 131: (3-fluoro-2-(trifluoromethyl)pyridin-4-yl)(((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone

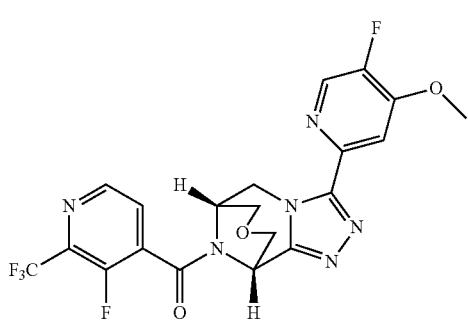 [SMILES: COc1cc(-c2nnc3n2C[C@@H]2COC[C@H]3N2C(=O)c2ccnc(C(F)(F)F)c2F)ncc1F]

Example 132: (2,3-dichlorophenyl)(((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone

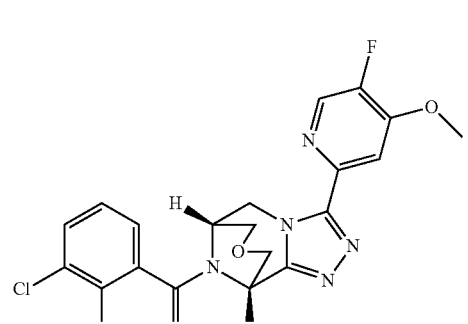

Example 133: ((6R,10S)-3-(1H-pyrazol-3-yl)-6,7,9,10-tetrahydro-5H-6,10-epimino[1,2,4]triazolo[3,4-d][1,5]oxazocin-11-yl)(2-chloro-3-(trifluoromethyl)phenyl)methanone

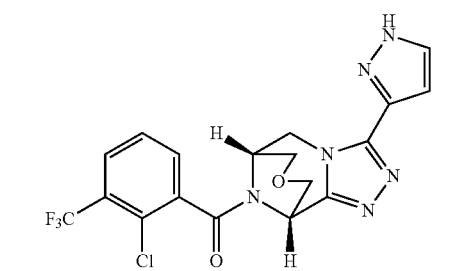 [SMILES: O=C(c1cccc(C(F)(F)F)c1Cl)N1[C@H]2COC[C@@H]1c1nnc(-c3cc[nH]n3)n1C2]

Example 134: ((6R,10S)-3-(1H-pyrazol-3-yl)-6,7,9,10-tetrahydro-5H-6,10-epimino[1,2,4]triazolo[3,4-d][1,5]oxazocin-11-yl)(2,3-dichloro-4-fluorophenyl)methanone

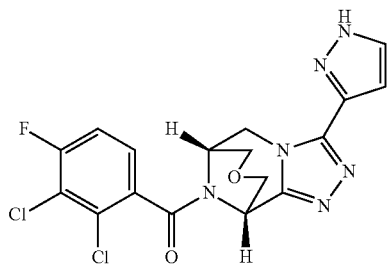 [SMILES: O=C(c1ccc(F)c(Cl)c1Cl)N1[C@H]2COC[C@@H]1c1nnc(-c3cc[nH]n3)n1C2]

Example 135: ((6R,10S)-3-(1H-pyrazol-3-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone

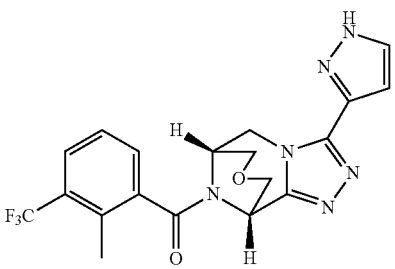 [SMILES: Cc1c(C(=O)N2[C@H]3COC[C@@H]2c2nnc(-c4cc[nH]n4)n2C3)cccc1C(F)(F)F]

Example 136: ((6R,10S)-3-(1H-pyrazol-3-yl)-6,7,9,10-tetrahydro-5H-6,10-epimino[1,2,4]triazolo[3,4-d][1,5]oxazocin-11-yl)(2-fluoro-3-(trifluoromethyl)phenyl)methanone

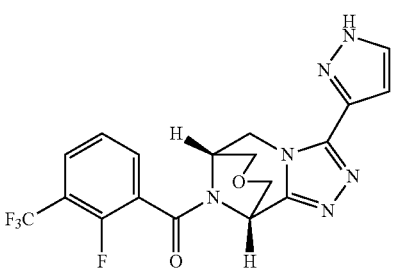

Example 137: ((6R,10S)-3-(1H-pyrazol-3-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone

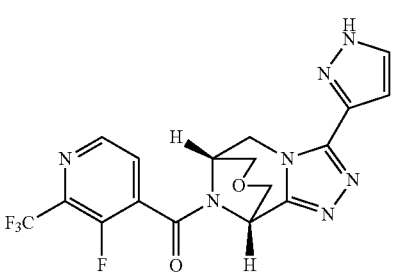 [SMILES: O=C(c1ccnc(C(F)(F)F)c1F)N1[C@H]2COC[C@@H]1c1nnc(-c3cc[nH]n3)n1C2]

Example 138: ((6R,10S)-3-(1H-pyrazol-3-yl)-6,7,9,10-tetrahydro-5H-6,10-epimino[1,2,4]triazolo[3,4-d][1,5]oxazocin-11-yl)(2,3-dichlorophenyl)methanone

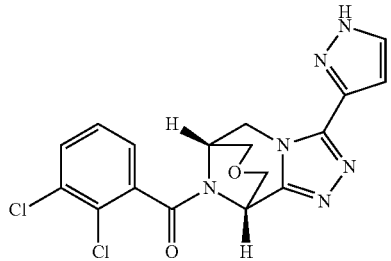 [SMILES: O=C(c1cccc(Cl)c1Cl)N1[C@H]2COC[C@@H]1c1nnc(-c3cc[nH]n3)n1C2]

Example 139: (2-chloro-3-(trifluoromethyl)phenyl)((6R,10S)-3-(4-fluorophenyl)-6,7,9,10-tetrahydro-5H-6,10-epimino[1,2,4]triazolo[3,4-d][1,5]oxazocin-11-yl)methanone

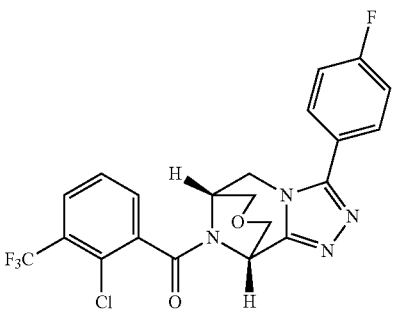 [SMILES: O=C(c1cccc(C(F)(F)F)c1Cl)N1[C@H]2COC[C@@H]1c1nnc(-c3ccc(F)cc3)n1C2]

Example 140: (2,3-dichloro-4-fluorophenyl)((6R,10S)-3-(4-fluorophenyl)-6,7,9,10-tetrahydro-5H-6,10-epimino[1,2,4]triazolo[3,4-d][1,5]oxazocin-11-yl)methanone

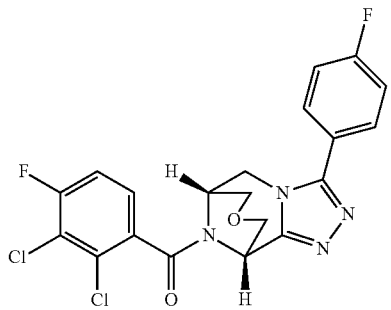 [SMILES: O=C(c1ccc(F)c(Cl)c1Cl)N1[C@H]2COC[C@@H]1c1nnc(-c3ccc(F)cc3)n1C2]

Example 141: ((6R,10S)-3-(4-fluorophenyl)-6,7,9,10-tetrahydro-5H-6,10-epimino[1,2,4]triazolo[3,4-d][1,5]oxazocin-11-yl)(2-methyl-3-(trifluoromethyl)phenyl)methanone

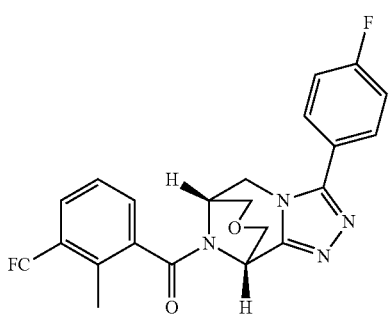

Example 142: (2-fluoro-3-(trifluoromethyl)phenyl)
((6R,10S)-3-(4-fluorophenyl)-6,7,9,10-tetrahydro-
5H-6,10-epimino[1,2,4]triazolo[3,4-d][1,5]oxazocin-
11-yl)methanone

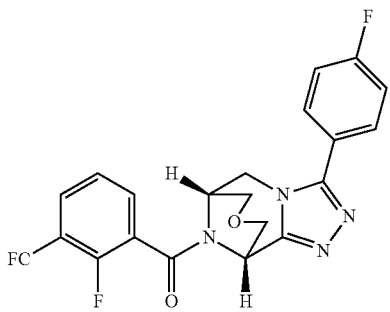

Example 143: (3-fluoro-2-(trifluoromethyl)pyridin-
4-yl)((6R,10S)-3-(4-fluorophenyl)-6,7,9,10-tetra-
hydro-5H-6,10-epimino[1,2,4]triazolo[3,4-d][1,5]
oxazocin-11-yl)methanone

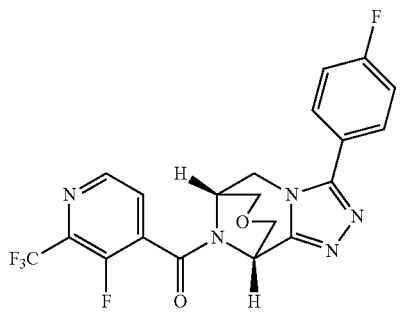 [SMILES: O=C(c1ccnc(C(F)(F)F)c1F)N1[C@H]2COC[C@@H]1c1nnc(-c3ccc(F)cc3)n1C2]

Example 144: (2,3-dichlorophenyl)((6R,10S)-3-(4-
fluorophenyl)-6,7,9,10-tetrahydro-5H-6,10-epimino
[1,2,4]triazolo[3,4-d][1,5]oxazocin-11-yl)methanone

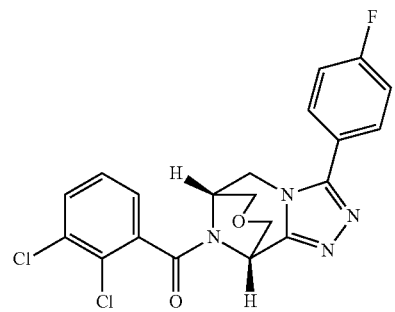 [SMILES: O=C(c1cccc(Cl)c1Cl)N1[C@H]2COC[C@@H]1c1nnc(-c3ccc(F)cc3)n1C2]

Example 145: (2-chloro-3-(trifluoromethyl)phenyl)
((6R,10S)-3-(3-fluoro-4-methoxypyridin-2-yl)-6,7,9,
10-tetrahydro-5H-6,10-epimino[1,2,4]triazolo[3,4-d]
[1,5]oxazocin-11-yl)methanone

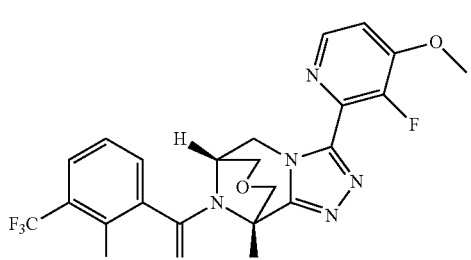

Example 146: (2,3-dichloro-4-fluorophenyl)((6R,
10S)-3-(3-fluoro-4-methoxypyridin-2-yl)-6,7,9,10-
tetrahydro-5H-6,10-epimino[1,2,4]triazolo[3,4-d][1,
5]oxazocin-11-yl)methanone

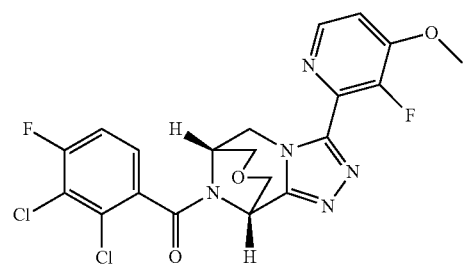 [SMILES: COc1ccnc(-c2nnc3n2C[C@@H]2COC[C@H]3N2C(=O)c2ccc(F)c(Cl)c2Cl)c1F]

Example 147 ((6R,10S)-3-(3-fluoro-4-methoxypyri-
din-2-yl)-6,7,9,10-tetrahydro-5H-6,10-epimino[1,2,
4]triazolo[3,4-d][1,5]oxazocin-11-yl)(2-methyl-3-
(trifluoromethyl)phenyl)methanone

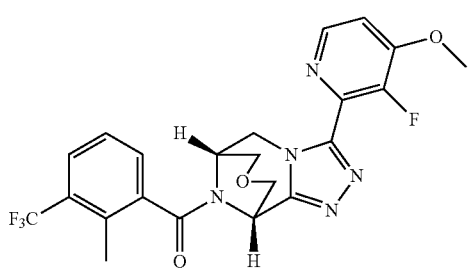 [SMILES: COc1ccnc(-c2nnc3n2C[C@@H]2COC[C@H]3N2C(=O)c2cccc(C(F)(F)F)c2C)c1F]

Example 148: (2-fluoro-3-(trifluoromethyl)phenyl)
((6R,10S)-3-(3-fluoro-4-methoxypyridin-2-yl)-6,7,9,
10-tetrahydro-5H-6,10-epimino[1,2,4]triazolo[3,4-d]
[1,5]oxazocin-11-yl)methanone

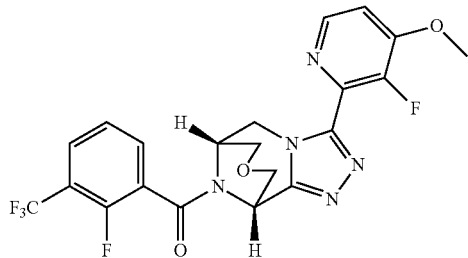 [SMILES: COc1ccnc(-c2nnc3n2C[C@@H]2COC[C@H]3N2C(=O)c2cccc(C(F)(F)F)c2F)c1F]

Example 149: (3-fluoro-2-(trifluoromethyl)pyridin-
4-yl)((6R,10S)-3-(3-fluoro-4-methoxypyridin-2-yl)-
6,7,9,10-tetrahydro-5H-6,10-epimino[1,2,4]triazolo
[3,4-d][1,5]oxazocin-11-yl)methanone

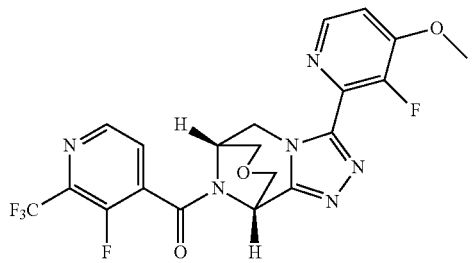

Example 150: (2,3-dichlorophenyl)((6R,10S)-3-(3-
fluoro-4-methoxypyridin-2-yl)-6,7,9,10-tetrahydro-
5H-6,10-epimino[1,2,4]triazolo[3,4-d][1,5]oxazocin-
11-yl)methanone

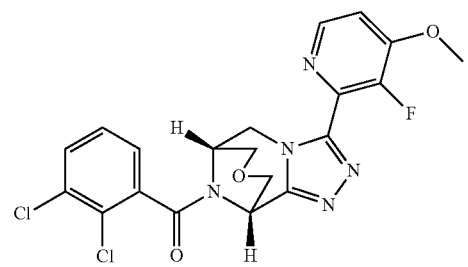 [SMILES: COc1ccnc(-c2nnc3n2C[C@@H]2COC[C@H]3N2C(=O)c2cccc(Cl)c2Cl)c1F]

Example 151: (2-chloro-3-(trifluoromethyl)phenyl)
((6R,10S)-3-(4-(difluoromethoxy)pyridin-2-yl)-6,7,
9,10-tetrahydro-5H-6,10-epimino[1,2,4]triazolo[3,4-
d][1,5]oxazocin-11-yl)methanone

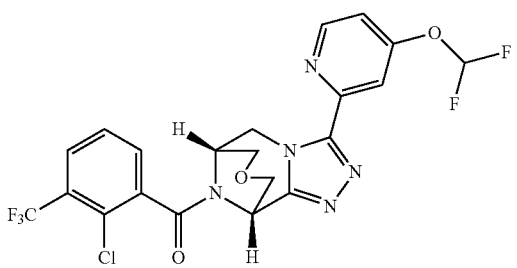 [SMILES: O=C(c1cccc(C(F)(F)F)c1Cl)N1[C@H]2COC[C@@H]1c1nnc(-c3cc(OC(F)F)ccn3)n1C2]

Example 152: (2,3-dichloro-4-fluorophenyl)((6R,
10S)-3-(4-(difluoromethoxy)pyridin-2-yl)-6,7,9,10-
tetrahydro-5H-6,10-epimino[1,2,4]triazolo[3,4-d][1,
5]oxazocin-11-yl)methanone

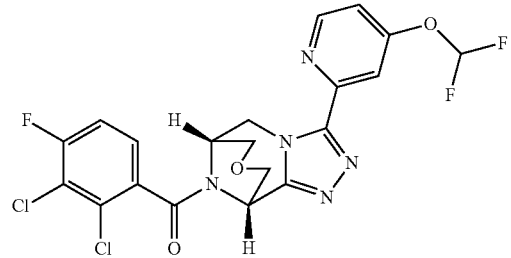 [SMILES: O=C(c1ccc(F)c(Cl)c1Cl)N1[C@H]2COC[C@@H]1c1nnc(-c3cc(OC(F)F)ccn3)n1C2]

Example 153: ((6R,10S)-3-(4-(difluoromethoxy)
pyridin-2-yl)-6,7,9,10-tetrahydro-5H-6,10-epimino
[1,2,4]triazolo[3,4-d][1,5]oxazocin-11-yl)(2-methyl-
3-(trifluoromethyl)phenyl)methanone

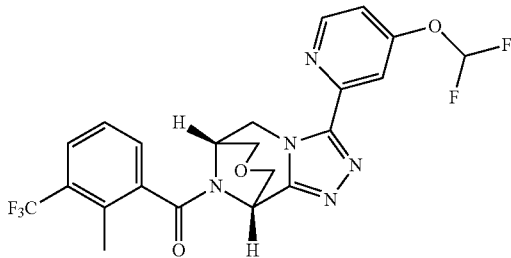 [SMILES: Cc1c(C(=O)N2[C@H]3COC[C@@H]2c2nnc(-c4cc(OC(F)F)ccn4)n2C3)cccc1C(F)(F)F]

Example 154: ((6R,10S)-3-(4-(difluoromethoxy)
pyridin-2-yl)-6,7,9,10-tetrahydro-5H-6,10-epimino
[1,2,4]triazolo[3,4-d][1,5]oxazocin-11-yl)(2-fluoro-
3-(trifluoromethyl)phenyl)methanone

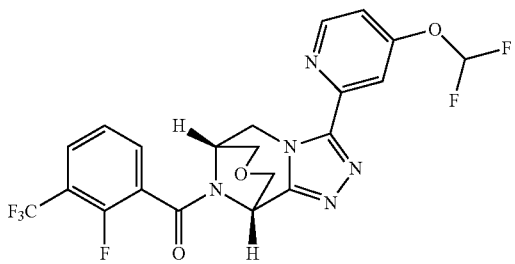 [SMILES: O=C(c1cccc(C(F)(F)F)c1F)N1[C@H]2COC[C@@H]1c1nnc(-c3cc(OC(F)F)ccn3)n1C2]

Example 155: ((6R,10S)-3-(4-(difluoromethoxy)
pyridin-2-yl)-6,7,9,10-tetrahydro-5H-6,10-epimino
[1,2,4]triazolo[3,4-d][1,5]oxazocin-11-yl)(3-fluoro-
2-(trifluoromethyl)pyridin-4-yl)methanone

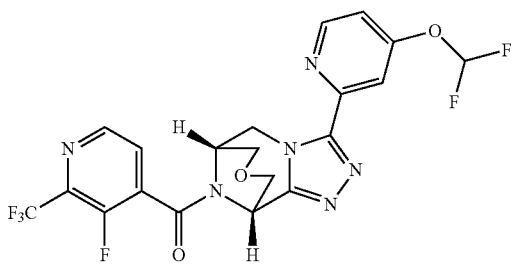 [SMILES: O=C(c1ccnc(C(F)(F)F)c1F)N1[C@H]2COC[C@@H]1c1nnc(-c3cc(OC(F)F)ccn3)n1C2]

Example 156: (2,3-dichlorophenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone

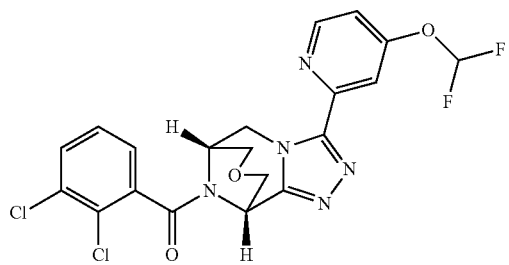 [SMILES: O=C(c1cccc(Cl)c1Cl)N1[C@H]2COC[C@@H]1c1nnc(-c3cc(OC(F)F)ccn3)n1C2]

Example 157: (2-chloro-3-(trifluoromethyl)phenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone

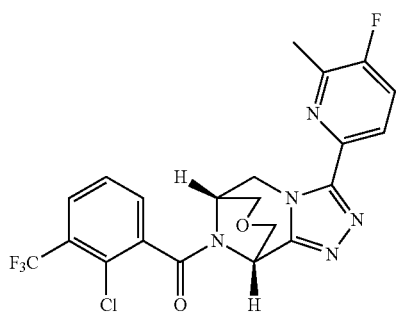

Example 158: (2,3-dichloro-4-fluorophenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone

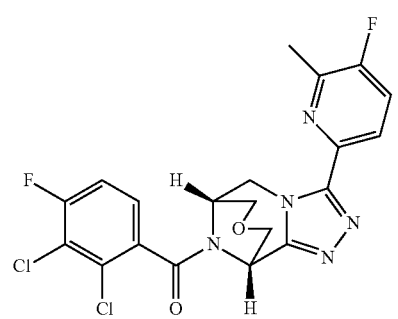 [SMILES: Cc1nc(-c2nnc3n2C[C@@H]2COC[C@H]3N2C(=O)c2ccc(F)c(Cl)c2Cl)ccc1F]

Example 159: ((6R,10S)-3-(5-fluoro-6-methyl pyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone

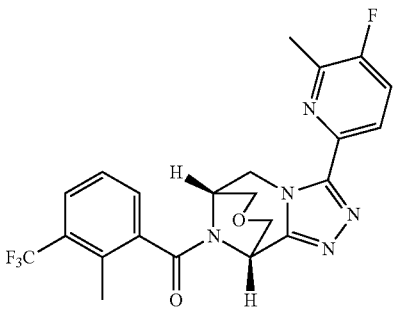 [SMILES: Cc1nc(-c2nnc3n2C[C@@H]2COC[C@H]3N2C(=O)c2cccc(C(F)(F)F)c2C)ccc1F]

Example 160: (2-fluoro-3-(trifluoromethyl)phenyl)((6R,10S)-3-(5-fluoro-6-methyl pyridin-2-yl)-6,7,9,10-tetrahydro-5H-6,10-epimino[1,2,4]triazolo[3,4-d][1,5]oxazocin-11-yl)methanone

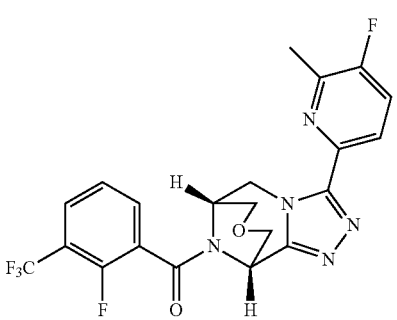 [SMILES: Cc1nc(-c2nnc3n2C[C@@H]2COC[C@H]3N2C(=O)c2cccc(C(F)(F)F)c2F)ccc1F]

Example 161: ((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone

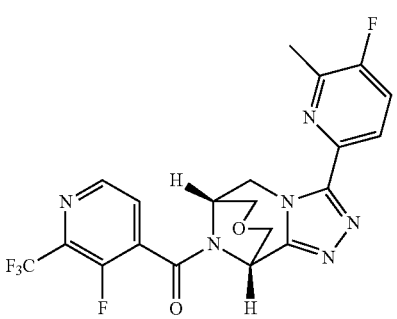 [SMILES: Cc1nc(-c2nnc3n2C[C@@H]2COC[C@H]3N2C(=O)c2ccnc(C(F)(F)F)c2F)ccc1F]

Example 162: (2,3-dichlorophenyl)((6R,10S)-3-(5-fluoro-6-methyl pyridin-2-yl)-6,7,9,10-tetrahydro-5H-6,10-epimino[1,2,4]triazolo[3,4-d][1,5]oxazocin-11-yl)methanone

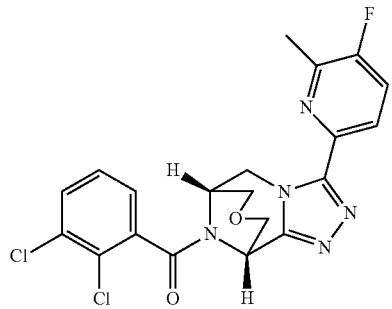 [SMILES: Cc1nc(-c2nnc3n2C[C@@H]2COC[C@H]3N2C(=O)c2cccc(Cl)c2Cl)ccc1F]

Example 163: (2-chloro-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone

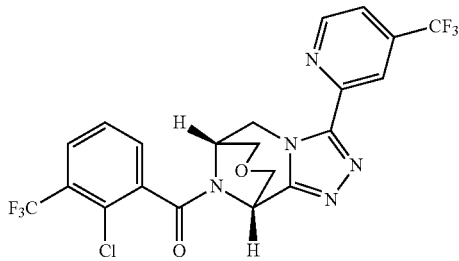 [SMILES: O=C(c1cccc(C(F)(F)F)c1Cl)N1[C@H]2COC[C@@H]1c1nnc(-c3cc(C(F)(F)F)ccn3)n1C2]

Example 164: (2,3-dichloro-4-fluorophenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone

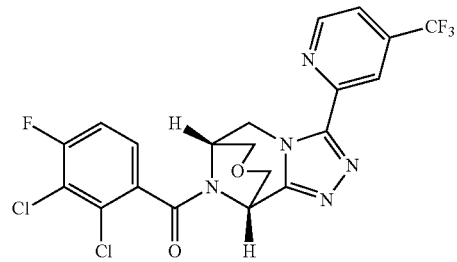 [SMILES: O=C(c1ccc(F)c(Cl)c1Cl)N1[C@H]2COC[C@@H]1c1nnc(-c3cc(C(F)(F)F)ccn3)n1C2]

Example 165: (2-methyl-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone

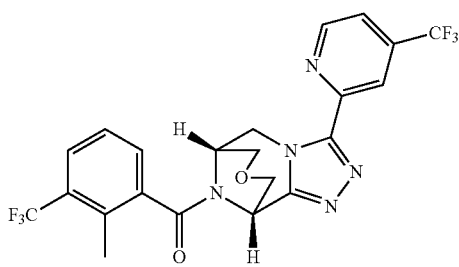

Example 166: (2-fluoro-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone

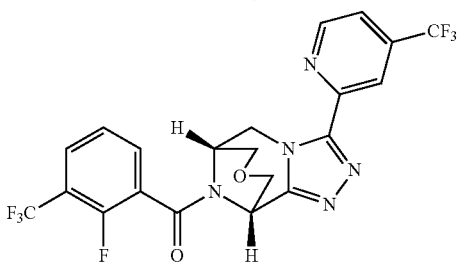 [SMILES: O=C(c1cccc(C(F)(F)F)c1F)N1[C@H]2COC[C@@H]1c1nnc(-c3cc(C(F)(F)F)ccn3)n1C2]

Example 167: (3-fluoro-2-(trifluoromethyl)pyridin-4-yl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone

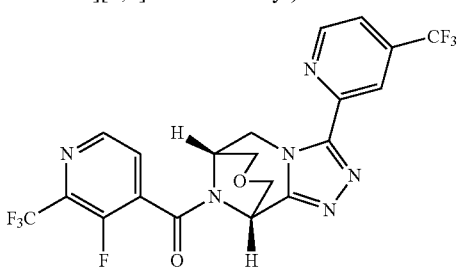

Example 168: (2,3-dichlorophenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone

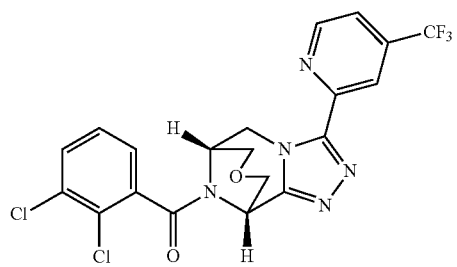 [SMILES: O=C(c1cccc(Cl)c1Cl)N1[C@H]2COC[C@@H]1c1nnc(-c3cc(C(F)(F)F)ccn3)n1C2]

Example 169: (2-chloro-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone

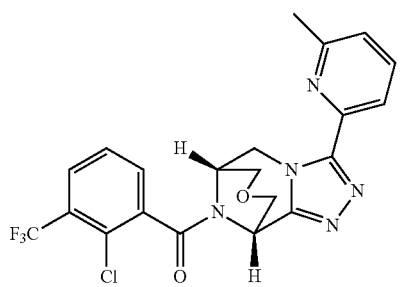 [SMILES: Cc1cccc(-c2nnc3n2C[C@@H]2COC[C@H]3N2C(=O)c2cccc(C(F)(F)F)c2Cl)n1]

Example 170: (2,3-dichloro-4-fluorophenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone

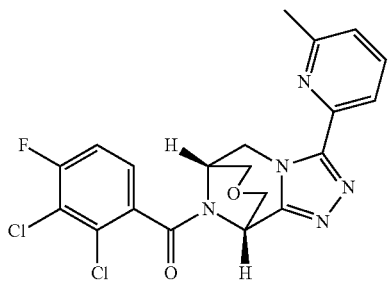 [SMILES: Cc1cccc(-c2nnc3n2C[C@@H]2COC[C@H]3N2C(=O)c2ccc(F)c(Cl)c2Cl)n1]

Example 171: (2-methyl-3-(trifluoromethyl)phenyl)((6R,10S)-3-(6-methyl pyridin-2-yl)-6,7,9,10-tetrahydro-5H-6,10-epimino[1,2,4]triazolo[3,4-d][1,5]oxazocin-11-yl)methanone

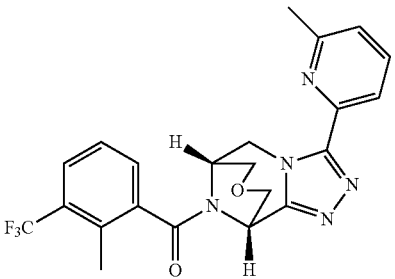

Example 172: (2-fluoro-3-(trifluoromethyl)phenyl)((6R,10S)-3-(6-methyl pyridin-2-yl)-6,7,9,10-tetrahydro-5H-6,10-epimino[1,2,4]triazolo[3,4-d][1,5]oxazocin-11-yl)methanone

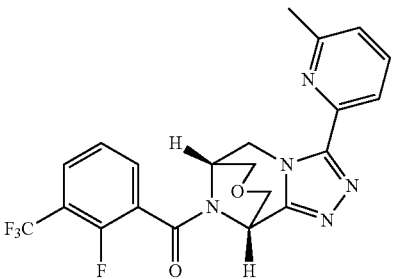 [SMILES: Cc1cccc(-c2nnc3n2C[C@@H]2COC[C@H]3N2C(=O)c2cccc(C(F)(F)F)c2F)n1]

Example 173: (3-fluoro-2-(trifluoromethyl)pyridin-4-yl)((6R,10S)-3-(6-methyl pyridin-2-yl)-6,7,9,10-tetrahydro-5H-6,10-epimino[1,2,4]triazolo[3,4-d][1,5]oxazocin-11-yl)methanone Example 174: (2,3-dichlorophenyl)((6R,10S)-3-(6-methyl pyridin-2-yl)-6,7,9,10-tetrahydro-5H-6,10-epimino[1,2,4]triazolo[3,4-d][1,5]oxazocin-11-yl)methanone

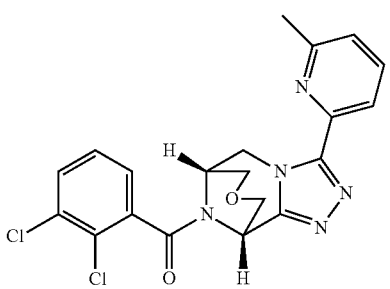 [SMILES: Cc1cccc(-c2nnc3n2C[C@@H]2COC[C@H]3N2C(=O)c2cccc(Cl)c2Cl)n1]

Example 175: (2-chloro-3-(trifluoromethyl)phenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone

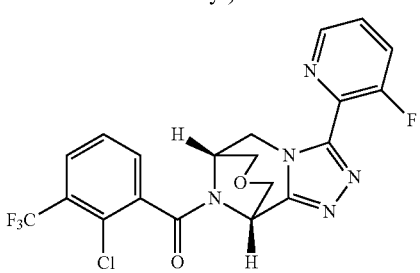

Example 176: (2,3-dichloro-4-fluorophenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone

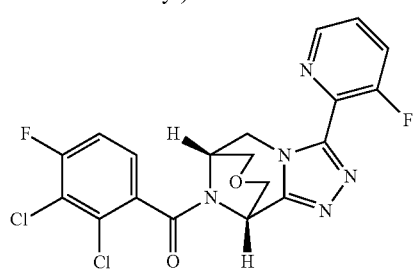

Example 177: ((6R,10S)-3-(3-fluoropyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone

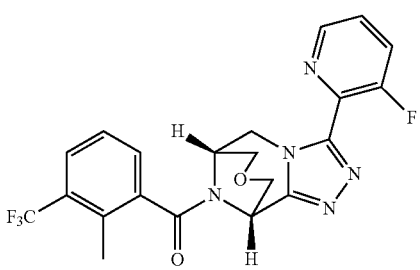 [SMILES: O=C(c1cccc(C(F)(F)F)c1Cl)N1[C@H]2COC[C@@H]1c1nnc(-c3ncccc3F)n1C2]

Example 178: (2-fluoro-3-(trifluoromethyl)phenyl)
((6R,10S)-3-(3-fluoropyridin-2-yl)-6,7,9,10-tetra-
hydro-5H-6,10-epimino[1,2,4]triazolo[3,4-d][1,5]
oxazocin-11-yl)methanone

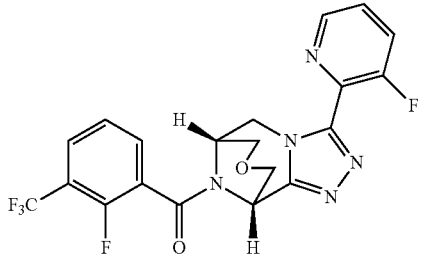 [SMILES: O=C(c1cccc(C(F)(F)F)c1F)N1[C@H]2COC[C@@H]1c1nnc(-c3ncccc3F)n1C2]

Example 179: (3-fluoro-2-(trifluoromethyl)pyridin-
4-yl)((6R,10S)-3-(3-fluoropyridin-2-yl)-6,7,9,10-
tetrahydro-5H-6,10-epimino[1,2,4]triazolo[3,4-d][1,
5]oxazocin-11-yl)methanone

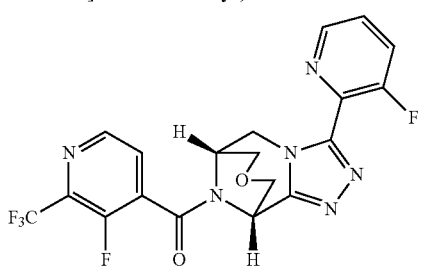

Example 180: (2,3-dichlorophenyl)((6R,10S)-3-(3-
fluoropyridin-2-yl)-6,7,9,10-tetrahydro-5H-6,10-
epimino[1,2,4]triazolo[3,4-d][1,5]oxazocin-11-yl)
methanone

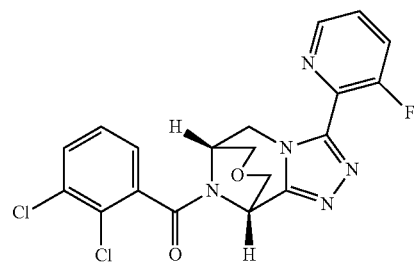 [SMILES: O=C(c1cccc(Cl)c1Cl)N1[C@H]2COC[C@@H]1c1nnc(-c3ncccc3F)n1C2]

Example 181: (2-chloro-3-(trifluoromethyl)phenyl)
((6R,10S)-3-(thiazol-2-yl)-6,7,9,10-tetrahydro-5H-6,
10-epimino[1,2,4]triazolo[3,4-d][1,5]oxazocin-11-
yl)methanone

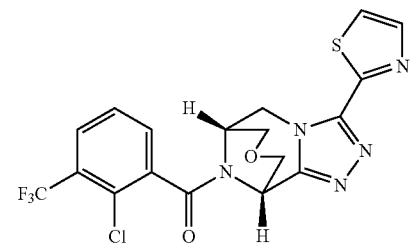 [SMILES: O=C(c1cccc(C(F)(F)F)c1Cl)N1[C@H]2COC[C@@H]1c1nnc(-c3nccs3)n1C2]

Example 182: (2,3-dichloro-4-fluorophenyl)((6R,
10S)-3-(thiazol-2-yl)-6,7,9,10-tetrahydro-5H-6,10-
epimino[1,2,4]triazolo[3,4-d][1,5]oxazocin-11-yl)
methanone

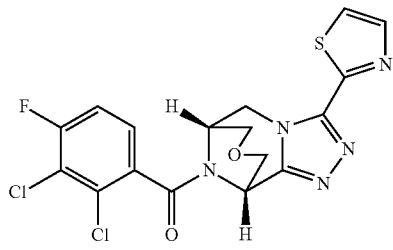 [SMILES: O=C(c1ccc(F)c(Cl)c1Cl)N1[C@H]2COC[C@@H]1c1nnc(-c3nccs3)n1C2]

Example 183: (2-methyl-3-(trifluoromethyl)phenyl)
((6R,10S)-3-(thiazol-2-yl)-6,7,9,10-tetrahydro-5H-6,
10-epimino[1,2,4]triazolo[3,4-d][1,5]oxazocin-11-
yl)methanone

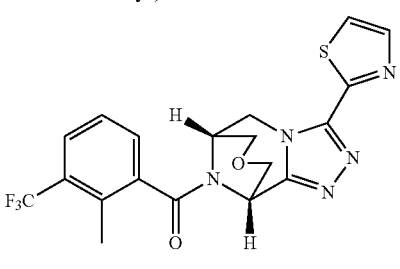

Example 184: (2-fluoro-3-(trifluoromethyl)phenyl)
((6R,10S)-3-(thiazol-2-yl)-6,7,9,10-tetrahydro-5H-6,
10-epimino[1,2,4]triazolo[3,4-d][1,5]oxazocin-11-
yl)methanone

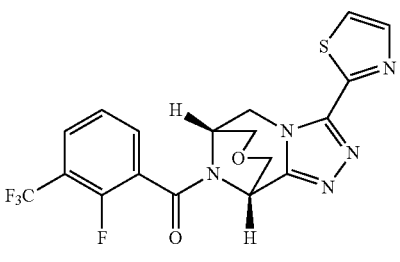 [SMILES: O=C(c1cccc(C(F)(F)F)c1F)N1[C@H]2COC[C@@H]1c1nnc(-c3nccs3)n1C2]

Example 185: (3-fluoro-2-(trifluoromethyl)pyridin-
4-yl)((6R,10S)-3-(thiazol-2-yl)-6,7,9,10-tetrahydro-
5H-6,10-epimino[1,2,4]triazolo[3,4-d][1,5]oxazocin-
11-yl)methanone

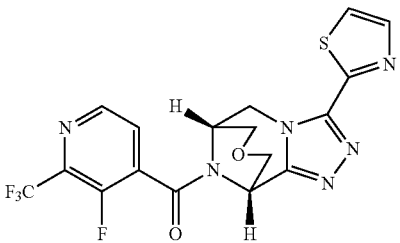 [SMILES: O=C(c1ccnc(C(F)(F)F)c1F)N1[C@H]2COC[C@@H]1c1nnc(-c3nccs3)n1C2]

Example 186: (2,3-dichlorophenyl)((6R,10S)-3-(thiazol-2-yl)-6,7,9,10-tetrahydro-5H-6,10-epimino[1,2,4]triazolo[3,4-d][1,5]oxazocin-11-yl)methanone

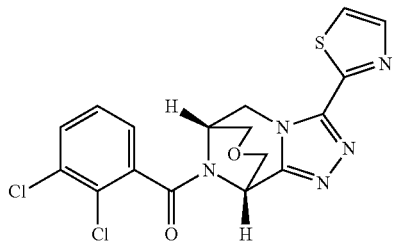 [SMILES: O=C(c1cccc(Cl)c1Cl)N1[C@H]2COC[C@@H]1c1nnc(-c3nccs3)n1C2]

Example 187: (2-chloro-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone

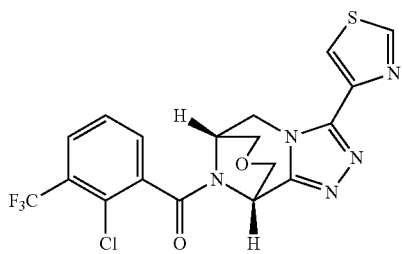 [SMILES: O=C(c1cccc(C(F)(F)F)c1Cl)N1[C@H]2COC[C@@H]1c1nnc(-c3cscn3)n1C2]

Example 188: (2,3-dichloro-4-fluorophenyl)((6R,10S)-3-(thiazol-4-yl)-6,7,9,10-tetrahydro-5H-6,10-epimino[1,2,4]triazolo[3,4-d][1,5]oxazocin-11-yl)methanone

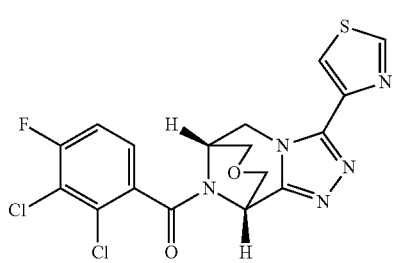 [SMILES: O=C(c1ccc(F)c(Cl)c1Cl)N1[C@H]2COC[C@@H]1c1nnc(-c3cscn3)n1C2]

Example 189: (2-methyl-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone

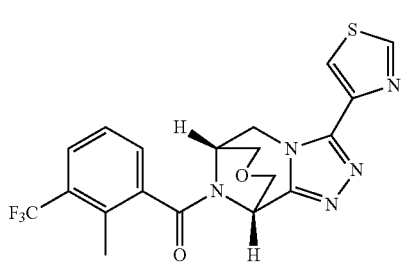

Example 190: (2-fluoro-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone

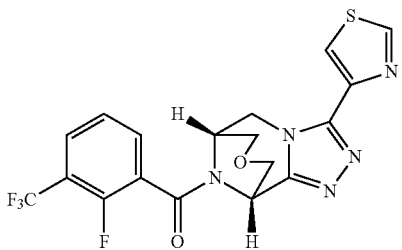 [SMILES: Cc1c(C(=O)N2[C@H]3COC[C@@H]2c2nnc(-c4cscn4)n2C3)cccc1C(F)(F)F]

Example 191: (3-fluoro-2-(trifluoromethyl)pyridin-4-yl)((6R,10S)-3-(thiazol-4-yl)-6,7,9,10-tetrahydro-5H-6,10-epimino[1,2,4]triazolo[3,4-d][1,5]oxazocin-11-yl)methanone

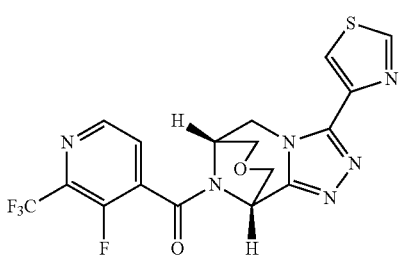 [SMILES: O=C(c1ccnc(C(F)(F)F)c1F)N1[C@H]2COC[C@@H]1c1nnc(-c3cscn3)n1C2]

Example 192: (2,3-dichlorophenyl)((6R,10S)-3-(thiazol-4-yl)-6,7,9,10-tetrahydro-5H-6,10-epimino[1,2,4]triazolo[3,4-d][1,5]oxazocin-11-yl)methanone

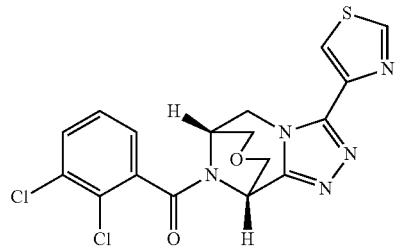 [SMILES: O=C(c1cccc(Cl)c1Cl)N1[C@H]2COC[C@@H]1c1nnc(-c3cscn3)n1C2]

Intermediate K: tert-Butyl (1S,5R)-2-oxo-3,9-diazabicyclo[3.3.1]nonane-9-carboxylate

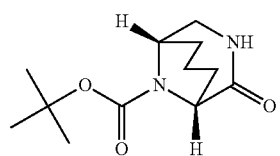 [SMILES: CC(C)(C)OC(=O)N1[C@H]2CCC[C@@H]1C(=O)NC2]

tert-Butyl (1S,5R)-2-oxo-3,9-diazabicyclo[3.3.1]nonane-9-carboxylate, absolute configuration unknown, was obtained as a single enantiomer by Chiral SFC purification of Intermediate A performed using a CHIRALPAK AD-H (250×20 mm) column and a mobile phase of 70% $CO_2$, 30% MeOH. The enantiomeric purity was confirmed by analytical SFC using a Chiralpak AD-H (250×4.6 mm) column and a mobile phase of 70% $CO_2$, 30% MeOH containing 0.3% $iPrNH_2$ over 7 minutes. (100% single enantiomer, 3.14 min retention time). MS (ESI): mass calcd. $C_{12}H_{20}N_2O_3$, 240.15; m/z found, 241.1 [M+H]$^+$.

Intermediate L: tert-Butyl (1S, 5R)-2-thioxo-3,9-diazabicyclo[3.3.1]nonane-9-carboxylate

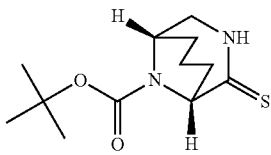 [SMILES: CC(C)(C)OC(=O)N1[C@H]2CCC[C@@H]1C(=S)NC2]

The title compound was prepared in a manner analogous to Intermediate B substituting Intermediate K for Intermediate A. MS (ESI): mass calcd. $C_{12}H_{20}N_2O_2S$, 256.12; m/z found, 257.0 [M+H]$^+$. 1H NMR (500 MHz, CDCl$_3$): 8.53-8.25 (m, 1H), 5.22-4.97 (m, 1H), 4.63-4.35 (m, 1H), 3.28-3.17 (m, 1H), 2.21-2.12 (m, 1H), 1.91-1.62 (m, 5H), 1.47 (s, 9H), 3.81-3.65 (m, 1H).

Intermediate M: (E/Z)(1S,5R)-(9-(tert-butoxycarbonyl)-3,9-diazabicyclo[3.3.1]nonan-2-ylidene)(methyl)sulfonium Iodide

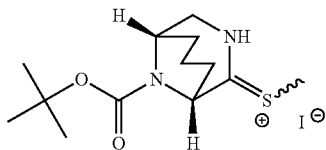

The title compound was prepared in a manner analogous to Intermediate C substituting Intermediate L for Intermediate B. MS (ESI): mass calcd. $C_{12}H_{20}N_2O_2S$, 256.12; m/z found, 257.0 [M+H]$^+$.

Intermediate N: 5-fluoro-6-methylpicolinohydrazide

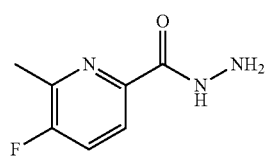

The title compound was prepared in a manner analogous to Intermediate F substituting 5-fluoro-6-methylpicolinonitrile for 5-fluoropyrimidine-2-carbonitrile. MS (ESI): mass calcd. $C_7H_8FN_3O$, 169.07; m/z found, 170.0 [M+H]$^+$. 1H NMR (500 MHz, CDCl$_3$): 8.86 (s, 1H), 8.02 (dd, J=8.5, 4.0 Hz, 1H), 7.44 (t, J=8.6 Hz, 1H), 4.17-3.92 (m, 2H), 2.53 (d, J=2.9 Hz, 3H).

Intermediate O: 4-methylpicolinohydrazide

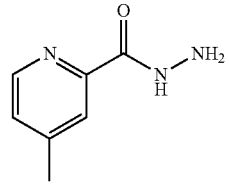

The title compound was prepared in a manner analogous to Intermediate D substituting methyl 4-methylpicolinate for methyl pyrimidine-2-carboxylate. MS (ESI): mass calcd. $C_7H_9N_3O$, 151.07; m/z found, 152.1 [M+H]$^+$. 1H NMR (500 MHz, CDCl$_3$): 8.97 (s, 1H), 8.43-8.37 (m, 1H), 8.02-7.96 (m, 1H), 7.26-7.24 (m, 1H), 4.07 (s, 2H), 2.43 (s, 3H).

Intermediate P: pyridazine-3-carbohydrazide

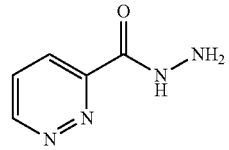

The title compound was prepared in a manner analogous to Intermediate D substituting methyl pyridazine-3-carboxylate for methyl pyrimidine-2-carboxylate. MS (ESI): mass calcd. for $C_5H_6N_4O$, 138.1; m/z found, 139.1 [M+H]$^+$. 1H NMR (400 MHz, DMSO-d6): 10.45 (s, 1H), 9.39 (dd, J=5.0, 1.7 Hz, 1H), 8.17 (dd, J=8.4, 1.7 Hz, 1H), 7.91 (dd, J=8.4, 5.0 Hz, 1H), 4.71 (s, 2H).

Intermediate Q: 4-(trifluoromethyl)picolinohydrazide

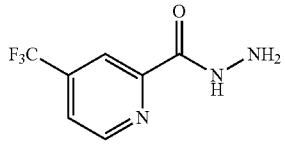 [SMILES: NNC(=O)c1cc(C(F)(F)F)ccn1]

The title compound was prepared in a manner analogous to Intermediate D substituting methyl 4-(trifluoromethyl)picolinate for methyl pyrimidine-2-carboxylate. MS (ESI): mass calcd. for $C_7H_6F_3N_3O$, 205.04; m/z found, 206.0 [M+H]$^+$. 1H NMR (400 MHz, CDCl$_3$): 8.96 (s, 1H), 8.79-8.73 (m, 1H), 8.45-8.37 (m, 1H), 7.72-7.64 (m, 1H), 4.12 (d, J=4.6 Hz, 2H).

Intermediate R: pyrimidine-4-carbohydrazide

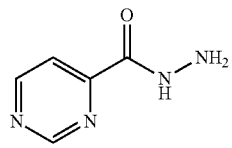

The title compound was prepared in a manner analogous to Intermediate D substituting ethyl pyrimidine-4-carboxylate for methyl pyrimidine-2-carboxylate. MS (ESI): mass calcd. for $C_5H_6N_4O$, 138.1; m/z found, 139.1 $[M+H]^+$. 1H NMR (400 MHz, DMSO-d6): 10.31 (s, 1H), 9.27 (d, J=1.3 Hz, 1H), 9.03 (d, J=5.1 Hz, 1H), 7.97 (dd, J=5.1, 1.4 Hz, 1H), 4.72 (s, 2H).

Example 193: (6R,10S)-11-{[2-Chloro-3-(trifluoromethyl)phenyl]carbonyl}-3-(5-fluoro-6-methylpyridin-2-yl)-5,6,7,8,9,10-hexahydro-6,10-epimino[1,2,4]triazolo[4,3-a]azocine

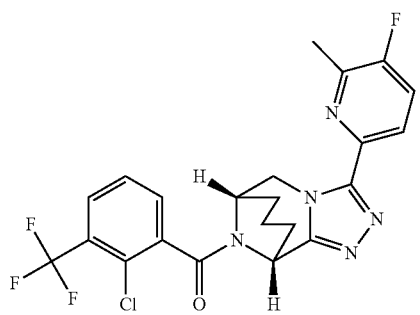 [SMILES: Cc1nc(-c2nnc3n2C[C@@H]2CCC[C@H]3N2C(=O)c2cccc(C(F)(F)F)c2Cl)ccc1F]

The title compound was prepared in a manner analogous to Example 1 substituting Intermediate M for Intermediate C and Intermediate N for Intermediate D in step a. MS (ESI): mass calcd. $C_{22}H_{18}ClF_4N_5O$, 479.1; m/z found, 479.9 $[M+H]^+$. 1H NMR (500 MHz, CDCl$_3$): 8.27-8.18 (m, 1H), 7.82-7.77 (m, 1H), 7.60-7.27 (m, 3H), 6.44-5.44 (m, 1H), 5.04-4.01 (m, 3H), 2.63-2.48 (m, 3H), 2.23-1.73 (m, 5H), 1.45-1.31 (m, 1H).

Example 194: (6R,10S)-11-{[2-Chloro-3-(trifluoromethyl)phenyl]carbonyl}-3-(4-methylpyridin-2-yl)-5,6,7,8,9,10-hexahydro-6,10-epimino[1,2,4]triazolo[4,3-a]azocine

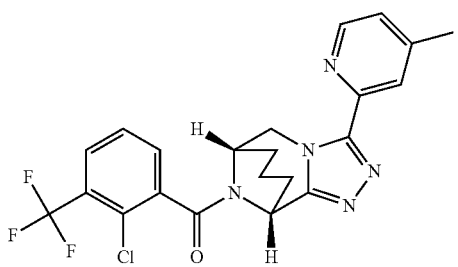 [SMILES: Cc1ccnc(-c2nnc3n2C[C@@H]2CCC[C@H]3N2C(=O)c2cccc(C(F)(F)F)c2Cl)c1]

The title compound was prepared in a manner analogous to Example 1 substituting Intermediate M for Intermediate C and Intermediate O for Intermediate D in step a. MS (ESI): mass calcd. $C_{22}H_{19}ClF_3N_5O$, 461.12; m/z found, 461.9 $[M+H]^+$. 1H NMR (500 MHz, CDCl$_3$): 8.55-8.39 (m, 1H), 8.25-8.16 (m, 1H), 7.83-7.76 (m, 1H), 7.60-7.27 (m, 2H), 7.22-7.12 (m, 1H), 6.46-5.41 (m, 1H), 5.07-3.95 (m, 3H), 2.48-2.40 (m, 3H), 2.22-2.05 (m, 2H), 2.03-1.72 (m, 3H), 1.46-1.33 (m, 1H).

Example 195: (6R,10S)-11-{[2-Chloro-3-(trifluoromethyl)phenyl]carbonyl}-3-pyridazin-3-yl-5,6,7,8,9,10-hexahydro-6,10-epimino[1,2,4]triazolo[4,3-a]azocine

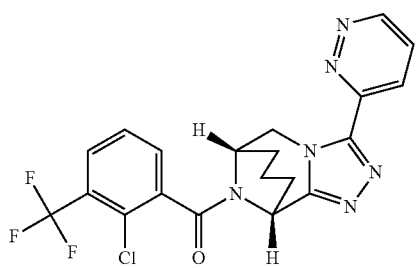 [SMILES: O=C(c1cccc(C(F)(F)F)c1Cl)N1[C@H]2CCC[C@@H]1c1nnc(-c3cccnn3)n1C2]

The title compound was prepared in a manner analogous to Example 1 substituting Intermediate M for Intermediate C and Intermediate P for Intermediate D in step a. MS (ESI): mass calcd. $C_{20}H_{16}ClF_3N_6O$, 448.10; m/z found, 448.9 $[M+H]^+$. 1H NMR (500 MHz, CDCl$_3$): 9.29-9.19 (m, 1H), 8.61-8.50 (m, 1H), 7.86-7.77 (m, 1H), 7.71-7.64 (m, 1H), 7.61-7.27 (m, 2H), 6.49-5.47 (m, 1H), 5.13-3.99 (m, 3H), 2.28-2.06 (m, 2H), 2.04-1.76 (m, 3H), 1.47-1.28 (m, 1H).

Example 196: (6R,10S)-11-{[2-Chloro-3-(trifluoromethyl)phenyl]carbonyl}-3-[4-(trifluoromethyl)pyridin-2-yl]-5,6,7,8,9,10-hexahydro-6,10-epimino[1,2,4]triazolo[4,3-a]azocine

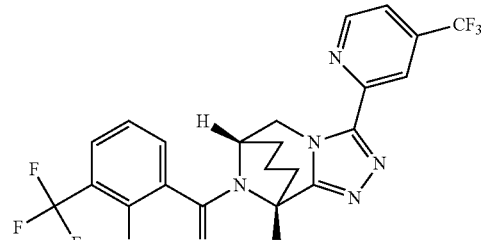

The title compound was prepared in a manner analogous to Example 1 substituting Intermediate M for Intermediate C and Intermediate Q for Intermediate D in step a. MS (ESI): mass calcd. $C_{22}H_{16}ClF_6N_5O$, 515.09; m/z found, 515.8 $[M+H]^+$. 1H NMR (500 MHz, CDCl$_3$): 8.88-8.73 (m, 1H), 8.69-8.61 (m, 1H), 7.84-7.77 (m, 1H), 7.62-7.27 (m, 3H), 6.48-5.44 (m, 1H), 5.08-4.00 (m, 3H), 2.26-1.76 (m, 5H), 1.45-1.29 (m, 1H).

Example 197: (6R,10S)-11-{[2-Chloro-3-(trifluoromethyl)phenyl]carbonyl}-3-pyrimidin-4-yl-5,6,7,8,9,10-hexahydro-6,10-epimino[1,2,4]triazolo[4,3-a]azocine

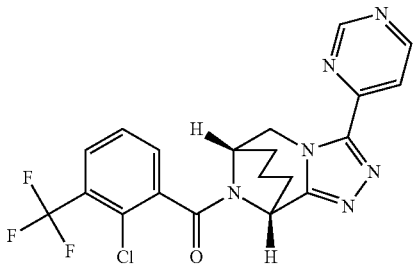 [SMILES: O=C(c1cccc(C(F)(F)F)c1Cl)N1[C@H]2CCC[C@@H]1c1nnc(-c3ccncn3)n1C2]

The title compound was prepared in a manner analogous to Example 1 substituting Intermediate M for Intermediate C and Intermediate R for Intermediate D in step a. MS (ESI): mass calcd. $C_{20}H_{16}ClF_3N_6O$, 448.10; m/z found, 448.9 [M+H]$^+$. 1H NMR (500 MHz, CDCl$_3$): 9.34-9.19 (m, 1H), 8.94-8.86 (m, 1H), 8.38-8.29 (m, 1H), 7.85-7.78 (m, 1H), 7.61-7.27 (m, 2H), 6.48-5.45 (m, 1H), 5.09-4.00 (m, 3H), 2.26-1.76 (m, 5H), 1.43-1.28 (m, 1H).

Example 198: (6R,10S)-11-{[3-Fluoro-2-(trifluoromethyl)pyridin-4-yl]carbonyl}-3-pyridin-2-yl-5,6,7,8,9,10-hexahydro-6,10-epimino[1,2,4]triazolo[4,3-a]azocine

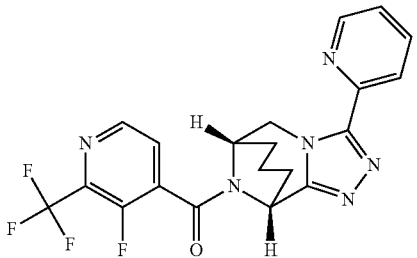

Example 198, Step a: (6R,10S)-tert-butyl 3-(pyridin-2-yl)-5,6,7,8,9,10-hexahydro-6,10-epimino[1,2,4]triazolo[4,3-a]azocine-11-carboxylate To a round bottom flask was added Intermediate M (1.50 g, 3.766 mmol), 2-picolinyl hydrazide (579 mg, 4.143 mmol) and n-BuOH (15 mL). To this suspension was added KOtBu (465 mg, 4.143 mmol). After 30 min at room temperature, the mixture was heated at 120° C. for 40 h. The mixture was concentrated in vacuo and taken on to the next step without further purification.

Example 198, Step b: (6R,10S)-3-(pyridin-2-yl)-5,6,7,8,9,10-hexahydro-6,10-epimino[1,2,4]triazolo[4,3-a]azocine To a solution of the product of Example 198, step a (1.29 g, 3.766 mmol) in MeOH (8 mL) was added 4 M HCl in dioxane (10 mL). The mixture was stirred overnight at room temperature and then concentrated in vacuo. The residue was chromatographed on SiO$_2$ eluting with 2 M NH$_3$ in MeOH/DCM to afford the title compound as a pale yellow solid (733 mg, 81%). MS (ESI): mass calcd. $C_{13}H_{15}N_5$, 241.13; m/z found, 242.0 [M+H]$^+$. 1H NMR (500 MHz, CDCl$_3$): 8.65-8.60 (m, 1H), 8.38-8.31 (m, 1H), 7.85-7.79 (m, 1H), 7.35-7.29 (m, 1H), 4.69-4.51 (m, 3H), 3.68-3.62 (m, 1H), 2.09-1.96 (m, 4H), 1.84-1.78 (m, 1H), 1.70-1.62 (m, 1H), 1.33-1.21 (m, 1H).

Example 198, Step c: (6R,10S)-11-{[3-Fluoro-2-(trifluoromethyl)pyridin-4-yl]carbonyl}-3-pyridin-2-yl-5,6,7,8,9,10-hexahydro-6,10-epimino[1,2,4]triazolo[4,3-a]azocine To a solution of the product of Example 198, step b (135 mg, 0.560 mmol) in DCM (6 mL) was added EDCl (161 mg, 0.839 mmol), HOBt (53 mg, 0.392 mmol), 3-fluoro-2-trifluoromethyl-isonicotinic acid (129 mg, 0.615 mmol) followed by TEA (0.156 mL, 1.12 mmol). The reaction was stirred at room temperature overnight, the volume reduced by half in vacuo, and then loaded directly on a SiO$_2$ column eluting with IPA/EtOAc/Hex to afford the title compound (219 mg, 91%). MS (ESI): mass calcd. $C_{20}H_{16}F_4N_6O$, 432.13; m/z found, 432.9 [M+H]$^+$. 1H NMR (400 MHz, CDCl$_3$): 8.70-8.56 (m, 2H), 8.42-8.32 (m, 1H), 7.90-7.82 (m, 1H), 7.67-7.45 (m, 1H), 7.41-7.32 (m, 1H), 6.41-5.37 (m, 1H), 5.11-4.04 (m, 3H), 2.24-1.77 (m, 5H), 1.50-1.35 (m, 1H).

Example 199: (6R,10S)-11-{[3-Chloro-2-(trifluoromethyl)pyridin-4-yl]carbonyl}-3-pyridin-2-yl-5,6,7,8,9,10-hexahydro-6,10-epimino[1,2,4]triazolo[4,3-a]azocine

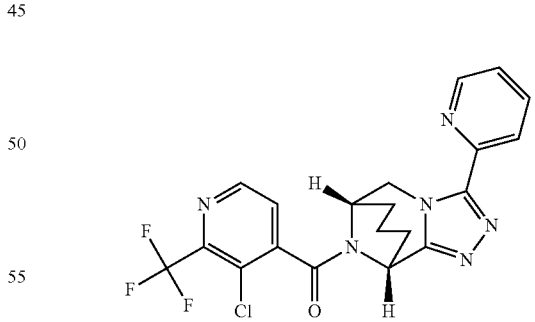

The title compound was prepared in a manner analogous to Example 198 substituting 3-chloro-2-(trifluoromethyl) isonicotinic acid for 3-fluoro-2-trifluoromethyl-isonicotinic acid in step c. MS (ESI): mass calcd. $C_{20}H_{16}ClF_3N_6O$, 448.10; m/z found, 448.9 [M+H]$^+$. 1H NMR (500 MHz, CDCl$_3$): 8.75-8.55 (m, 2H), 8.41-8.33 (m, 1H), 7.89-7.83 (m, 1H), 7.55-7.23 (m, 2H), 6.43-5.40 (m, 1H), 5.01-3.92 (m, 3H), 2.26-2.00 (m, 3H), 1.94-1.76 (m, 2H), 1.50-1.33 (m, 1H).

Example 200: (6R,10S)-11-{[2-Chloro-4-fluoro-3-(trifluoromethyl)phenyl]carbonyl}-3-pyridin-2-yl-5,6,7,8,9,10-hexahydro-6,10-epimino[1,2,4]triazolo[4,3-a]azocine

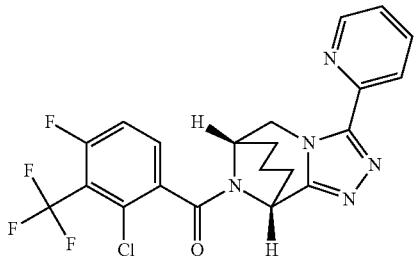 [SMILES: O=C(c1ccc(F)c(C(F)(F)F)c1Cl)N1[C@H]2CCC[C@@H]1c1nnc(-c3ccccn3)n1C2]

The title compound was prepared in a manner analogous to Example 198 substituting 2-chloro-4-fluoro-3-(trifluoromethyl)benzoic acid for 3-fluoro-2-trifluoromethyl-isonicotinic acid in step c. MS (ESI): mass calcd. $C_{21}H_{16}ClF_4N_5O$, 465.09; m/z found, 465.9 [M+H]$^+$. 1H NMR (500 MHz, CDCl$_3$): 8.69-8.55 (m, 1H), 8.41-8.33 (m, 1H), 7.89-7.82 (m, 1H), 7.59-7.27 (m, 2H), 7.26-7.13 (m, 1H), 6.43-5.41 (m, 1H), 5.05-3.98 (m, 3H), 2.23-1.97 (m, 3H), 1.90-1.74 (m, 2H), 1.48-1.32 (m, 1H).

Example 201: (6R,10S)-11-{[2-Methyl-3-(trifluoromethyl)phenyl]carbonyl}-3-pyridin-2-yl-5,6,7,8,9,10-hexahydro-6,10-epimino[1,2,4]triazolo[4,3-a]azocine

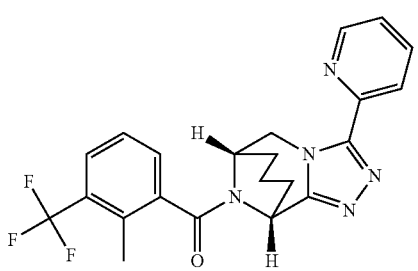

The title compound was prepared in a manner analogous to Example 198 substituting 2-methyl-3-(trifluoromethyl)benzoic acid for 3-fluoro-2-trifluoromethyl-isonicotinic acid in step c. MS (ESI): mass calcd. $C_{22}H_{20}F_3N_5O$, 427.2; m/z found, 428.0 [M+H]$^+$. 1H NMR (500 MHz, CDCl$_3$): 8.70-8.56 (m, 1H), 8.42-8.34 (m, 1H), 7.90-7.67 (m, 2H), 7.50-7.27 (m, 3H), 6.48-5.45 (m, 1H), 5.13-4.00 (m, 3H), 2.71-1.83 (m, 8H), 1.47-1.32 (m, 1H).

Example 202: (6R,10S)-11-[(2,4-Dichloro-3-fluorophenyl)carbonyl]-3-pyridin-2-yl-5,6,7,8,9,10-hexahydro-6,10-epimino[1,2,4]triazolo[4,3-a]azocine

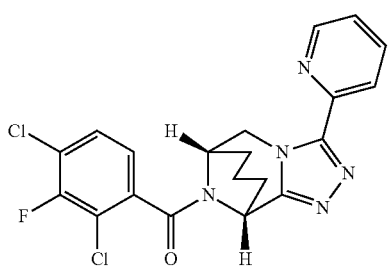 [SMILES: O=C(c1ccc(Cl)c(F)c1Cl)N1[C@H]2CCC[C@@H]1c1nnc(-c3ccccn3)n1C2]

The title compound was prepared in a manner analogous to Example 198 substituting 2,4-dichloro-3-fluorobenzoic acid for 3-fluoro-2-trifluoromethyl-isonicotinic acid in step c. MS (ESI): mass calcd. $C_{20}H_{16}Cl_2FN_5O$, 431.07; m/z found, 431.9 [M+H]$^+$. 1H NMR (500 MHz, CDCl$_3$) δ 8.69-8.55 (m, 1H), 8.41-8.32 (m, 1H), 7.89-7.81 (m, 1H), 7.48-7.31 (m, 2H), 7.18-6.84 (m, 1H), 6.41-5.40 (m, 1H), 5.09-3.99 (m, 3H), 2.21-1.73 (m, 5H), 1.46-1.32 (m, 1H).

Example 203: (6R,10S)-11-[(2,3-Dichloro-4-fluorophenyl)carbonyl]-3-pyridin-2-yl-5,6,7,8,9,10-hexahydro-6,10-epimino[1,2,4]triazolo[4,3-a]azocine

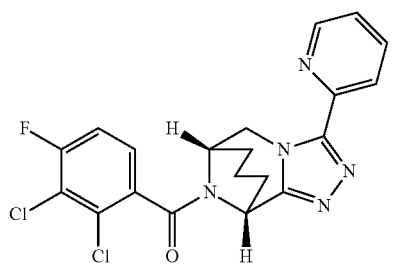

The title compound was prepared in a manner analogous to Example 198 substituting 2,3-dichloro-4-fluorobenzoic acid for 3-fluoro-2-trifluoromethyl-isonicotinic acid in step c. MS (ESI): mass calcd. $C_{20}H_{16}Cl_2FN_5O$, 431.07; m/z found, 431.9 [M+H]$^+$. 1H NMR (500 MHz, CDCl$_3$): 8.69-8.56 (m, 1H), 8.42-8.32 (m, 1H), 7.90-7.82 (m, 1H), 7.40-6.99 (m, 3H), 6.42-5.39 (m, 1H), 5.09-4.00 (m, 3H), 2.23-1.74 (m, 5H), 1.44-1.31 (m, 1H).

Pharmacological Examples

The in vitro affinity of the compounds of the invention for the rat and human P2X7 receptor was determined using one or more of the following assays: a human peripheral blood mononuclear cells (PBMCs), a human whole blood assay, a Ca$^{2+}$ flux and radioligand binding assay in recombinant human P2X7 cells and recombinant rat P2X7 cells. In Tables 1 and 2, when the data cell has the term NT or has been left blank, it is intended to mean that the compound was not tested in that assay. The data represented in Tables 1 and 2 may represent a value from a single determination or when the experiment was run more than once, the data represent averages from between 2-12 runs.

P2X7 Antagonism in Human Peripheral Blood Mononuclear Cells (PBMCs) and Human Whole Blood.

Human blood was collected using a blood donor program. PBMCs were isolated from blood using a Ficoll density gradient technique. Briefly, blood was laid on Ficoll solution and centrifuged at RT for 20 minutes at 2000 rpm. The buffy layer (between red blood cells and plasma) was carefully collected by aspiration, washed with PBS and centrifuged again at 1500 rpm for 15 minutes. The resulting cell pellet was washed and plated on 96 well-plates for experiments. For the Human Whole Blood experiments, 150 μl of human blood was platted on 96 well-plates. Lipopolysaccharide (LPS) (30 ng/ml) was added to each well and incubated for 1 hour. Test compounds were then added and incubated for 30 minutes. The P2X7 agonist, 2'(3')-O-(4-benzoylbenzoyl) adenosine 5'-triphosphate (Bz-ATP) was then added at a final concentration of 0.5 mM (PBMC) or 1 mM (blood). Cells were incubated for an additional 1.5 hours. At that point, supernatant was collected and stored for IL-1β assay using manufacturer's protocol for enzyme-linked immunosorbent assay (ELISA). Data was expressed as percent control, where control is defined as the difference in IL-1β release in LPS+Bz-ATP samples and LPS only samples. Data was plotted as response (% control) versus concentration to generate $IC_{50}$ values. In Tables 1 and 2, this data is represented by PBMC 10 μM (% control) and human whole blood $IC_{50}$ (μM). Data are analyzed and graphed on Graphpad Prism 5. For analysis, each concentration point is averaged from triplicate values and the averaged values are plotted on Graphpad Prism.

P2X7 Antagonism in Recombinant Human P2X7 Cells or Recombinant Rat P2X7 Cells: (a) $Ca^{2+}$ Flux and (b) Radioligand Binding (a) $Ca^{2+}$ Flux:

1321N1 cells expressing the recombinant human or rat P2X7 channel was cultured in HyQ DME/(HyClone/Dulbecco's Modified Eagle Medium) high glucose supplemented with 10% Fetal Bovine Serum (FBS) and appropriate selection marker. Cells were seeded at a density of 25000 cells/well (96-well clear bottom black walled plates) in 100 μl volume/well. On the day of the experiment, cell plates were washed with assay buffer, containing (in mM): 130 NaCl, 2 KCl, 1 $CaCl_2$, 1 $MgCl_2$, 10 HEPES, 5 glucose; pH 7.40 and 300 mOs. After the wash, cells were loaded with the Calcium-4 dye (Molecular Device) and incubated in the dark for 60 minutes. Test compounds were prepared at 250× the test concentration in neat DMSO. Intermediate 96-well compound plates were prepared by transferring 1.2 μL of the compound into 300 μL of assay buffer. A further 3× dilution occurred when transferring 50 μL/well of the compound plate to 100 μL/well in the cell plate. Cells were incubated with test compounds and dye for 30 minutes. Calcium dye fluorescence was monitored in FLIPR as the cells were challenged by adding 50 μL/well of BzATP (final concentration is 250 μM BzATP (human and rat)). The fluorescence change was measured 180 seconds after adding the agonist. Peak fluorescence was plotted as a function of BzATP concentration using Origin 7 software and the resultant $IC_{50}$ is shown in Tables 1 and 2 under the column headings FLIPR (human) $IC_{50}$ (μM) and FLIPR (rat) $IC_{50}$ (μM).

(b) Radioligand Binding:

human or rat P2X7-1321N1 cells were collected and frozen @ −80° C. On the day of the experiment, cell membrane preparations were made according to standard published methods. The total assay volume was 100 μl:10 μl compound (10×)+(b) 40 μl tracer (2.5×)+50 μl membrane (2×). The tracer used for the assay was tritiated A-804598. The compound can be prepared as described in the literature. (Donnelly-Roberts, D. *Neuropharmacology* 2008, 56 (1), 223-229.) Compounds, tracer and membranes were incubated for 1 hour @ 4° C. The assay was terminated by filtration (GF/B filters pre-soaked with 0.3% PEI) and washed with washing buffer (Tris-HCl 50 mM). The $IC_{50}$ generated in the binding assay was corrected for tracer concentration and affinity of the tracer to derive at the affinity ($K_i$) of the test compounds. The data are presented in Tables 1 and 2 under the headings: P2X7 human $K_i$ (μM) and P2X7 rat $K_i$ (μM). Data are analyzed and graphed on Graphpad Prism 5. For analysis, each concentration point is averaged from triplicate values and the averaged values are plotted on Graphpad Prism.

TABLE 1

P2X7 activity of compounds of Formula (I) in a panel of in-vitro assays

| Example No. | PBMC 10 μM (% control) | P2X7 human $K_i$ (μM) | P2X7 rat $K_i$ (μM) | FLIPR (human) $IC_{50}$ (μM) | FLIPR (rat) $IC_{50}$ (μM) | Human whole blood $IC_{50}$ (μM) |
|---|---|---|---|---|---|---|
| 1 | 11.0 | 0.0501 | NT | 0.0038 | 0.0045 | NT |
| 2 | 45.7 | NT | NT | >10 | >10 | NT |
| 3 | 8.9 | 0.0398 | 0.0040 | 0.0096 | 0.0081 | NT |
| 4 | 6.1 | 0.0200 | NT | 0.0953 | 0.1327 | NT |
| 5 | −4.4 | 0.0126 | NT | 0.0634 | 0.0147 | NT |
| 6 | 5.8 | NT | NT | 2.2962 | 2.3227 | NT |
| 7 | 9.9 | 0.0126 | NT | 0.0077 | 0.0157 | NT |
| 8 | 7.3 | 0.0100 | 0.0013 | 0.0097 | 0.0025 | NT |
| 9 | 7.3 | 0.3981 | NT | 0.4819 | 0.1803 | NT |
| 11 | 38.9 | NT | NT | 5.6885 | 14.8252 | NT |
| 12 | −0.8 | 0.0126 | 0.0034 | 0.0133 | 0.0366 | 0.1259 |
| 14 | 2.4 | 0.0174 | NT | 0.0100 | 0.0082 | NT |
| 15 | 89.8 | NT | NT | NT | NT | NT |
| 17 | 84.2 | NT | NT | NT | NT | NT |
| 18 | −9.0 | 0.0138 | NT | 0.0011 | 0.0044 | NT |
| 20 | 104.2 | NT | NT | NT | NT | NT |
| 21 | −2.1 | 0.0501 | NT | 0.0948 | 3.3497 | NT |
| 23 | 8.0 | 0.0240 | 0.0050 | 0.0404 | 0.0560 | NT |
| 24 | 32.7 | NT | NT | 3.6983 | >10 | NT |
| 26 | 9.2 | 0.0304 | 0.0040 | 0.0100 | 0.0014 | 0.0398 |
| 27 | 4.8 | NT | NT | 1.9055 | 1.5417 | NT |
| 29 | 91.4 | NT | NT | NT | NT | NT |
| 30 | 1.4 | 0.0355 | NT | 0.1183 | 2.7733 | NT |
| 32 | 94.5 | NT | NT | NT | NT | NT |
| 33 | −1.0 | 0.0105 | 0.0032 | 0.0134 | 0.0113 | 0.0437 |
| 35 | 82.2 | NT | NT | NT | NT | NT |
| 36 | −1.2 | 0.0107 | NT | 0.0365 | 0.3381 | NT |
| 38 | 101.0 | NT | NT | NT | NT | NT |
| 39 | 5.8 | 0.0251 | NT | 0.0511 | 0.0798 | NT |
| 40 | −1.3 | 0.0219 | 0.0355 | 0.0126 | 10.0000 | NT |
| 41 | −20.0 | 0.0126 | 0.0079 | 0.0063 | 1.5849 | NT |
| 42 | −21.3 | 0.0126 | 0.0079 | 0.0200 | 0.2512 | NT |

TABLE 1-continued

P2X7 activity of compounds of Formula (I) in a panel of in-vitro assays

| Example No. | PBMC 10 µM (% control) | P2X7 human Ki (µM) | P2X7 rat Ki (µM) | FLIPR (human) IC$_{50}$ (µM) | FLIPR (rat) IC$_{50}$ (µM) | Human whole blood IC$_{50}$ (µM) |
|---|---|---|---|---|---|---|
| 43 | −18.6 | 0.0129 | 0.0138 | 0.0200 | 3.9811 | NT |
| 44 | 7.9 | 0.0126 | 0.0126 | 0.0077 | 8.4918 | NT |
| 45 | 6.5 | 0.0126 | 0.0316 | 0.0131 | 15.8125 | NT |
| 46 | 10.0 | 0.0158 | 0.0063 | 0.0152 | 0.2529 | NT |
| 47 | 0.0 | 0.0100 | 0.0063 | 0.0203 | 1.9231 | NT |
| 48 | −0.6 | 0.0398 | 0.0158 | 0.0132 | 2.9174 | NT |
| 49 | 1.1 | 0.0200 | 0.0040 | 0.0050 | 0.0135 | NT |
| 50 | 10.4 | 0.0158 | 0.0100 | 0.0104 | 6.7764 | NT |
| 51 | −0.8 | 0.0398 | 0.0079 | 0.0144 | 4.1020 | NT |
| 52 | 7.7 | 0.0316 | 0.0063 | 0.0102 | 0.1312 | NT |
| 53 | 4.0 | 0.0126 | 0.0079 | 0.0031 | 3.8637 | NT |
| 54 | 9.7 | 0.0251 | 0.0079 | 0.0061 | 8.9125 | NT |
| 55 | 15.3 | 0.0251 | 0.0158 | 0.0171 | 1.9724 | NT |
| 56 | 25.9 | 0.0398 | NT | 0.0308 | 5.9704 | NT |
| 57 | 0.5 | 0.0355 | NT | 0.0977 | >10 | NT |
| 58 | −2.0 | 0.0100 | NT | 0.0017 | 0.7129 | NT |
| 59 | 0.6 | 0.1259 | NT | 0.1005 | >10 | NT |
| 60 | 0.8 | 0.0219 | NT | 0.0149 | 2.3442 | NT |
| 61 | 11.2 | 0.0040 | NT | 0.0026 | 10.0000 | NT |
| 62 | 14.1 | 0.0063 | NT | 0.0196 | >10 | NT |

The following compounds were tested in additional runs for the assays described above and the data is provided in Table 2.

TABLE 2

P2X7 activity of the compounds of Formula (I) in a panel of in-vitro assays

| Example No. | PBMC 10 µM (% control) | P2X7 human Ki (µM) | P2X7 rat Ki (µM) | FLIPR (human) IC$_{50}$ (µM) | FLIPR (rat) IC$_{50}$ (µM) | Human whole blood IC$_{50}$ (µM) |
|---|---|---|---|---|---|---|
| 1 | 11.0 | 0.0501 | | 0.0038 | 0.0045 | |
| 2 | 45.7 | | | >10 | >10 | |
| 3 | 8.9 | 0.0398 | 0.0040 | 0.0096 | 0.0081 | |
| 4 | 6.1 | 0.0200 | | 0.0953 | 0.1327 | |
| 5 | −4.4 | 0.0126 | | 0.0634 | 0.0147 | |
| 6 | 5.8 | | | 2.2962 | 2.3227 | |
| 7 | 9.9 | 0.0126 | | 0.0077 | 0.0157 | |
| 8 | 7.3 | 0.0100 | 0.0013 | 0.0097 | 0.0025 | |
| 9 | 7.3 | 0.3981 | | 0.4819 | 0.1803 | |
| 11 | 38.9 | | | 6.1165 | 14.8252 | |
| 12 | 3.6 | 0.0126 | 0.0034 | 0.0131 | 0.0356 | 0.126 |
| 14 | 2.4 | 0.0174 | | 0.0100 | 0.0082 | |
| 15 | 89.8 | | | | | |
| 17 | 84.2 | | | | | |
| 18 | −9.0 | 0.0138 | | 0.0011 | 0.0044 | |
| 20 | 104.2 | | | | | |
| 21 | −2.1 | 0.0501 | | 0.0948 | 3.3497 | |
| 23 | 8.0 | 0.0240 | 0.0050 | 0.0404 | 0.0560 | |
| 24 | 32.7 | | | 3.6983 | >10 | |
| 26 | 9.2 | 0.0304 | 0.0040 | 0.0100 | 0.0014 | 0.040 |
| 27 | 4.8 | | | 1.9055 | 1.5417 | |
| 29 | 91.4 | | | | | |
| 30 | 1.4 | 0.0355 | | 0.1183 | 2.7733 | |
| 32 | 94.5 | | | 1.5136 | 2.1086 | |
| 33 | −1.0 | 0.0113 | 0.0025 | 0.0115 | 0.0078 | 0.044 |
| 35 | 82.2 | | | | | |
| 36 | −1.2 | 0.0107 | | 0.0365 | 0.3381 | |
| 38 | 101.0 | | | | | |
| 39 | 5.8 | 0.0251 | | 0.0511 | 0.0798 | |
| 40 | −1.3 | 0.0219 | 0.0355 | 0.0126 | 10.0000 | |
| 41 | −20.0 | 0.0126 | 0.0079 | 0.0063 | 1.5849 | |
| 42 | −21.3 | 0.0126 | 0.0079 | 0.0200 | 0.2512 | |
| 43 | −18.6 | 0.0129 | 0.0138 | 0.0200 | 3.9811 | |
| 44 | 7.9 | 0.0126 | 0.0126 | 0.0077 | 8.4918 | |
| 45 | 6.5 | 0.0126 | 0.0316 | 0.0131 | 15.8125 | |
| 46 | 10.0 | 0.0158 | 0.0063 | 0.0152 | 0.2529 | |
| 47 | 0.0 | 0.0100 | 0.0063 | 0.0203 | 1.9231 | |
| 48 | −0.6 | 0.0398 | 0.0158 | 0.0132 | 2.9174 | |
| 49 | 1.1 | 0.0200 | 0.0040 | 0.0050 | 0.0135 | |
| 50 | 10.4 | 0.0158 | 0.0100 | 0.0104 | 6.7764 | |
| 51 | −0.8 | 0.0398 | 0.0079 | 0.0144 | 4.1020 | |
| 52 | 7.7 | 0.0316 | 0.0063 | 0.0102 | 0.1312 | |
| 53 | 4.0 | 0.0126 | 0.0079 | 0.0031 | 3.8637 | |
| 54 | 9.7 | 0.0251 | 0.0079 | 0.0061 | 8.9125 | |
| 55 | 15.3 | 0.0251 | 0.0158 | 0.0171 | 1.9724 | |
| 56 | 25.9 | 0.0398 | | 0.0308 | 5.9704 | |
| 57 | 0.5 | 0.0355 | | 0.0977 | >10 | |
| 58 | −2.0 | 0.0100 | | 0.0017 | 0.7129 | |
| 59 | 0.6 | 0.1259 | | 0.1005 | >10 | |
| 60 | 0.8 | 0.0219 | | 0.0149 | 2.3442 | |
| 61 | 11.2 | 0.0040 | | 0.0026 | 10.0000 | |
| 62 | 14.1 | 0.0063 | | 0.0196 | >10 | |
| 193 | −13.8 | 0.0708 | 0.0049 | 0.0307 | 0.0411 | |
| 194 | −13.0 | 0.0141 | 0.0031 | 0.0173 | 0.0074 | |
| 195 | 11.2 | 0.0209 | | 0.0400 | >10 | |
| 196 | −0.2 | 0.0219 | 0.0058 | 0.0016 | 0.0017 | |
| 197 | 1.8 | 0.0191 | 0.0631 | 0.0107 | 1.4928 | |
| 198 | 4.1 | 0.0098 | 0.0062 | 0.0209 | 0.3266 | |
| 199 | −3.2 | 0.0251 | 0.0050 | 0.0295 | 0.0127 | |
| 200 | 7.7 | 0.0107 | 0.0032 | 0.0134 | 0.0102 | |
| 201 | −4.0 | 0.0115 | 0.0032 | 0.0140 | 0.7261 | |
| 202 | −2.3 | 0.0039 | 0.0058 | 0.0176 | 0.4618 | |
| 203 | −5.0 | 0.0053 | 0.0022 | 0.0253 | 0.0200 | |

What is claimed:
1. A pharmaceutical composition comprising:
(a) a therapeutically effective amount of at least one compound selected from the group consisting of:
11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;
(6R,10S)-11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;
11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;
(6S,10R)-11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;
(6R,10S)-11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;
11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;
(6S,10R)-11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;
(6R,10S)-11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;
11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;
(6S,10R)-11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;
(6R,10S)-11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;
11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;
(6S,10R)-11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;
(6R,10S)-11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;
11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;
(6S,10R)-11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;
(6R,10S)-11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;
11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;
(6S,10R)-11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;
(6R,10S)-11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;
11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;
(6S,10R)-11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;
(6R,10S)-11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;
11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;
(6S,10R)-11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;
(6R,10S)-11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;
3-(5-Chloropyridin-2-yl)-11-{[2-chloro-3-(trifluoromethyl)phenyl]carbonyl}-5,6,7,8,9,10-hexahydro-6,10-epimino[1,2,4]triazolo[4,3-a]azocine;
(6S,10R)-3-(5-Chloropyridin-2-yl)-11-{[2-chloro-3-(trifluoromethyl)phenyl]carbonyl}-5,6,7,8,9,10-hexahydro-6,10-epimino[1,2,4]triazolo[4,3-a]azocine;
(6R,10S)-3-(5-Chloropyridin-2-yl)-11-{[2-chloro-3-(trifluoromethyl)phenyl]carbonyl}-5,6,7,8,9,10-hexahydro-6,10-epimino[1,2,4]triazolo[4,3-a]azocine;
11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;
(6S,10R)-11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;
(6R,10S)-11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;
11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;
(6S,10R)-11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;
(6R,10S)-11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;
11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;
(6S,10R)-11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;
(6R,10S)-11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;
(6S,9R)-10-{[2-Chloro-3-(trifluoromethyl)phenyl]carbonyl}-3-(4-fluorophenyl)-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-pyridin-2-yl-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-pyrazin-2-yl-6,7,8,9-tetrahydro-5H-6,9-epimino[1,2,4]triazolo[4,3-a]azepine;
(6S,9R)-10-{[2-Chloro-4-fluoro-3-(trifluoromethyl)phenyl]carbonyl}-3-pyridin-2-yl-6,7,8,9-tetrahydro-5H-6,9-epimino[1,2,4]triazolo[4,3-a]azepine;
(6S,9R)-10-{[2-Methyl-3-(trifluoromethyl)phenyl]carbonyl}-3-pyridin-2-yl-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(5-fluoropyridin-2-yl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-pyrimidin-2-yl-6,7,8,9-tetrahydro-5H-6,9-epimino[1,2,4]triazolo[4,3-a]azepine;
(6S,9R)-10-[(2,3-Dichloro-4-fluorophenyl)carbonyl]-3-pyrazin-2-yl-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-pyridin-3-yl-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(5-fluoropyrimidin-2-yl)-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(3-methyl-1H-pyrazol-5-yl)-6,7,8,9-tetrahydro-5H-6,9-epimino[1,2,4]triazolo[4,3-a]azepine;
(6S,9R)-10-{[2-Chloro-4-fluoro-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;
(6S,9R)-10-{[2-Methyl-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;
(6S,9R)-10-[(2,4-Dichloro-3-fluorophenyl)carbonyl]-thiazol-4-yl)-6,7,8,9-tetrahydro-5H-6,9-epimino[1,2,4]triazolo[4,3-a]azepine;
(6S,9R)-3-(5-Chlorothiophen-2-yl)-10-{[2-chloro-3-(trifluoromethyl)phenyl]carbonyl}-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(2-methyl-1,3-thiazol-4-yl)-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(1,3-thiazol-5-yl)-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-thiophen-3-yl-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(4-methyl-1,3-thiazol-5-yl)-6,7,8,9-tetrahydro-5H-6,9-epimino[1,2,4]triazolo[4,3-a]azepine;
(6S,9R)-3-(5-Chlorothiophen-2-yl)-10-{[3-chloro-2-(trifluoromethyl)pyridin-4-yl]carbonyl}-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-thiophen-2-yl-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(1H-pyrrol-2-yl)-6,7,8,9-tetrahydro-5H-6,9-epimino[1,2,4]triazolo[4,3-a]azepine;
(2-chloro-4-fluoro-3-(trifluoromethyl)phenyl)(3-(pyridin-2-yl)-5,6,7,8,9,10-hexahydro-6,10-epimino[1,2,4]triazolo[4,3-a]azocin-11-yl)methanone;
(2-fluoro-3-(trifluoromethyl)phenyl)(3-(pyridin-2-yl)-5,6,7,8,9,10-hexahydro-6,10-epimino[1,2,4]triazolo[4,3-a]azocin-11-yl)methanone;
(3-chloro-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;
((2-methyl-3-(trifluoromethyl)phenyl)(3-(pyridin-2-yl)-5,6,7,8,9,10-hexahydro-6,10-epimino[1,2,4]triazolo[4,3-a]azocin-11-yl)methanone;
(3-methyl-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;
(3-fluoro-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;
(2,4-dichloro-3-fluorophenyl)(3-(pyridin-2-yl)-5,6,7,8,9,10-hexahydro-6,10-epimino[1,2,4]triazolo[4,3-a]azocin-11-yl)methanone;
(2,3-dichloro-4-fluorophenyl)(3-(pyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(3-fluoropyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(3,5-difluoropyridin-2-yl)-5,6,7,8,9,10-hexahydro-6,10-epimino[1,2,4]triazolo[4,3-a]azocin-11-yl)methanone;
((2-chloro-3-(trifluoromethyl)phenyl)(3-(5-fluoro-6-methylpyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(5-fluoro-4-methoxypyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-(trifluoromethoxy)pyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-(difluoromethoxy)pyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-hydroxypyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-ethoxypyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-isopropoxypyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(5-methylpyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-methylpyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-(trifluoromethyl)pyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(5-fluoro-4-methylpyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(5-fluoro-4-(trifluoromethyl)pyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(pyrazin-2-yl)-6,7,9,10-tetrahydro-5H-6,10-epimino[1,2,4]triazolo[3,4-d][1,5]oxazocin-11-yl)methanone;
(2-methyl-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;
(2-fluoro-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(pyrazin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;
(2-methyl-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;
(2-fluoro-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(pyrazin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;
((6R,10S)-3-(5-fluoropyrimidin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;
(2-fluoro-3-(trifluoromethyl)phenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;
((6R,10S)-3-(5-fluoropyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;
(2-fluoro-3-(trifluoromethyl)phenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;
((6R,10S)-3-(4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;
(2-fluoro-3-(trifluoromethyl)phenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(2-methyl-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(2-fluoro-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(pyridin-2-yl)-6,7,9,10-tetrahydro-5H-6,10-epimino[1,2,4]triazolo[3,4-d][1,5]oxazocin-11-yl)methanone;
(2-methyl-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;
(2-fluoro-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(pyridin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(pyridin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-chloro-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2,3-dichloro-4-fluorophenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-fluoro-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2,3-dichlorophenyl)methanone;

(2-chloro-3-(trifluoromethyl)phenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-fluorophenyl)-6,7,9,10-tetrahydro-5H-6,10-epimino[1,2,4]triazolo[3,4-d][1,5]oxazocin-11-yl)methanone;

((6R,10S)-3-(4-fluorophenyl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-fluorophenyl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(2-fluoro-3-(trifluoromethyl)phenyl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

(2,3-dichlorophenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

(2,3-dichlorophenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

((6R,10S)-3-(3-fluoropyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(thiazol-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(thiazol-4-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(6R,10S)-11-{[2-Chloro-3-(trifluoromethyl)phenyl]carbonyl}-3-(5-fluoro-6-methylpyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(4-methylpyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyridazin-3-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-[4-(trifluoromethyl)pyridin-2-yl]-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyrimidin-4-yl-5,6,7,8,9,10-hexahydro-6,10-epimino[1,2,4]triazolo[4,3-a]azocine;

(6R,10S)-11-{[3-Fluoro-2-(trifluoromethyl)pyridin-4-yl]carbonyl}-3-pyridin-2-yl-5,6,7,8,9,10-hexahydro-6,10-epimino[1,2,4]triazolo[4,3-a]azocine;

(6R,10S)-11-{[3-Chloro-2-(trifluoromethyl)pyridin-4-yl]carbonyl}-3-pyridin-2-yl-5,6,7,8,9,10-hexahydro-6,10-epimino[1,2,4]triazolo[4,3-a]azocine;

6R,10S)-11-{[2-Chloro-4-fluoro-3-(trifluoromethyl)phenyl]carbonyl}-3-pyridin-2-yl-5,6,7,8,9,10-hexahydro-6,10-epimino[1,2,4]triazolo[4,3-a]azocine;

(6R,10S)-11-{[2-Methyl-3-(trifluoromethyl)phenyl]carbonyl}-3-pyridin-2-yl-5,6,7,8,9,10-hexahydro-6,10-epimino[1,2,4]triazolo[4,3-a]azocine;

(6R,10S)-11-[(2,4-Dichloro-3-fluorophenyl)carbonyl]-3-pyridin-2-yl-5,6,7,8,9,10-hexahydro-6,10-epimino[1,2,4]triazolo[4,3-a]azocine; and (6R,10S)-11-[(2,3-Dichloro-4-fluorophenyl)carbonyl]-3-pyridin-2-yl-5,6,7,8,9,10-hexahydro-6,10-epimino[1,2,4]triazolo[4,3-a]azocine; and (b) at least one pharmaceutically acceptable excipient.

2. The pharmaceutical composition according to claim 1, wherein the composition is an oral dosage form.

3. A method of treating a condition selected from the group consisting of: major depressive disorder, treatment-resistant depression, anxious depression, bipolar disorder, anxiety, epileptic seizures, Alzheimer's disease, Parkinson's disease, irritable bowel syndrome, irritable bowel disease, Crohn's disease, rheumatoid arthritis, osteoarthritis, psoriasis, allergic dermatitis, asthma, allergic asthma, allergic rhinitis, neuropathic pain, inflammatory pain, and spontaneous pain, comprising administering to a subject in need thereof a therapeutically effective amount of a compound selected from the group consisting of:

11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyrimidin-2-yl-5,6,7,8,9,10-hexahydro-6,10-epimino[1,2,4]triazolo[4,3-a]azocine;

11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(4-fluorophenyl)-5,6,7,8,9,10-hexahydro-6,10-epimino[1,2,4]triazolo[4,3-a]azocine;

11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(1,3-thiazol-4-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(5-fluoropyridin-2-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyridin-3-yl-5,6,7,8,9,10-hexahydro-6,10-epimino[1,2,4]triazolo[4,3-a]azocine;

11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(5-fluoropyrimidin-2-yl)-5,6,7,8,9,10-hexahydro-6,10-epimino[1,2,4]triazolo[4,3-a]azocine;

11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;

(6S,10R)-11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;

(6R,10S)-11-[(2,4-Dichlorophenyl)carbonyl]-3-(5-fluoropyrimidin-2-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(6-methylpyridin-2-yl)-5,6,7,8,9,10-hexahydro-6,10-epimino[1,2,4]triazolo[4,3-a]azocine;

11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(4-methoxypyridin-2-yl)-5,6,7,8,9,10-hexahydro-6,10-epimino[1,2,4]triazolo[4,3-a]azocine;

3-(5-Chloropyridin-2-yl)-11-{[2-chloro-3-(trifluoromethyl)phenyl]carbonyl}-5,6,7,8,9,10-hexahydro-6,10-epimino[1,2,4]triazolo[4,3-a]azocine;

(6S,10R)-3-(5-Chloropyridin-2-yl)-11-{[2-chloro-3-(trifluoromethyl)phenyl]carbonyl}-5,6,7,8,9,10-hexahydro-6,10-epimino[1,2,4]triazolo[4,3-a]azocine;

(6R,10S)-3-(5-Chloropyridin-2-yl)-11-{[2-chloro-3-(trifluoromethyl)phenyl]carbonyl}-5,6,7,8,9,10-hexahydro-6,10-epimino[1,2,4]triazolo[4,3-a]azocine;

11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;

(6S,10R)-11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyridin-2-yl-5,6,7,8,9,10-hexahydro-6,10-epimino[1,2,4]triazolo[4,3-a]azocine;

11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;

(6S,10R)-11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;

(6R,10S)-11-{[3-Chloro-2-(trifluoromethyl)pyridin-4-yl]carbonyl}-3-thiophen-2-yl-5,6,7,8,9,10-hexahydro-6,10-epimino[1,2,4]triazolo[4,3-a]azocine;

11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;

(6S,10R)-11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;

(6R,10S)-11-{[3-Chloro-2-(trifluoromethyl)pyridin-4-yl]carbonyl}-3-(5-methylthiophen-2-yl)-5,6,7,8,9,10-hexahydro-6,10-epimino[1,2,4]triazolo[4,3-a]azocine;

(6S,9R)-10-{[2-Chloro-3-(trifluoromethyl)phenyl]carbonyl}-3-(4-fluorophenyl)-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-pyridin-2-yl-6,7,8,9-tetrahydro-5H-6,9-epimino[1,2,4]triazolo[4,3-a]azepine;

(6S,9R)-10-{[2-Chloro-3-(trifluoromethyl)phenyl]carbonyl}-3-pyrazin-2-yl-6,7,8,9-tetrahydro-5H-6,9-epimino[1,2,4]triazolo[4,3-a]azepine;

(6S,9R)-10-{[2-Chloro-4-fluoro-3-(trifluoromethyl)phenyl]carbonyl}-3-pyridin-2-yl-6,7,8,9-tetrahydro-5H-6,9-epimino[1,2,4]triazolo[4,3-a]azepine;

(6S,9R)-10-{[2-Methyl-3-(trifluoromethyl)phenyl]carbonyl}-3-pyridin-2-yl-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(5-fluoropyridin-2-yl)-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-pyrimidin-2-yl-6,7,8,9-tetrahydro-5H-6,9-epimino[1,2,4]triazolo[4,3-a]azepine;
(6S,9R)-10-[(2,3-Dichloro-4-fluorophenyl)carbonyl]-3-pyrazin-2-yl-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-pyridin-3-yl-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(5-fluoropyrimidin-2-yl)-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(3-methyl-1H-pyrazol-5-yl)-6,7,8,9-tetrahydro-5H-6,9-epimino[1,2,4]triazolo[4,3-a]azepine;
(6S,9R)-10-{[2-Chloro-4-fluoro-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;
(6S,9R)-10-{[2-Methyl-3-(trifluoromethyl)phenyl]carbonyl}-3-(1,3-thiazol-4-yl)-6,7,8,9-tetrahydro-5H-6,9-epimino[1,2,4]triazolo[4,3-a]azepine;
(6S,9R)-10-[(2,4-Dichloro-3-fluorophenyl)carbonyl]-3-(1,3-thiazol-4-yl)-6,7,8,9-tetrahydro-5H-6,9-epimino[1,2,4]triazolo[4,3-a]azepine;
(6S,9R)-3-(5-Chlorothiophen-2-yl)-10-{[2-chloro-3-(trifluoromethyl)phenyl]carbonyl}-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(2-methyl-1,3-thiazol-4-yl)-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(1,3-thiazol-5-yl)-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-thiophen-3-yl-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(4-methyl-1,3-thiazol-5-yl)-6,7,8,9-tetrahydro-5H-6,9-epimino[1,2,4]triazolo[4,3-a]azepine;
(6S,9R)-3-(5-Chlorothiophen-2-yl)-10-{[3-chloro-2-(trifluoromethyl)pyridin-4-yl]carbonyl}-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-thiophen-2-yl-6,7,8,9-tetrahydro-5H-6,9-epimino[1,2,4]triazolo[4,3-a]azepine;
(6S,9R)-10-{[2-Chloro-3-(trifluoromethyl)phenyl]carbonyl}-3-(1H-pyrrol-2-yl)-6,7,8,9-tetrahydro-5H-6,9-epimino[1,2,4]triazolo[4,3-a]azepine;
(2-chloro-4-fluoro-3-(trifluoromethyl)phenyl)(3-(pyridin-2-yl)-5,6,7,8,9,10-hexahydro-6,10-epimino[1,2,4]triazolo[4,3-a]azocin-11-yl)methanone;
(2-fluoro-3-(trifluoromethyl)phenyl)(3-(pyridin-2-yl)-5,6,7,8,9,10-hexahydro-6,10-epimino[1,2,4]triazolo[4,3-a]azocin-11-yl)methanone;
(3-chloro-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;
((2-methyl-3-(trifluoromethyl)phenyl)(3-(pyridin-2-yl)-5,6,7,8,9,10-hexahydro-6,10-epimino[1,2,4]triazolo[4,3-a]azocin-11-yl)methanone;
(3-methyl-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;
(3-fluoro-2-(trifluoromethyl)pyridin-4-yl)(3-(pyridin-2-yl)-5,6,7,8,9,10-hexahydro-6,10-epimino[1,2,4]triazolo[4,3-a]azocin-11-yl)methanone;
(2,4-dichloro-3-fluorophenyl)(3-(pyridin-2-yl)-5,6,7,8,9,10-hexahydro-6,10-epimino[1,2,4]triazolo[4,3-a]azocin-11-yl)methanone;
(2,3-dichloro-4-fluorophenyl)(3-(pyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(3-fluoropyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(3,5-difluoropyridin-2-yl)-5,6,7,8,9,10-hexahydro-6,10-epimino[1,2,4]triazolo[4,3-a]azocin-11-yl)methanone;
((2-chloro-3-(trifluoromethyl)phenyl)(3-(5-fluoro-6-methylpyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(5-fluoro-4-methoxypyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-(trifluoromethoxy)pyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-(difluoromethoxy)pyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-hydroxypyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-ethoxypyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-isopropoxypyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(5-methylpyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-methylpyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(4-(trifluoromethyl)pyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(5-fluoro-4-methylpyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)(3-(5-fluoro-4-(trifluoromethyl)pyridin-2-yl)-5,6,7,8,9,10-hexahydro-6,10-epimino[1,2,4]triazolo[4,3-a]azocin-11-yl)methanone;
(2-chloro-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(pyrazin-2-yl)-6,7,9,10-tetrahydro-5H-6,10-epimino[1,2,4]triazolo[3,4-d][1,5]oxazocin-11-yl)methanone;
(2-methyl-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(pyrazin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(pyrazin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(pyrazin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;
(2-methyl-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;
(2-fluoro-3-(trifluoromethyl)phenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(pyrazin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(pyrimidin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;
((6R,10S)-3-(5-fluoropyrimidin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;
(2-fluoro-3-(trifluoromethyl)phenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(5-fluoropyrimidin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;
((6R,10S)-3-(5-fluoropyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;
(2-fluoro-3-(trifluoromethyl)phenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(5-fluoropyridin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;
((6R,10S)-3-(4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;
(2-fluoro-3-(trifluoromethyl)phenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(4-methoxypyridin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(2-methyl-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(2-fluoro-3-(trifluoromethyl)phenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(4-(trifluoromethoxy)pyridin-2-yl)-6,7,9,10-tetrahydro-5H-6,10-epimino[1,2,4]triazolo[3,4-d][1,5]oxazocin-11-yl)methanone;
(2-chloro-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;
(2,3-dichloro-4-fluorophenyl)((6R,10S)-3-(pyridin-2-yl)-6,7,9,10-tetrahydro-5H-6,10-epimino[1,2,4]triazolo[3,4-d][1,5]oxazocin-11-yl)methanone;
(2-methyl-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;
(2-fluoro-3-(trifluoromethyl)phenyl)((6R,10S)-3-(pyridin-2-yl)-6,7,9,10-tetrahydro-5H-6,10-epimino[1,2,4]triazolo[3,4-d][1,5]oxazocin-11-yl)methanone;
(3-fluoro-2-(trifluoromethyl)pyridin-4-yl)((6R,10S)-3-(pyridin-2-yl)-6,7,9,10-tetrahydro-5H-6,10-epimino[1,2,4]triazolo[3,4-d][1,5]oxazocin-11-yl)methanone;
(2,3-dichlorophenyl)((6R,10S)-3-(pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(5-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-chloro-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2,3-dichloro-4-fluorophenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2-fluoro-3-(trifluoromethyl)phenyl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

((6R,10S)-3-(1H-pyrazol-3-yl)-6,7,9,10-tetrahydro-5H-6,10-epimino[1,2,4]triazolo[3,4-d][1,5]oxazocin-11-yl)(2,3-dichlorophenyl)methanone;

(2-chloro-3-(trifluoromethyl)phenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-fluorophenyl)-6,7,9,10-tetrahydro-5H-6,10-epimino[1,2,4]triazolo[3,4-d][1,5]oxazocin-11-yl)methanone;

((6R,10S)-3-(4-fluorophenyl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-fluorophenyl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(4-fluorophenyl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(3-fluoro-4-methoxypyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(2-fluoro-3-(trifluoromethyl)phenyl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

(2,3-dichlorophenyl)((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

((6R,10S)-3-(4-(difluoromethoxy)pyridin-2-yl)-6,7,9,10-tetrahydro-5H-6,10-epimino[1,2,4]triazolo[3,4-d][1,5]oxazocin-11-yl)(3-fluoro-2-(trifluoromethyl)pyridin-4-yl)methanone;

(2,3-dichlorophenyl)((6R,10S)-3-(5-fluoro-6-methylpyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(4-(trifluoromethyl)pyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(6-methylpyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

((6R,10S)-3-(3-fluoropyridin-2-yl)-6,7,9,10-tetrahydro-5H-6,10-epimino[1,2,4]triazolo[3,4-d][1,5]oxazocin-11-yl)(2-methyl-3-(trifluoromethyl)phenyl)methanone;

(2-fluoro-3-(trifluoromethyl)phenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(3-fluoropyridin-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(thiazol-2-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(thiazol-2-yl)-6,7,9,10-tetrahydro-5H-6,10-epimino[1,2,4]triazolo[3,4-d][1,5]oxazocin-11-yl)methanone;

(2-chloro-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2,3-dichloro-4-fluorophenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2-methyl-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(2-fluoro-3-(trifluoromethyl)phenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(3-fluoro-2-(trifluoromethyl)pyridin-4-yl)((6R,10S)-3-(thiazol-4-yl)-6,7,9,10-tetrahydro-5H-6,10-epimino[1,2,4]triazolo[3,4-d][1,5]oxazocin-11-yl)methanone;

(2,3-dichlorophenyl)((6R,10S)-3-(thiazol-4-yl)-6,7,9,10-tetrahydro-5H-6,10-epimino[1,2,4]triazolo[3,4-d][1,5]oxazocin-11-yl)methanone;

(6R,10S)-11-{[2-Chloro-3-(trifluoromethyl)phenyl]carbonyl}-3-(5-fluoro-6-methylpyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-(4-methylpyridin-2-yl)-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyridazin-3-yl-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-[4-(trifluoromethyl)pyridin-2-yl]-5,6,7,8,9,10-hexahydro-6,10-epimino[1,2,4]triazolo[4,3-a]azocine;

(6R,10S)-11-{[2-Chloro-3-(trifluoromethyl)phenyl]carbonyl}-3-pyrimidin-4-yl-5,6,7,8,9,10-hexahydro-6,10-epimino[1,2,4]triazolo[4,3-a]azocine;

(6R,10S)-11-{[3-Fluoro-2-(trifluoromethyl)pyridin-4-yl]carbonyl}-3-pyridin-2-yl-5,6,7,8,9,10-hexahydro-6,10-epimino[1,2,4]triazolo[4,3-a]azocine;

(6R,10S)-11-{[3-Chloro-2-(trifluoromethyl)pyridin-4-yl]carbonyl}-3-pyridin-2-yl-5,6,7,8,9,10-hexahydro-6,10-epimino[1,2,4]triazolo[4,3-a]azocine;

6R,10S)-11-{[2-Chloro-4-fluoro-3-(trifluoromethyl)phenyl]carbonyl}-3-pyridin-2-yl-5,6,7,8,9,10-hexahydro-6,10-epimino[1,2,4]triazolo[4,3-a]azocine;

(6R,10S)-11-{[2-Methyl-3-(trifluoromethyl)phenyl]carbonyl}-3-pyridin-2-yl-5,6,7,8,9,10-hexahydro-6,10-epimino[1,2,4]triazolo[4,3-a]azocine;

(6R,10S)-11-[(2,4-Dichloro-3-fluorophenyl)carbonyl]-3-pyridin-2-yl-5,6,7,8,9,10-hexahydro-6,10-epimino[1,2,4]triazolo[4,3-a]azocine; and (6R,10S)-11-[(2,3-Dichloro-4-fluorophenyl)carbonyl]-3-pyridin-2-yl-5,6,7,8,9,10-hexahydro-6,10-epimino[1,2,4]triazolo[4,3-a]azocine.

4. The method according to claim 3, wherein the condition is selected from the group consisting of major depressive disorder, treatment-resistant depression, anxious depression, bipolar disorder, and anxiety.

5. The method according to claim 3, wherein the condition is selected from the group consisting of irritable bowel syndrome, irritable bowel disease, and Crohn's disease.

6. The method according to claim 3, wherein the condition is Alzheimer's disease.

* * * * *